United States Patent
Yu et al.

(10) Patent No.: US 10,907,136 B2
(45) Date of Patent: Feb. 2, 2021

(54) METHOD FOR PRODUCING MUTANT ENZYME, AND MUTANT ALCOHOL ACYLTRANSFERASE

(71) Applicant: Mitsubishi Chemical Corporation, Tokyo (JP)

(72) Inventors: Fujio Yu, Tokyo (JP); Wataru Mizunashi, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 16/288,970

(22) Filed: Feb. 28, 2019

(65) Prior Publication Data

US 2019/0185825 A1 Jun. 20, 2019

Related U.S. Application Data

(63) Continuation of application No. PCT/JP2017/031116, filed on Aug. 30, 2017.

(30) Foreign Application Priority Data

Aug. 30, 2016 (JP) .................................. 2016-168195

(51) Int. Cl.
| | |
|---|---|
| *C12N 9/10* | (2006.01) |
| *C12N 15/09* | (2006.01) |
| *C12P 21/02* | (2006.01) |
| *C12P 7/62* | (2006.01) |

(52) U.S. Cl.
CPC ............... *C12N 9/10* (2013.01); *C12N 15/09* (2013.01); *C12P 7/62* (2013.01); *C12P 21/02* (2013.01)

(58) Field of Classification Search
CPC ........................................................ C12N 9/10
See application file for complete search history.

(56) References Cited

U.S. PATENT DOCUMENTS

| | | | |
|---|---|---|---|
| 2008/0008695 A1 | 1/2008 | Vellard et al. | |
| 2010/0261249 A1 | 10/2010 | Okumura et al. | |
| 2015/0079649 A1* | 3/2015 | Sonke ................. | C12P 7/26 435/148 |
| 2015/0140620 A1 | 5/2015 | Zhang et al. | |
| 2015/0184207 A1 | 7/2015 | Sato et al. | |
| 2015/0191756 A1 | 7/2015 | Sato et al. | |

FOREIGN PATENT DOCUMENTS

| | | |
|---|---|---|
| EP | 2 848 694 A1 | 3/2015 |
| JP | 2010-529835 A | 9/2010 |
| JP | 2014/038216 A1 | 3/2014 |
| JP | 2014-519841 A | 8/2014 |
| JP | 2015-517824 A | 6/2015 |
| JP | 2015116141 A | 6/2015 |
| WO | 2009/005140 A1 | 1/2009 |
| WO | 2012/169341 A1 | 12/2012 |
| WO | WO 2012/177129 A2 | 12/2012 |
| WO | WO 2013/180810 A1 | 12/2013 |
| WO | 2014/038214 A1 | 3/2014 |

OTHER PUBLICATIONS

Extended European Search Report dated Jul. 30, 2019, in Patent Application No. 17846550.6, 18 pages.
Database Uniparc [online], "methanol O-anthraniloyltransferase-like", Retrieved from NCBI, XP002792828, Database accession No. XP008391402.1, Jun. 22, 2016, 2 pages.
Partial Supplementary European Search Report dated May 15, 2019 in Patent Application No. 17846550.6, 19 pages.
El Hadi, M.A.M. et al. "Identification and Expression of Alcohol Acyltransferase (AAT1) Responsible for Ester Biosynthesis in Persimmon (*Diospyrus kaki* L.) Fruits" Database UniProt, https://www.uniprot.org/uniprot/A0A0F6VXG8.txt?version=3, XP02790974, 2015, 1 Page.
Fugii, T. et al. "Molecular Cloning, Sequence Analysis, and Expression of the Yeast Alcohol Acetyltransferase Gene" Applied and Environmental Microbiology, http://aem.asm.org/content/60/8/2786.full.pdf, vol. 60, No. 8, XP055090551, 1994, 8 Pages.
European Office Action dated May 8, 2020 in Patent Application No. 17 846 550.6, 7 pages.
International Search Report dated Dec. 5. 2017 issued in corresponding application PCT/JP2017/031116.
Li et al.—"Molecular cloning and expression of a gene encoding alcohol acyltransferase (MdAAT2) from apple (cv. Golden Delicious)", Phytochemistry 67 (2006), pp. 658-667.
Souleyre et al.—"An alcohol acyl transferase from apple (cv. Royal Gala), MpAAT1, produces esters involved in apple fruit flavor", FEBS Journal 272 (2005), pp. 3132-3144.
Asano et al.—"Functional expression of a plant hydroxynitrile lyase in *Escherichia coli* by directed evolution: creation and characterization by highly in vivo soluble mutants", Protein Engineering. Design & Selection vol. 24, No. 8, pp. 607-616 (2011).
Tai et al.—"Engineered biosynthesis of medium-chain esters in *Escherichia coli*", Metabolic Engineering 27 (2015), pp. 20-28.

(Continued)

*Primary Examiner* — Tekchand Saidha
(74) *Attorney, Agent, or Firm* — Oblon, McClelland, Maier & Neustadt, L.L.P.

(57) ABSTRACT

It is intended to provide an efficient method for expressing a protein of interest as an active soluble recombinant protein in a transformant. The present invention provides a method for producing an enzyme having improved activity per recombinant as compared with a reference form, comprising the steps of: (1) preparing recombinants each expressing a mutant having an amino acid sequence derived from the amino acid sequence of the reference form by the substitution of one or more cysteine residues by other amino acid residues; (2) selecting a plurality of mutants that exhibit 50% or more activity per recombinant relative to 100% activity of the reference form; and (3) expressing a mutant in which corresponding amino acid residues are substituted at two or more positions among the respective positions of the substituted amino acid residues of the mutants selected in step (2).

15 Claims, 8 Drawing Sheets

Specification includes a Sequence Listing.

(56) References Cited

OTHER PUBLICATIONS

Kyono, "Can we know the solubility of the recombinant protein just by looking at the colonies!?" Chemistry and Biology, vol. 42, No. 10, pp. 663-665 (with non-official translation).

Goulet et al.—"Divergence in the Enzymatic Activities of a Tomato and *Solanum pennellii* Alcohol Acyltransferase Impacts Fruit Volatile Ester Composition", Molecular Plant 8, pp. 153-162, Jan. 2015.

Office Action dated Sep. 2, 2020, in European patent application No. 17 846 550.6 (5 pages).

* cited by examiner

```
                              SEQUENCE LISTING

<160> NUMBER OF SEQ ID NOS: 73

<210> SEQ ID NO 1
<211> LENGTH: 455
<212> TYPE: PRT
<213> ORGANISM: Malus domestica

<400> SEQUENCE: 1

Met Met Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Met Cys
        35                  40                  45

Tyr Lys Asp Asn Pro Ser Leu Asn Lys Asn Arg Asn Pro Val Lys Ala
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Lys Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Cys Leu Thr Cys Gly Gly Phe Ile Leu Ala Leu
145                 150                 155                 160

Arg Leu Asn His Thr Met Cys Asp Ala Ala Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335
```

-continued

```
Val Lys Lys Ala Lys Ala Thr Met Asn Glu Glu Tyr Leu Arg Ser Val
            340                 345                 350
Ala Asp Leu Leu Val Leu Arg Gly Arg Pro Gln Tyr Ser Ser Thr Gly
        355                 360                 365
Ser Tyr Leu Ile Val Ser Asp Asn Thr Arg Val Gly Phe Gly Asp Val
    370                 375                 380
Asn Phe Gly Trp Gly Gln Pro Val Phe Ala Gly Pro Val Lys Ala Leu
385                 390                 395                 400
Asp Leu Ile Ser Phe Tyr Val Gln His Lys Asn Asn Thr Glu Asp Gly
            405                 410                 415
Ile Leu Val Pro Met Cys Leu Pro Ser Ser Ala Met Glu Arg Phe Gln
        420                 425                 430
Gln Glu Leu Glu Arg Ile Thr Gln Glu Pro Lys Glu Asp Ile Cys Asn
    435                 440                 445
Asn Leu Arg Ser Thr Ser Gln
450                 455

<210> SEQ ID NO 2
<211> LENGTH: 455
<212> TYPE: PRT
<213> ORGANISM: Artificial Sequence
<220> FEATURE:
<223> OTHER INFORMATION: Apple M2K-AAT (pAAT116)

<400> SEQUENCE: 2

Met Lys Ser Phe Ser Val Leu Gln Val Lys Arg Leu Gln Pro Glu Leu
1               5                   10                  15
Ile Thr Pro Ala Lys Ser Thr Pro Gln Glu Thr Lys Phe Leu Ser Asp
            20                  25                  30
Ile Asp Asp Gln Glu Ser Leu Arg Val Gln Ile Pro Ile Ile Met Cys
        35                  40                  45
Tyr Lys Asp Asn Pro Ser Leu Asn Lys Asn Arg Asn Pro Val Lys Ala
    50                  55                  60
Ile Arg Glu Ala Leu Ser Arg Ala Leu Val Tyr Tyr Tyr Pro Leu Ala
65                  70                  75                  80
Gly Arg Leu Arg Glu Gly Pro Asn Arg Lys Leu Val Val Asp Cys Asn
            85                  90                  95
Gly Glu Gly Ile Leu Phe Val Glu Ala Ser Ala Asp Val Thr Leu Glu
        100                 105                 110
Gln Leu Gly Asp Lys Ile Leu Pro Pro Cys Pro Leu Leu Glu Glu Phe
    115                 120                 125
Leu Tyr Asn Phe Pro Gly Ser Asp Gly Ile Ile Asp Cys Pro Leu Leu
130                 135                 140
Leu Ile Gln Val Thr Cys Leu Thr Cys Gly Gly Phe Ile Leu Ala Leu
145                 150                 155                 160
Arg Leu Asn His Thr Met Cys Asp Ala Ala Gly Leu Leu Leu Phe Leu
            165                 170                 175
Thr Ala Ile Ala Glu Met Ala Arg Gly Ala His Ala Pro Ser Ile Leu
        180                 185                 190
Pro Val Trp Glu Arg Glu Leu Leu Phe Ala Arg Asp Pro Pro Arg Ile
    195                 200                 205
Thr Cys Ala His His Glu Tyr Glu Asp Val Ile Gly His Ser Asp Gly
210                 215                 220
Ser Tyr Ala Ser Ser Asn Gln Ser Asn Met Val Gln Arg Ser Phe Tyr
225                 230                 235                 240
```

```
Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Gln Tyr Ser Ser Thr Gly
        355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Cys Asn
        435                 440                 445

Asn Leu Arg Ser Thr Ser Gln
    450                 455

<210> SEQ ID NO 3
<211> LENGTH: 455
<212> TYPE: PRT
<213> ORGANISM: Artificial Sequence
<220> FEATURE:
<223> OTHER INFORMATION: Quadruple mutant apple AAT (pAAT021)

<400> SEQUENCE: 3

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Ile Met Cys
        35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140
```

```
Leu Ile Gln Val Thr Cys Leu Thr Cys Gly Gly Phe Ile Leu Ala Leu
145                 150                 155                 160

Arg Leu Asn His Thr Met Cys Asp Ala Ala Gly Leu Leu Phe Leu
            165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Arg Ile
        195                 200                 205

Thr Cys Ala His His Glu Tyr Glu Asp Val Ile Gly His Ser Asp Gly
210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Cys Leu Trp
                260                 265                 270

Lys Cys Arg Thr Leu Ala Leu Asn Ile Asn Pro Lys Glu Ala Val Arg
            275                 280                 285

Val Ser Cys Ile Val Asn Ala Arg Gly Lys His Asn Asn Val Arg Leu
290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
                355                 360                 365

Ser Tyr Leu Ile Val Ser Asp Asn Thr Arg Val Gly Phe Gly Asp Val
            370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
                420                 425                 430

Gln Glu Leu Glu Arg Ile Thr Gln Pro Lys Glu Asp Ile Cys Asn
            435                 440                 445

Asn Leu Arg Ser Thr Ser Gln
    450                 455

<210> SEQ ID NO 4
<211> LENGTH: 455
<212> TYPE: PRT
<213> ORGANISM: Artificial Sequence
<220> FEATURE:
<223> OTHER INFORMATION: 6 cysteine substituted apple AAT (pAAT024)

<400> SEQUENCE: 4

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Met Ala
        35                  40                  45
```

```
Tyr Lys Asp Asn Pro Ser Leu Asn Lys Asn Arg Asn Pro Val Lys Ala
     50                  55                  60

Ile Arg Glu Ala Leu Ser Arg Ala Leu Val Tyr Tyr Pro Leu Ala
 65              70                  75                  80

Gly Arg Leu Arg Glu Gly Pro Asn Arg Lys Leu Val Val Asp Cys Asn
                 85                  90                  95

Gly Glu Gly Ile Leu Phe Val Glu Ala Ser Ala Asp Val Thr Leu Glu
                100                 105                 110

Gln Leu Gly Asp Lys Ile Leu Pro Pro Cys Pro Leu Leu Glu Glu Phe
                115                 120                 125

Leu Tyr Asn Phe Pro Gly Ser Asp Gly Ile Ile Asp Cys Pro Leu Leu
    130                 135                 140

Leu Ile Gln Val Thr Ala Leu Thr Cys Gly Gly Phe Ile Leu Ala Leu
145                 150                 155                 160

Arg Leu Asn His Thr Met Ala Asp Ala Ala Gly Leu Leu Leu Phe Leu
                165                 170                 175

Thr Ala Ile Ala Glu Met Ala Arg Gly Ala His Ala Pro Ser Ile Leu
                180                 185                 190

Pro Val Trp Glu Arg Glu Leu Leu Phe Ala Arg Asp Pro Pro Arg Ile
            195                 200                 205

Thr Cys Ala His His Glu Tyr Glu Asp Val Ile Gly His Ser Asp Gly
            210                 215                 220

Ser Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Ala Leu Trp
                260                 265                 270

Lys Ala Arg Thr Leu Ala Leu Asn Ile Asn Pro Lys Glu Ala Val Arg
                275                 280                 285

Val Ser Cys Ile Val Asn Ala Arg Gly Lys His Asn Asn Val Arg Leu
                290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
                340                 345                 350

Ala Asp Leu Leu Val Leu Arg Gly Arg Pro Gln Tyr Ser Ser Thr Gly
                355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
                420                 425                 430

Gln Glu Leu Glu Arg Ile Thr Gln Glu Pro Lys Glu Asp Ile Ala Asn
                435                 440                 445

Asn Leu Arg Ser Thr Ser Gln
    450                 455
```

-continued

```
<210> SEQ ID NO 5
<211> LENGTH: 455
<212> TYPE: PRT
<213> ORGANISM: Artificial Sequence
<220> FEATURE:
<223> OTHER INFORMATION: Quadruple mutant and 6 cysteine substituted
      apple AAT (pAAT025)

<400> SEQUENCE: 5

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Ile Met Ala
        35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Ala Leu Thr Cys Gly Gly Phe Ile Leu Ala Leu
145                 150                 155                 160

Arg Leu Asn His Thr Met Ala Asp Ala Ala Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Ala Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365
```

```
Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
                420                 425                 430

Gln Glu Leu Glu Arg Ile Thr Gln Glu Pro Lys Glu Asp Ile Ala Asn
                435                 440                 445

Asn Leu Arg Ser Thr Ser Gln
    450                 455

<210> SEQ ID NO 6
<211> LENGTH: 455
<212> TYPE: PRT
<213> ORGANISM: Artificial Sequence
<220> FEATURE:
<223> OTHER INFORMATION: Quadruple mutant and Cys150Arg apple AAT
      (pAAT155)

<400> SEQUENCE: 6

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
                20                  25                  30

Ile Asp Asp Gln Glu Ser Leu Arg Val Gln Ile Pro Ile Ile Met Cys
                35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Arg Leu Thr Cys Gly Gly Phe Ile Leu Ala Leu
145                 150                 155                 160

Arg Leu Asn His Thr Met Cys Asp Ala Ala Gly Leu Leu Phe Leu
                165                 170                 175

Thr Ala Ile Ala Glu Met Ala Arg Gly Ala His Ala Pro Ser Ile Leu
                180                 185                 190

Pro Val Trp Glu Arg Glu Leu Leu Phe Ala Arg Asp Pro Pro Arg Ile
            195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Cys Leu Trp
            260                 265                 270
```

```
Lys Cys Arg Thr Leu Ala Leu Asn Ile Asn Pro Lys Glu Ala Val Arg
            275                 280                 285

Val Ser Cys Ile Val Asn Ala Arg Gly Lys His Asn Asn Val Arg Leu
            290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
            355                 360                 365

Ser Tyr Leu Ile Val Ser Asp Asn Thr Arg Val Gly Phe Gly Asp Val
370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
                420                 425                 430

Gln Glu Leu Glu Arg Ile Thr Gln Glu Pro Lys Glu Asp Ile Cys Asn
            435                 440                 445

Asn Leu Arg Ser Thr Ser Gln
450                 455

<210> SEQ ID NO 7
<211> LENGTH: 455
<212> TYPE: PRT
<213> ORGANISM: Artificial Sequence
<220> FEATURE:
<223> OTHER INFORMATION: Quadruple mutant and 6 cysteine substituted
      (Cys150Arg) apple AAT (pAAT154)

<400> SEQUENCE: 7

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
                20                  25                  30

Ile Asp Asp Gln Glu Ser Leu Arg Val Gln Ile Pro Ile Ile Met Ala
            35                  40                  45

Tyr Lys Asp Asn Pro Ser Leu Asn Lys Asn Arg Asn Pro Val Lys Val
50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
            115                 120                 125

Leu Tyr Asn Phe Pro Gly Ser Asp Gly Ile Ile Asp Cys Pro Leu Leu
        130                 135                 140

Leu Ile Gln Val Thr Arg Leu Thr Cys Gly Gly Phe Ile Leu Ala Leu
145                 150                 155                 160

Arg Leu Asn His Thr Met Ala Asp Ala Ala Gly Leu Leu Leu Phe Leu
```

```
                 165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Ala Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Ala Asn
        435                 440                 445

Asn Leu Arg Ser Thr Ser Gln
    450                 455

<210> SEQ ID NO 8
<211> LENGTH: 455
<212> TYPE: PRT
<213> ORGANISM: Artificial Sequence
<220> FEATURE:
<223> OTHER INFORMATION: Quadruple mutant and 5 cysteine substituted
      apple AAT (pAAT151)

<400> SEQUENCE: 8

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Ile Met Ala
        35                  40                  45

Tyr Lys Asp Asn Pro Ser Leu Asn Lys Asn Arg Asn Pro Val Lys Val
    50                  55                  60
```

Ile Arg Glu Ala Leu Ser Arg Ala Leu Val Tyr Tyr Pro Leu Ala
 65                  70                  75                  80

Gly Arg Leu Arg Glu Gly Pro Asn Arg Lys Leu Val Val Asp Cys Asn
                 85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
130                 135                 140

Leu Ile Gln Val Thr Ala Leu Thr Cys Gly Gly Phe Ile Leu Ala Leu
145                 150                 155                 160

Arg Leu Asn His Thr Met Cys Asp Ala Ala Gly Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Ala Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365

Ser Tyr Leu Ile Val Ser Asp Asn Thr Arg Val Gly Phe Gly Asp Val
370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Ala Asn
        435                 440                 445

Asn Leu Arg Ser Thr Ser Gln
450                 455

<210> SEQ ID NO 9
<211> LENGTH: 455
<212> TYPE: PRT

<213> ORGANISM: Artificial Sequence
<220> FEATURE:
<223> OTHER INFORMATION: Quadruple mutant and 4 cysteine substituted
      apple AAT (pATM017)

<400> SEQUENCE: 9

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Met Ala
        35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Pro Leu Ala
65              70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
130                 135                 140

Leu Ile Gln Val Thr Cys Leu Thr Cys Gly Gly Phe Ile Leu Ala Leu
145                 150                 155                 160

Arg Leu Asn His Thr Met Cys Asp Ala Ala Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Ala Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365

Ser Tyr Leu Ile Val Ser Asp Asn Thr Arg Val Gly Phe Gly Asp Val
370                 375                 380

```
Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
            405                 410                 415

Ile Leu Val Pro Met Cys Leu Pro Ser Ser Ala Met Glu Arg Phe Gln
        420                 425                 430

Gln Glu Leu Glu Arg Ile Thr Gln Glu Pro Lys Glu Asp Ile Ala Asn
    435                 440                 445

Asn Leu Arg Ser Thr Ser Gln
    450                 455

<210> SEQ ID NO 10
<211> LENGTH: 455
<212> TYPE: PRT
<213> ORGANISM: Artificial Sequence
<220> FEATURE:
<223> OTHER INFORMATION: Quadruple mutant and 4 cysteine substituted
      apple AAT (pATM018)

<400> SEQUENCE: 10

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Met Ala
        35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
130                 135                 140

Leu Ile Gln Val Thr Ala Leu Thr Cys Gly Gly Phe Ile Leu Ala Leu
145                 150                 155                 160

Arg Leu Asn His Thr Met Cys Asp Ala Ala Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Ala Arg Thr Leu Ala Leu Asn Ile Asn Pro Lys Glu Ala Val Arg
        275                 280                 285
```

```
Val Ser Cys Ile Val Asn Ala Arg Gly Lys His Asn Val Arg Leu
        290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Cys Asn
        435                 440                 445

Asn Leu Arg Ser Thr Ser Gln
    450                 455

<210> SEQ ID NO 11
<211> LENGTH: 455
<212> TYPE: PRT
<213> ORGANISM: Artificial Sequence
<220> FEATURE:
<223> OTHER INFORMATION: Quadruple mutant and 4 cysteine substituted
      apple AAT (pATM019)

<400> SEQUENCE: 11

Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Met Cys
        35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Ala Leu Thr Cys Gly Gly Phe Ile Leu Ala Leu
145                 150                 155                 160

Arg Leu Asn His Thr Met Cys Asp Ala Ala Gly Leu Leu Leu Phe Leu
                165                 170                 175

Thr Ala Ile Ala Glu Met Ala Arg Gly Ala His Ala Pro Ser Ile Leu
```

```
            180                 185                 190
Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Ala Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Ala Asn
        435                 440                 445

Asn Leu Arg Ser Thr Ser Gln
    450                 455

<210> SEQ ID NO 12
<211> LENGTH: 459
<212> TYPE: PRT
<213> ORGANISM: Malus domestica

<400> SEQUENCE: 12

Met Met Pro Phe Ser Val Leu Gln Val Lys Arg Leu Gln Leu Glu Leu
1               5                   10                  15

Ile Thr Pro Ala Lys Pro Thr Leu Gln Glu Ala Lys Phe Leu Ser Asp
            20                  25                  30

Ile Asp Asp Gln Glu Gly Leu Arg Phe Gln Val Pro Ile Met Cys
        35                  40                  45

Tyr Lys Asp Asn Pro Ser Leu Asn Lys Asn Cys Asn Pro Val Lys Val
    50                  55                  60

Ile Arg Glu Ala Leu Ser Arg Ala Leu Val Tyr Tyr Pro Leu Ala
65                  70                  75                  80

Gly Arg Leu Lys Glu Gly Pro Asn Arg Lys Leu Met Val Asp Cys Asn
                85                  90                  95
```

Gly Glu Gly Ile Leu Phe Val Glu Ala Ser Ala Asp Val Thr Leu Glu
            100                 105                 110

Gln Leu Gly Asp Lys Ile Leu Pro Pro Cys Pro Leu Leu Glu Glu Phe
        115                 120                 125

Leu Phe Asn Phe Pro Gly Ser Asp Gly Ile Ile Gly Cys Pro Leu Leu
    130                 135                 140

Leu Val Gln Val Thr Cys Leu Thr Cys Gly Gly Phe Ile Leu Ala Leu
145                 150                 155                 160

Arg Val Asn His Thr Met Cys Asp Ala Pro Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ser Arg Asp Pro Pro Arg Ile
        195                 200                 205

Thr Cys Ala His His Glu Tyr Glu Asp Val Ile Asp His Ser Asp Gly
    210                 215                 220

Leu Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Gln Tyr Ser Ser Thr Gly
        355                 360                 365

Ser Tyr Leu Ile Val Ser Asp Asn Thr Arg Ala Gly Phe Gly Asp Val
    370                 375                 380

Asn Phe Gly Trp Gly Gln Pro Val Phe Ala Gly Pro Ala Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Cys Asn
        435                 440                 445

Asn Leu Arg Ser Thr Arg Ile Met Ser Met Met
    450                 455

<210> SEQ ID NO 13
<211> LENGTH: 455
<212> TYPE: PRT
<213> ORGANISM: Artificial Sequence
<220> FEATURE:
<223> OTHER INFORMATION: Quadruple mutant and 4 cysteine substituted
      apple AAT (pATM021)

<400> SEQUENCE: 13

-continued

```
Met Lys Ser Phe Ser Val Leu Gln Val Lys Arg Leu Gln Pro Glu Leu
1               5                   10                  15

Ile Thr Pro Ala Lys Ser Thr Pro Gln Glu Thr Lys Phe Leu Ser Asp
            20                  25                  30

Ile Asp Asp Gln Glu Ser Leu Arg Val Gln Ile Pro Ile Ile Met Ala
        35                  40                  45

Tyr Lys Asp Asn Pro Ser Leu Asn Lys Asn Arg Asn Pro Val Lys Val
    50                  55                  60

Ile Arg Glu Ala Leu Ser Arg Ala Leu Val Tyr Tyr Pro Leu Ala
65                  70                  75                  80

Gly Arg Leu Arg Glu Gly Pro Asn Arg Lys Leu Val Val Asp Cys Asn
                85                  90                  95

Gly Glu Gly Ile Leu Phe Val Glu Ala Ser Ala Asp Val Thr Leu Glu
            100                 105                 110

Gln Leu Gly Asp Gln Ile Leu Pro Pro Cys Pro Leu Leu Glu Glu Phe
        115                 120                 125

Leu Tyr Asn Phe Pro Gly Ser Asp Gly Ile Ile Asp Cys Pro Leu Leu
    130                 135                 140

Leu Ile Gln Val Thr Ala Leu Thr Cys Gly Gly Phe Ile Leu Ala Leu
145                 150                 155                 160

Arg Leu Asn His Thr Met Cys Asp Ala Ala Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Gly His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Ala Leu Arg Lys Gln Ile Pro Pro His
                245                 250                 255

Leu Ile Ser Thr Cys Ser Thr Phe Asp Leu Ile Thr Ala Ala Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Lys Tyr Ser Ser Thr Gly
        355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415
```

Ile Leu Val Pro Met Cys Leu Pro Ser Ser Ala Met Glu Arg Phe Gln
    420                 425                 430

Gln Glu Leu Glu Arg Ile Thr Gln Glu Pro Lys Glu Asp Ile Ala Asn
    435                 440                 445

Asn Leu Arg Ser Thr Ser Gln
    450                 455

<210> SEQ ID NO 14
<211> LENGTH: 1368
<212> TYPE: DNA
<213> ORGANISM: Artificial Sequence
<220> FEATURE:
<223> OTHER INFORMATION: Apple AAT gene having optimized codons for
      E.coli

<400> SEQUENCE: 14

| | |
|---|---|
| atgatgagct tttctgtact ccaagtcaaa cgcctgcaac cagaactgat tacgccagcg | 60 |
| aaatcgaccc cgcaggaaac caaattcctg tctgacatcg atgaccaaga gagcttgcgt | 120 |
| gtgcagattc cgatcatcat gtgctataaa gacaacccga gcctgaataa gaatcgcaat | 180 |
| ccggttaagg ccattcgtga ggccctgtcc cgtgcgctgg tttactatta cccgctggcg | 240 |
| ggtcgtctgc gtgagggtcc gaatcgcaaa ctggtggtgg actgcaatgg tgagggtatt | 300 |
| ctgtttgttg aggcgagcgc ggacgtcacc ctggaacagc tgggcgacaa gatcctgccg | 360 |
| ccgtgtccgc tgttggaaga gtttctgtac aacttcccgg cagcgatgg tatcatcgat | 420 |
| tgcccgctgc tgctgattca agtcacttgt ctgacgtgtg gtggctttat tctggctctg | 480 |
| cgcctgaacc acaccatgtg tgatgcagcg ggtttgttgc tgttcctgac cgccatcgca | 540 |
| gagatggccc gtggtgccca cgcaccgagc attctgccgg tgtgggaacg tgaactgctg | 600 |
| ttcgcacgtg acccgcctcg tattacttgc gcgcaccatg aatacgagga cgttatcggc | 660 |
| catagcgacg gcagctacgc gagcagcaac caaagcaata tggtgcagcg tagcttttac | 720 |
| ttcggcgcga agaaaatgcg tgttctgcgc aagcagatcc cgcctcacct gatcagcacg | 780 |
| tgcagcacct tgatttgat taccgcatgc ctgtggaagt gccgtacgct ggcgctgaac | 840 |
| atcaacccga agaagccgt ccgtgtgagc tgtatcgtta cgcgcgtgg taaacacaac | 900 |
| aatgttcgcc tgccgctggg ctattacggc aatgcgttcg cattcccggc tgctatctct | 960 |
| aaggcagagc cgctgtgtaa gaaccctctg ggttacgccc tggagttggt gaagaaggcg | 1020 |
| aaagcgacca tgaatgaaga gtatctgcgc agcgtggcgg atctgctggt tttgcgcggt | 1080 |
| cgtccgcaat actccagcac gggttcctat ctgattgtga cgacaatac ccgcgtgggt | 1140 |
| tttggtgatg tcaacttcgg ttggggccag ccagtctttg ctggcccggt caaagcattg | 1200 |
| gacctgatta gcttctatgt tcaacataag aacaacacgg aagatggtat cttggttccg | 1260 |
| atgtgcctgc cgtcctcggc gatggagcgt ttccaacagg agctggagcg cattacccag | 1320 |
| gaaccgaaag aggatatttg caacaatctg cgtagcacca gccagtaa | 1368 |

<210> SEQ ID NO 15
<211> LENGTH: 47
<212> TYPE: DNA
<213> ORGANISM: Artificial Sequence
<220> FEATURE:
<223> OTHER INFORMATION: Primer MMA-156

<400> SEQUENCE: 15
cacaggaaac agaccatggt gagctttttct gtactccaag tcaaacg    47

```
<210> SEQ ID NO 16
<211> LENGTH: 43
<212> TYPE: DNA
<213> ORGANISM: Artificial Sequence
<220> FEATURE:
<223> OTHER INFORMATION: Primer MMA-163

<400> SEQUENCE: 16
gccaagcttg catgcctgca ggttactggc tggtgctacg cag                    43

<210> SEQ ID NO 17
<211> LENGTH: 42
<212> TYPE: DNA
<213> ORGANISM: Artificial Sequence
<220> FEATURE:
<223> OTHER INFORMATION: Primer MMA-166

<400> SEQUENCE: 17
cacaggaaac agaccatgaa aagcttttct gtactccaag tc                     42

<210> SEQ ID NO 18
<211> LENGTH: 34
<212> TYPE: DNA
<213> ORGANISM: Artificial Sequence
<220> FEATURE:
<223> OTHER INFORMATION: Primer MMA-169

<400> SEQUENCE: 18
cgatgatacc atcgctgccc gggaagttgt acag                              34

<210> SEQ ID NO 19
<211> LENGTH: 32
<212> TYPE: DNA
<213> ORGANISM: Artificial Sequence
<220> FEATURE:
<223> OTHER INFORMATION: Primer MMA-185

<400> SEQUENCE: 19
ggatcatgaa aagcttttct gtactccaag tc                                32

<210> SEQ ID NO 20
<211> LENGTH: 44
<212> TYPE: DNA
<213> ORGANISM: Artificial Sequence
<220> FEATURE:
<223> OTHER INFORMATION: Primer MMA-157

<400> SEQUENCE: 20 gtgattttt tctccgcact agtctactgg ctggtgctac gcag                    44

<210> SEQ ID NO 21
<211> LENGTH: 27
<212> TYPE: DNA
<213> ORGANISM: Artificial Sequence
<220> FEATURE:
<223> OTHER INFORMATION: Primer MMA-152

<400> SEQUENCE: 21
gcccccgttt tcacgatggg caaatat                                      27

<210> SEQ ID NO 22
<211> LENGTH: 27
<212> TYPE: DNA
<213> ORGANISM: Artificial Sequence
<220> FEATURE:
<223> OTHER INFORMATION: Primer MMA-153
```

<400> SEQUENCE: 22
atatttgccc atcgtgaaaa cgggggc                                    27

<210> SEQ ID NO 23
<211> LENGTH: 47
<212> TYPE: DNA
<213> ORGANISM: Artificial Sequence
<220> FEATURE:
<223> OTHER INFORMATION: Primer MMA-156

<400> SEQUENCE: 23
cacaggaaac agaccatggt gagcttttct gtactccaag tcaaacg              47

<210> SEQ ID NO 24
<211> LENGTH: 44
<212> TYPE: DNA
<213> ORGANISM: Artificial Sequence
<220> FEATURE:
<223> OTHER INFORMATION: Primer MMA-157

<400> SEQUENCE: 24 gtgattttttt tctccgcact agtctactgg ctggtgctac gcag                44

<210> SEQ ID NO 25
<211> LENGTH: 44
<212> TYPE: DNA
<213> ORGANISM: Artificial Sequence
<220> FEATURE:
<223> OTHER INFORMATION: Primer MMA-159

<400> SEQUENCE: 25
ctgcgtagca ccagccagta gactagtgcg gagaaaaaaa tcac                 44

<210> SEQ ID NO 26
<211> LENGTH: 47
<212> TYPE: DNA
<213> ORGANISM: Artificial Sequence
<220> FEATURE:
<223> OTHER INFORMATION: Primer MMA-160

<400> SEQUENCE: 26
gccaagcttg catgcctgca ggttacgccc cgccctgcca ctcatcg              47

<210> SEQ ID NO 27
<211> LENGTH: 29
<212> TYPE: DNA
<213> ORGANISM: Artificial Sequence
<220> FEATURE:
<223> OTHER INFORMATION: Primer MMA-207

<400> SEQUENCE: 27
gcgcggtcgt ccgaaatact ccagcacgg                                  29

<210> SEQ ID NO 28
<211> LENGTH: 29
<212> TYPE: DNA
<213> ORGANISM: Artificial Sequence
<220> FEATURE:
<223> OTHER INFORMATION: Primer MMA-208

<400> SEQUENCE: 28
ccgtgctgga gtatttcgga cgaccgcgc                                  29

<210> SEQ ID NO 29
<211> LENGTH: 30

<212> TYPE: DNA
<213> ORGANISM: Artificial Sequence
<220> FEATURE:
<223> OTHER INFORMATION: Primer MMA-215

<400> SEQUENCE: 29
gaacagctgg gcgaccagat cctgccgccg                                       30

<210> SEQ ID NO 30
<211> LENGTH: 30
<212> TYPE: DNA
<213> ORGANISM: Artificial Sequence
<220> FEATURE:
<223> OTHER INFORMATION: Primer MMA-216

<400> SEQUENCE: 30
cggcggcagg atctggtcgc ccagctgttc                                       30

<210> SEQ ID NO 31
<211> LENGTH: 30
<212> TYPE: DNA
<213> ORGANISM: Artificial Sequence
<220> FEATURE:
<223> OTHER INFORMATION: Primer MMA-217

<400> SEQUENCE: 31
aatccggtta aggtcattcg tgaggccctg                                       30

<210> SEQ ID NO 32
<211> LENGTH: 30
<212> TYPE: DNA
<213> ORGANISM: Artificial Sequence
<220> FEATURE:
<223> OTHER INFORMATION: Primer MMA-218

<400> SEQUENCE: 32
cagggcctca cgaatgacct taaccggatt                                       30

<210> SEQ ID NO 33
<211> LENGTH: 30
<212> TYPE: DNA
<213> ORGANISM: Artificial Sequence
<220> FEATURE:
<223> OTHER INFORMATION: Primer MMA-219

<400> SEQUENCE: 33
cgttaacgcg cgtgataaac acaacaatgt                                       30

<210> SEQ ID NO 34
<211> LENGTH: 30
<212> TYPE: DNA
<213> ORGANISM: Artificial Sequence
<220> FEATURE:
<223> OTHER INFORMATION: Primer MMA-220

<400> SEQUENCE: 34
acattgttgt gtttatcacg cgcgttaacg                                       30

<210> SEQ ID NO 35
<211> LENGTH: 30
<212> TYPE: DNA
<213> ORGANISM: Artificial Sequence
<220> FEATURE:
<223> OTHER INFORMATION: Primer MMA-221

<400> SEQUENCE: 35
agaacaacac ggaaaatggt atcttggttc                                            30

<210> SEQ ID NO 36
<211> LENGTH: 30
<212> TYPE: DNA
<213> ORGANISM: Artificial Sequence
<220> FEATURE:
<223> OTHER INFORMATION: Primer MMA-222

<400> SEQUENCE: 36
gaaccaagat accatttcc gtgttgttct                                             30

<210> SEQ ID NO 37
<211> LENGTH: 30
<212> TYPE: DNA
<213> ORGANISM: Artificial Sequence
<220> FEATURE:
<223> OTHER INFORMATION: Primer MMA-223

<400> SEQUENCE: 37
gcgaaagaaa tgcgtgctct gcgcaagcag                                            30

<210> SEQ ID NO 38
<211> LENGTH: 30
<212> TYPE: DNA
<213> ORGANISM: Artificial Sequence
<220> FEATURE:
<223> OTHER INFORMATION: Primer MMA-224

<400> SEQUENCE: 38
ctgcttgcgc agagcacgca tttctttcgc                                            30

<210> SEQ ID NO 39
<211> LENGTH: 30
<212> TYPE: DNA
<213> ORGANISM: Artificial Sequence
<220> FEATURE:
<223> OTHER INFORMATION: Primer MMA-225

<400> SEQUENCE: 39
agcttctatg ttcaccataa gaacaacacg                                            30

<210> SEQ ID NO 40
<211> LENGTH: 30
<212> TYPE: DNA
<213> ORGANISM: Artificial Sequence
<220> FEATURE:
<223> OTHER INFORMATION: Primer MMA-226

<400> SEQUENCE: 40
cgtgttgttc ttatggtgaa catagaagct                                            30

<210> SEQ ID NO 41
<211> LENGTH: 30
<212> TYPE: DNA
<213> ORGANISM: Artificial Sequence
<220> FEATURE:
<223> OTHER INFORMATION: Primer MMA-241

<400> SEQUENCE: 41
agaccatgaa aagcctttct gtactccaag                                            30

<210> SEQ ID NO 42
<211> LENGTH: 30
<212> TYPE: DNA
<213> ORGANISM: Artificial Sequence
<220> FEATURE:
<223> OTHER INFORMATION: Primer MMA-243

<400> SEQUENCE: 42
cttggagtac agaaaggctt ttcatggtct                                30

<210> SEQ ID NO 43
<211> LENGTH: 30
<212> TYPE: DNA
<213> ORGANISM: Artificial Sequence
<220> FEATURE:
<223> OTHER INFORMATION: Primer MMA-243

<400> SEQUENCE: 43
gaaaagcttt tctgtattcc aagtcaaacg                                30

<210> SEQ ID NO 44
<211> LENGTH: 30
<212> TYPE: DNA
<213> ORGANISM: Artificial Sequence
<220> FEATURE:
<223> OTHER INFORMATION: Primer MMA-244

<400> SEQUENCE: 44
cgtttgactt ggaatacaga aaagcttttc                                30

<210> SEQ ID NO 45
<211> LENGTH: 30
<212> TYPE: DNA
<213> ORGANISM: Artificial Sequence
<220> FEATURE:
<223> OTHER INFORMATION: Primer MMA-229

<400> SEQUENCE: 45
tacgaggacg ttatcgacca tagcgacggc                                30

<210> SEQ ID NO 46
<211> LENGTH: 30
<212> TYPE: DNA
<213> ORGANISM: Artificial Sequence
<220> FEATURE:
<223> OTHER INFORMATION: Primer MMA-230

<400> SEQUENCE: 46
gccgtcgcta tggtcgataa cgtcctcgta                                30

<210> SEQ ID NO 47
<211> LENGTH: 30
<212> TYPE: DNA
<213> ORGANISM: Artificial Sequence
<220> FEATURE:
<223> OTHER INFORMATION: Primer MMA-231

<400> SEQUENCE: 47
atgttcaaca taagagcaac acggaagatg                                30

<210> SEQ ID NO 48
<211> LENGTH: 30
<212> TYPE: DNA
<213> ORGANISM: Artificial Sequence
<220> FEATURE:
<223> OTHER INFORMATION: Primer MMA-232

<400> SEQUENCE: 48
catcttccgt gttgctctta tgttgaacat                                30

```
<210> SEQ ID NO 49
<211> LENGTH: 30
<212> TYPE: DNA
<213> ORGANISM: Artificial Sequence
<220> FEATURE:
<223> OTHER INFORMATION: Primer MMA-245

<400> SEQUENCE: 49
aacagaccat gaaaggcttt tctgtactcc                                30

<210> SEQ ID NO 50
<211> LENGTH: 30
<212> TYPE: DNA
<213> ORGANISM: Artificial Sequence
<220> FEATURE:
<223> OTHER INFORMATION: Primer MMA-246

<400> SEQUENCE: 50
ggagtacaga aaagcctttc atggtctgtt                                30

<210> SEQ ID NO 51
<211> LENGTH: 30
<212> TYPE: DNA
<213> ORGANISM: Artificial Sequence
<220> FEATURE:
<223> OTHER INFORMATION: Primer MMA-233

<400> SEQUENCE: 51
tggagcgcat tacccacgaa ccgaaagagg                                30

<210> SEQ ID NO 52
<211> LENGTH: 30
<212> TYPE: DNA
<213> ORGANISM: Artificial Sequence
<220> FEATURE:
<223> OTHER INFORMATION: Primer MMA-234

<400> SEQUENCE: 52
cctctttcgg ttcgtgggta atgcgctcca                                30

<210> SEQ ID NO 53
<211> LENGTH: 30
<212> TYPE: DNA
<213> ORGANISM: Artificial Sequence
<220> FEATURE:
<223> OTHER INFORMATION: Primer MMA-239

<400> SEQUENCE: 53
cgtctgcgtg agggtcggaa tcgcaaactg                                30

<210> SEQ ID NO 54
<211> LENGTH: 30
<212> TYPE: DNA
<213> ORGANISM: Artificial Sequence
<220> FEATURE:
<223> OTHER INFORMATION: Primer MMA-240

<400> SEQUENCE: 54
cagtttgcga ttccgaccct cacgcagacg                                30

<210> SEQ ID NO 55
<211> LENGTH: 30
<212> TYPE: DNA
<213> ORGANISM: Artificial Sequence
<220> FEATURE:
<223> OTHER INFORMATION: Primer MMA-237
```

-continued

<400> SEQUENCE: 55
cgcgagcagc aacgaaagca atatggtgca                                      30

<210> SEQ ID NO 56
<211> LENGTH: 30
<212> TYPE: DNA
<213> ORGANISM: Artificial Sequence
<220> FEATURE:
<223> OTHER INFORMATION: Primer MMA-238

<400> SEQUENCE: 56
tgcaccatat tgctttcgtt gctgctcgcg                                      30

<210> SEQ ID NO 57
<211> LENGTH: 30
<212> TYPE: DNA
<213> ORGANISM: Artificial Sequence
<220> FEATURE:
<223> OTHER INFORMATION: Primer MMA-235

<400> SEQUENCE: 57
gagcagcaac caaaacaata tggtgcagcg                                      30

<210> SEQ ID NO 58
<211> LENGTH: 30
<212> TYPE: DNA
<213> ORGANISM: Artificial Sequence
<220> FEATURE:
<223> OTHER INFORMATION: Primer MMA-236

<400> SEQUENCE: 58
cgctgcacca tattgttttg gttgctgctc                                      30

<210> SEQ ID NO 59
<211> LENGTH: 32
<212> TYPE: DNA
<213> ORGANISM: Artificial Sequence
<220> FEATURE:
<223> OTHER INFORMATION: Primer MMA-380

<400> SEQUENCE: 59
ctgattcaag tcactcgtct gacgtgtggt gg                                   32

<210> SEQ ID NO 60
<211> LENGTH: 32
<212> TYPE: DNA
<213> ORGANISM: Artificial Sequence
<220> FEATURE:
<223> OTHER INFORMATION: Primer MMA-381

<400> SEQUENCE: 60
ccaccacacg tcagacgagt gacttgaatc ag                                   32

<210> SEQ ID NO 61
<211> LENGTH: 454
<212> TYPE: PRT
<213> ORGANISM: Pyrus x bretschneideri

<400> SEQUENCE: 61

Met Met Pro Pro Ser Val Leu Gln Val Lys Arg Leu Gln Pro Glu Leu
1               5                   10                  15

Ile Thr Pro Ala Lys Pro Thr Pro Gln Glu Thr Lys Phe Leu Ser Asp
            20                  25                  30

```
Ile Asp Asp Gln Glu Gly Leu Arg Phe Gln Val Pro Val Ile Met Cys
         35                  40                  45

Tyr Lys Asp Asn Pro Ser Leu Asn Glu Asn Arg Asn Pro Val Lys Val
 50                  55                  60

Ile Arg Glu Ala Leu Ser Arg Ala Leu Val Tyr Tyr Pro Leu Ala
 65                  70                  75                  80

Gly Arg Leu Arg Glu Gly Pro Asn Arg Lys Leu Met Val Asp Cys Asn
                 85                  90                  95

Gly Glu Gly Ile Leu Phe Val Glu Ala Ser Ala Asp Val Thr Leu Glu
                100                 105                 110

Gln Leu Gly Asp Lys Ile Leu Pro Pro Cys Pro Leu Leu Asp Glu Phe
                115                 120                 125

Leu Phe Asn Phe Pro Gly Ser Asp Gly Ile Ile Gly Cys Pro Leu Leu
130                 135                 140

Leu Val Gln Val Thr Cys Leu Thr Cys Gly Gly Phe Ile Leu Ala Leu
145                 150                 155                 160

Cys Leu Asn His Thr Met Cys Asp Ala Ala Gly Leu Leu Leu Phe Leu
                165                 170                 175

Thr Ala Val Ala Glu Met Ala Lys Gly Ala His Ala Pro Ser Ile Leu
                180                 185                 190

Pro Val Trp Glu Arg Glu Phe Leu Phe Ala Arg Asp Pro Pro Arg Ile
                195                 200                 205

Thr Cys Ala His His Glu Tyr Glu Asp Val Ile Asp His Ser Asn Gly
                210                 215                 220

Ser Tyr Pro Ser Ser Asn Gln Ser Asn Met Val Gln Gln Ser Phe Tyr
225                 230                 235                 240

Phe Gly Ala Lys Glu Met Arg Val Leu Arg Lys Gln Ile Pro Pro Gln
                245                 250                 255

Leu Ile Ser Thr Cys Ser Thr Phe Asp Leu Ile Thr Ala Cys Leu Trp
                260                 265                 270

Lys Cys Arg Thr Leu Ala Leu Lys Ile Asn Pro Lys Gln Ala Val Arg
                275                 280                 285

Ile Ser Cys Ile Val Asn Ala Arg Gly Lys His His Asn Val His Leu
290                 295                 300

Pro Leu Gly Tyr Tyr Gly Asn Ala Phe Ala Phe Pro Ala Ala Val Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
                340                 345                 350

Ala Asp Leu Met Val Leu Arg Gly Arg Pro Gln Tyr Ser Ser Thr Gly
                355                 360                 365

Ser Tyr Phe Ile Val Ser Asp Asn Thr Arg Ala Gly Phe Gly Asp Val
370                 375                 380

Asp Phe Gly Trp Gly Gln Pro Val Phe Ala Gly Pro Ala Lys Ala Leu
385                 390                 395                 400

Asp Leu Ile Ser Phe Tyr Val Gln His Lys Lys Asp Thr Glu Asp Gly
                405                 410                 415

Ile Leu Val Pro Met Cys Leu Pro Phe Ser Ala Met Glu Arg Phe Gln
                420                 425                 430

Val Val Ser Leu Gly Thr Asn Pro Arg Val Met Pro Val Ile Glu Arg
                435                 440                 445

Ser Glu Cys Tyr Tyr Lys
```

-continued

```
<210> SEQ ID NO 62
<211> LENGTH: 459
<212> TYPE: PRT
<213> ORGANISM: Eriobotrya japonica
<220> FEATURE:
<221> NAME/KEY: misc_feature
<222> LOCATION: (228)..(228)
<223> OTHER INFORMATION: Xaa can be any naturally occurring amino acid

<400> SEQUENCE: 62
```

| | | | | | | | | | | | | | | |
|---|---|---|---|---|---|---|---|---|---|---|---|---|---|---|
| Met | Met | Pro | Leu | Ser | Val | Leu | Gln | Val | Lys | Arg | Leu | Gln | Pro | Glu | Phe |
| 1 | | | | 5 | | | | | 10 | | | | | 15 | |
| Ile | Thr | Pro | Ala | Lys | Pro | Met | Pro | Gln | Glu | Thr | Lys | Phe | Leu | Ser | Asp |
| | | | 20 | | | | | 25 | | | | | 30 | | |
| Ile | Asp | Asp | Gln | Glu | Gly | Leu | Arg | Phe | His | Val | Pro | Val | Ile | Met | Cys |
| | | 35 | | | | | 40 | | | | | 45 | | | |
| Tyr | Lys | Asp | Asn | Pro | Ser | Leu | Asn | Glu | Asn | Arg | Asn | Pro | Val | Lys | Val |
| 50 | | | | | 55 | | | | | 60 | | | | | |
| Ile | Arg | Glu | Ala | Val | Ser | Arg | Ala | Leu | Val | Tyr | Tyr | Pro | Leu | Ala | |
| 65 | | | | | 70 | | | | | 75 | | | | | 80 |
| Gly | Arg | Leu | Arg | Glu | Trp | Pro | Asn | Arg | Lys | Leu | Val | Val | Asp | Cys | Asn |
| | | | | 85 | | | | | 90 | | | | | 95 | |
| Ser | Glu | Gly | Ile | Leu | Phe | Val | Glu | Ala | Phe | Ala | Asn | Val | Thr | Leu | Glu |
| | | | 100 | | | | | 105 | | | | | 110 | | |
| Gln | Leu | Gly | Asp | Lys | Ile | Leu | Pro | Pro | Cys | Pro | Leu | Leu | Glu | Glu | Phe |
| | | 115 | | | | | 120 | | | | | 125 | | | |
| Leu | Phe | Asn | Val | Pro | Gly | Ser | Asp | Gly | Ile | Ile | Gly | Cys | Pro | Leu | Leu |
| 130 | | | | | 135 | | | | | 140 | | | | | |
| Leu | Val | Gln | Val | Thr | Cys | Leu | Thr | Cys | Gly | Gly | Phe | Ile | Leu | Ala | Leu |
| 145 | | | | | 150 | | | | | 155 | | | | | 160 |
| Arg | Leu | Asn | His | Thr | Met | Cys | Asp | Ala | Pro | Gly | Leu | Val | Leu | Phe | Leu |
| | | | | 165 | | | | | 170 | | | | | 175 | |
| Thr | Ala | Ile | Ala | Glu | Met | Ala | Ser | Gly | Ala | His | Ala | Pro | Ser | Ile | Leu |
| | | | 180 | | | | | 185 | | | | | 190 | | |
| Pro | Val | Trp | Glu | Arg | Glu | Leu | Leu | Phe | Ala | Arg | Asp | Pro | Arg | Ile | |
| | | 195 | | | | | 200 | | | | | 205 | | | |
| Thr | Cys | Ala | His | His | Glu | Tyr | Glu | Asp | Val | Ile | Asp | His | Ser | Asp | Gly |
| 210 | | | | | 215 | | | | | 220 | | | | | |
| Ser | Tyr | Ala | Xaa | Ser | Asn | Gln | Ser | Asn | Met | Val | Gln | Arg | Ser | Phe | Tyr |
| 225 | | | | | 230 | | | | | 235 | | | | | 240 |
| Phe | Gly | Ala | Lys | Glu | Met | Arg | Val | Leu | Arg | Lys | Gln | Ile | Pro | Pro | His |
| | | | | 245 | | | | | 250 | | | | | 255 | |
| Leu | Ile | Ser | Thr | Cys | Ser | Thr | Phe | Asp | Leu | Ile | Thr | Ala | Cys | Leu | Trp |
| | | | 260 | | | | | 265 | | | | | 270 | | |
| Lys | Cys | His | Thr | Leu | Ala | Leu | Lys | Ile | Asn | Pro | Lys | Gln | Val | Val | Gln |
| | | 275 | | | | | 280 | | | | | 285 | | | |
| Val | Ser | Phe | Thr | Val | Asn | Ala | Arg | Gly | Lys | His | His | Asn | Val | Arg | Leu |
| 290 | | | | | 295 | | | | | 300 | | | | | |
| Pro | Leu | Gly | Tyr | Tyr | Gly | Asn | Ala | Phe | Ala | Phe | Pro | Ala | Ala | Val | Ser |
| 305 | | | | | 310 | | | | | 315 | | | | | 320 |
| Lys | Ala | Glu | Pro | Leu | Cys | Lys | Asn | Pro | Leu | Gly | Tyr | Ala | Leu | Glu | Leu |
| | | | | 325 | | | | | 330 | | | | | 335 | |
| Val | Lys | Lys | Ala | Lys | Ala | Thr | Met | Asn | Glu | Glu | Tyr | Leu | Arg | Ser | Val |
| | | | 340 | | | | | 345 | | | | | 350 | | |

```
Ala Asp Leu Leu Val Leu Arg Gly Arg Pro Gln Tyr Leu Tyr Thr Gly
        355                 360                 365

Ser Tyr Phe Ile Val Ser Asp Asn Thr Arg Ala Gly Phe Gly Asp Val
    370                 375                 380

Asn Phe Gly Trp Gly Gln Pro Val Phe Ala Gly Pro Ala Lys Ala Val
385                 390                 395                 400

Asp Leu Phe Arg Phe Tyr Val Gln His Lys Asn Asn Thr Glu Asp Gly
            405                 410                 415

Ile Leu Val Pro Met Cys Leu Pro Ser Ser Ala Met Glu Arg Phe Gln
                420                 425                 430

Gln Glu Leu Glu Arg Ile Thr Gln Glu Pro Lys Glu Asp Ile Cys Asn
        435                 440                 445

Asn Leu Arg Ser Thr Arg Ile Met Ser Met Met
        450                 455
```

<210> SEQ ID NO 63
<211> LENGTH: 459
<212> TYPE: PRT
<213> ORGANISM: Diospyros kaki

<400> SEQUENCE: 63

```
Met Met Pro Leu Ser Val Leu Gln Val Lys Arg Leu Gln Pro Glu Phe
1               5                   10                  15

Ile Thr Pro Ala Lys Pro Met Pro Gln Glu Thr Lys Phe Leu Ser Asp
                20                  25                  30

Ile Asp Asp Gln Glu Gly Leu Arg Phe His Val Pro Val Ile Met Arg
            35                  40                  45

Tyr Lys Asp Asn Pro Ser Leu Asn Glu Asn Arg Asn Pro Val Lys Val
        50                  55                  60

Ile Arg Glu Ala Val Ser Arg Ala Leu Val Tyr Tyr Pro Leu Ala
65                  70                  75                  80

Gly Arg Leu Arg Glu Trp Pro Asn Arg Lys Leu Val Val Asp Cys Asn
                85                  90                  95

Ser Glu Gly Ile Leu Phe Val Glu Ala Phe Ala Asn Val Thr Leu Glu
                100                 105                 110

Gln Leu Gly Asp Lys Ile Leu Pro Pro Cys Pro Leu Leu Glu Gly Phe
            115                 120                 125

Leu Phe Asn Val Pro Gly Ser Asp Gly Ile Ile Gly Cys Pro Leu Leu
130                 135                 140

Leu Val Gln Val Thr Cys Leu Thr Cys Gly Gly Phe Ile Leu Ala Leu
145                 150                 155                 160

Arg Leu Asn His Thr Met Cys Asp Ala Pro Gly Leu Val Leu Phe Leu
                165                 170                 175

Thr Ala Ile Ala Glu Met Ala Ser Gly Ala His Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His His Glu Tyr Glu Asp Val Ile Asp His Ser Asp Gly
    210                 215                 220

Ser Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Pro Ala Cys Leu Trp
```

```
            260                 265                 270
Lys Cys His Thr Leu Ala Leu Lys Ile Asn Pro Lys Gln Val Val Gln
            275                 280                 285

Val Ser Phe Thr Val Asn Ala Arg Gly Lys His His Asn Val Arg Leu
        290                 295                 300

Pro Leu Gly Tyr Tyr Gly Asn Ala Phe Ala Phe Pro Ala Ala Val Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Gln Tyr Leu Tyr Thr Gly
        355                 360                 365

Ser Tyr Phe Ile Val Ser Asp Asn Thr Arg Ala Gly Phe Gly Asp Val
        370                 375                 380

Asn Phe Gly Trp Gly Gln Pro Val Phe Ala Gly Pro Ala Lys Ala Val
385                 390                 395                 400

Asp Leu Phe Arg Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Cys Asn
                435                 440                 445

Asn Leu Arg Ser Thr Arg Ile Met Ser Met Met
            450                 455

<210> SEQ ID NO 64
<211> LENGTH: 442
<212> TYPE: PRT
<213> ORGANISM: Solanum pennellii

<400> SEQUENCE: 64

Met Lys Asn Thr Leu Pro Ile Ser Ile Asn Tyr His Lys Pro Lys Leu
1               5                   10                  15

Val Val Pro Ser Ser Val Thr Pro His Glu Thr Lys Arg Leu Ser Glu
            20                  25                  30

Ile Asp Asp Gln Gly Phe Ile Arg Phe Gln Ile Pro Ile Leu Met Phe
        35                  40                  45

Tyr Lys Tyr Asn Ser Ser Met Lys Gly Lys Asp Pro Ala Arg Ile Ile
    50                  55                  60

Glu Asp Gly Leu Ser Lys Thr Leu Val Phe Tyr His Pro Leu Ala Gly
65                  70                  75                  80

Arg Leu Ile Glu Gly Pro Asn Lys Lys Leu Met Val Asn Cys Asn Gly
                85                  90                  95

Glu Gly Val Leu Phe Ile Glu Gly Asp Ala Asn Ile Glu Leu Glu Lys
            100                 105                 110

Leu Gly Glu Ser Ile Lys Pro Pro Cys Pro Tyr Leu Asp Leu Leu Leu
        115                 120                 125

His Asn Val Pro Gly Ser Asp Gly Ile Ile Gly Ser Pro Leu Leu Leu
    130                 135                 140

Ile Gln Val Thr Arg Phe Thr Cys Gly Gly Phe Ala Val Gly Phe Arg
145                 150                 155                 160

Val Ser His Thr Met Met Asp Gly Tyr Gly Phe Lys Met Phe Leu Asn
                165                 170                 175
```

```
Ala Leu Ser Glu Leu Ile Gln Gly Ala Ser Thr Pro Ser Ile Leu Pro
            180                 185                 190

Val Trp Gln Arg His Leu Leu Ser Ala Arg Ser Ser Pro Cys Ile Thr
            195                 200                 205

Cys Ser His His Glu Phe Asp Glu Glu Ile Glu Ser Lys Ile Ala Trp
            210                 215                 220

Glu Ser Met Glu Asp Lys Leu Ile Gln Glu Ser Phe Phe Gly Asn
225                 230                 235                 240

Glu Glu Met Glu Val Ile Lys Asn Gln Ile Pro Pro Asn Tyr Gly Cys
                    245                 250                 255

Thr Lys Phe Glu Leu Leu Met Ala Phe Leu Trp Lys Cys Arg Thr Ile
                260                 265                 270

Ala Leu Asp Leu His Pro Glu Glu Ile Val Arg Leu Thr Tyr Val Ile
            275                 280                 285

Asn Ile Arg Gly Lys Lys Ser Leu Asn Ile Glu Leu Pro Ile Gly Tyr
            290                 295                 300

Tyr Gly Asn Ala Phe Val Thr Pro Val Val Ser Lys Ala Gly Leu
305                 310                 315                 320

Leu Cys Ser Asn Pro Val Thr Tyr Ala Val Glu Leu Ile Lys Lys Val
                325                 330                 335

Lys Asp His Ile Asn Glu Glu Tyr Ile Lys Ser Val Ile Asp Leu Thr
            340                 345                 350

Val Ile Lys Gly Arg Pro Glu Leu Thr Lys Ser Trp Asn Phe Leu Val
            355                 360                 365

Ser Asp Asn Arg Tyr Ile Gly Phe Asp Glu Phe Asp Phe Gly Trp Gly
370                 375                 380

Asn Pro Ile Phe Gly Gly Ile Ser Lys Ala Thr Ser Phe Ile Ser Phe
385                 390                 395                 400

Gly Val Ser Val Lys Asn Asp Lys Gly Glu Lys Gly Val Leu Ile Ala
                405                 410                 415

Ile Ser Leu Pro Pro Leu Ala Met Lys Lys Leu Gln Asp Ile Tyr Asn
            420                 425                 430

Met Thr Phe Arg Val Ile Ile Pro Arg Ile
            435                 440

<210> SEQ ID NO 65
<211> LENGTH: 452
<212> TYPE: PRT
<213> ORGANISM: Fragaria x ananassa

<400> SEQUENCE: 65

Met Glu Lys Ile Glu Val Ser Ile Asn Ser Lys His Thr Ile Lys Pro
1                   5                   10                  15

Ser Thr Ser Ser Thr Pro Leu Gln Pro Tyr Lys Leu Thr Leu Leu Asp
            20                  25                  30

Gln Leu Thr Pro Pro Ala Tyr Val Pro Ile Val Phe Phe Tyr Pro Ile
            35                  40                  45

Thr Asp His Asp Phe Asn Leu Pro Gln Thr Leu Ala Asp Leu Arg Gln
        50                  55                  60

Ala Leu Ser Glu Thr Leu Thr Leu Tyr Tyr Pro Leu Ser Gly Arg Val
65                  70                  75                  80

Lys Asn Asn Leu Tyr Ile Asp Asp Phe Glu Glu Gly Val Pro Tyr Leu
                85                  90                  95

Glu Ala Arg Val Asn Cys Asp Met Thr Asp Phe Leu Arg Leu Arg Lys
            100                 105                 110
```

-continued

Ile Glu Cys Leu Asn Glu Phe Val Pro Ile Lys Pro Phe Ser Met Glu
            115                 120                 125

Ala Ile Ser Asp Glu Arg Tyr Pro Leu Leu Gly Val Gln Val Asn Val
        130                 135                 140

Phe Asp Ser Gly Ile Ala Ile Gly Val Ser Val Ser His Lys Leu Ile
145                 150                 155                 160

Asp Gly Gly Thr Ala Asp Cys Phe Leu Lys Ser Trp Gly Ala Val Phe
                165                 170                 175

Arg Gly Cys Arg Glu Asn Ile Ile His Pro Ser Leu Ser Glu Ala Ala
            180                 185                 190

Leu Leu Phe Pro Pro Arg Asp Asp Leu Pro Glu Lys Tyr Val Asp Gln
        195                 200                 205

Met Glu Ala Leu Trp Phe Ala Gly Lys Lys Val Ala Thr Arg Arg Phe
210                 215                 220

Val Phe Gly Val Lys Ala Ile Ser Ser Ile Gln Asp Glu Ala Lys Ser
225                 230                 235                 240

Glu Ser Val Pro Lys Pro Ser Arg Val His Ala Val Thr Gly Phe Leu
                245                 250                 255

Trp Lys His Leu Ile Ala Ala Ser Arg Ala Leu Thr Ser Gly Thr Thr
            260                 265                 270

Ser Thr Arg Leu Ser Ile Ala Ala Gln Ala Val Asn Leu Arg Thr Arg
        275                 280                 285

Met Asn Met Glu Thr Val Leu Asp Asn Ala Thr Gly Asn Leu Phe Trp
290                 295                 300

Trp Ala Gln Ala Ile Leu Glu Leu Ser His Thr Thr Pro Glu Ile Ser
305                 310                 315                 320

Asp Leu Lys Leu Cys Asp Leu Val Asn Leu Asn Gly Ser Val Lys
                325                 330                 335

Gln Cys Asn Gly Asp Tyr Phe Glu Thr Phe Lys Gly Lys Glu Gly Tyr
            340                 345                 350

Gly Arg Met Cys Glu Tyr Leu Asp Phe Gln Arg Thr Met Ser Ser Met
        355                 360                 365

Glu Pro Ala Pro Asp Ile Tyr Leu Phe Ser Ser Trp Thr Asn Phe Phe
370                 375                 380

Asn Pro Leu Asp Phe Gly Trp Gly Arg Thr Ser Trp Ile Gly Val Ala
385                 390                 395                 400

Gly Lys Ile Glu Ser Ala Ser Cys Lys Phe Ile Ile Leu Val Pro Thr
                405                 410                 415

Gln Cys Gly Ser Gly Ile Glu Ala Trp Val Asn Leu Glu Glu Glu Lys
            420                 425                 430

Met Ala Met Leu Glu Gln Asp Pro His Phe Leu Ala Leu Ala Ser Pro
        435                 440                 445

Lys Thr Leu Ile
    450

<210> SEQ ID NO 66
<211> LENGTH: 442
<212> TYPE: PRT
<213> ORGANISM: Solanum pennellii

<400> SEQUENCE: 66

Met Ala Asn Thr Leu Pro Ile Ser Ile Asn Tyr His Lys Pro Lys Leu
1               5                   10                  15

Val Val Pro Ser Ser Val Thr Pro His Glu Thr Lys Arg Leu Ser Glu

```
                20                  25                  30
Ile Asp Asp Gln Gly Phe Ile Arg Phe Gln Ile Pro Ile Leu Met Phe
            35                  40                  45
Tyr Lys Tyr Asn Ser Ser Met Lys Gly Lys Asp Pro Ala Arg Ile Ile
 50                  55                  60
Glu Asp Gly Leu Ser Lys Thr Leu Val Phe Tyr His Pro Leu Ala Gly
 65                  70                  75                  80
Arg Leu Ile Glu Gly Pro Asn Lys Lys Leu Met Val Asn Cys Asn Gly
                85                  90                  95
Glu Gly Val Leu Phe Ile Glu Gly Asp Ala Asn Ile Glu Leu Glu Lys
                100                 105                 110
Leu Gly Glu Ser Ile Lys Pro Pro Cys Pro Tyr Leu Asp Leu Leu Leu
            115                 120                 125
His Asn Val Pro Gly Ser Asp Gly Ile Ile Gly Ser Pro Leu Leu Leu
            130                 135                 140
Ile Gln Val Thr Arg Phe Thr Cys Gly Gly Phe Ala Val Gly Phe Arg
145                 150                 155                 160
Val Ser His Thr Met Met Asp Gly Tyr Gly Phe Lys Met Phe Leu Asn
                165                 170                 175
Ala Leu Ser Glu Leu Ile Gln Gly Ala Ser Thr Pro Ser Ile Leu Pro
            180                 185                 190
Val Trp Gln Arg His Leu Leu Ser Ala Arg Ser Ser Pro Cys Ile Thr
            195                 200                 205
Cys Ser His His Glu Phe Asp Glu Glu Ile Glu Ser Lys Ile Ala Trp
        210                 215                 220
Glu Ser Met Glu Asp Lys Leu Ile Gln Glu Ser Phe Phe Phe Gly Asn
225                 230                 235                 240
Glu Glu Met Glu Val Ile Lys Asn Gln Ile Pro Pro Asn Tyr Gly Cys
                245                 250                 255
Thr Lys Phe Glu Leu Leu Met Ala Phe Leu Trp Lys Cys Arg Thr Ile
                260                 265                 270
Ala Leu Asp Leu His Pro Glu Glu Ile Val Arg Leu Thr Tyr Val Ile
            275                 280                 285
Asn Ile Arg Gly Lys Lys Ser Leu Asn Ile Glu Leu Pro Ile Gly Tyr
            290                 295                 300
Tyr Gly Asn Ala Phe Val Thr Pro Val Val Ser Lys Ala Gly Leu Leu
305                 310                 315                 320
Leu Cys Ser Asn Pro Val Thr Tyr Ala Val Glu Leu Ile Lys Lys Val
                325                 330                 335
Lys Asp His Ile Asn Glu Glu Tyr Ile Lys Ser Val Ile Asp Leu Thr
                340                 345                 350
Val Ile Lys Gly Arg Pro Glu Leu Thr Lys Ser Trp Asn Phe Leu Val
            355                 360                 365
Ser Asp Asn Arg Tyr Ile Gly Phe Asp Glu Phe Asp Phe Gly Trp Gly
            370                 375                 380
Asn Pro Ile Phe Gly Gly Ile Ser Lys Ala Thr Ser Phe Ile Ser Phe
385                 390                 395                 400
Gly Val Ser Val Lys Asn Asp Lys Gly Glu Lys Gly Val Leu Ile Ala
                405                 410                 415
Ile Ser Leu Pro Pro Leu Ala Met Lys Lys Leu Gln Asp Ile Tyr Asn
            420                 425                 430
Met Thr Phe Arg Val Ile Ile Pro Arg Ile
            435                 440
```

<210> SEQ ID NO 67
<211> LENGTH: 442
<212> TYPE: PRT
<213> ORGANISM: Solanum lycopersicum

<400> SEQUENCE: 67

```
Met Ala Asn Ile Leu Pro Ile Ser Ile Asn Tyr His Lys Pro Lys Leu
1               5                   10                  15

Val Val Pro Ser Ser Val Thr Ser His Glu Thr Lys Arg Leu Ser Glu
            20                  25                  30

Ile Asp Asp Gln Gly Phe Ile Arg Leu Gln Ile Pro Ile Leu Met Phe
        35                  40                  45

Tyr Lys Tyr Asn Ser Ser Met Lys Gly Lys Asp Leu Ala Lys Ile Ile
    50                  55                  60

Lys Asp Gly Leu Ser Lys Thr Leu Val Phe Tyr Tyr Pro Leu Ala Gly
65                  70                  75                  80

Arg Leu Ile Glu Gly Pro Asn Lys Lys Leu Met Val Asn Cys Asn Gly
                85                  90                  95

Glu Gly Val Leu Phe Ile Glu Gly Asp Ala Asn Ile Glu Leu Glu Lys
            100                 105                 110

Leu Gly Glu Ser Ile Lys Pro Pro Cys Pro Tyr Leu Asp Leu Leu Leu
        115                 120                 125

His Asn Val His Gly Ser Asp Gly Ile Ile Gly Ser Pro Leu Leu Leu
    130                 135                 140

Ile Gln Val Thr Arg Phe Thr Cys Gly Gly Phe Ala Val Gly Phe Arg
145                 150                 155                 160

Phe Asn His Thr Met Met Asp Ala Tyr Gly Phe Lys Met Phe Leu Asn
                165                 170                 175

Ala Leu Ser Glu Leu Ile Gln Gly Ala Ser Thr Pro Ser Ile Leu Pro
            180                 185                 190

Val Trp Glu Arg His Leu Leu Ser Ala Arg Ser Pro Ser Ile Thr
        195                 200                 205

Cys Ile His His Glu Phe Asp Glu Glu Ile Glu Ser Lys Ile Ala Trp
210                 215                 220

Glu Ser Met Glu Asp Lys Leu Ile Gln Gln Ser Phe Phe Gly Asn
225                 230                 235                 240

Glu Glu Met Glu Val Ile Lys Asn Gln Val Pro Pro Asn Tyr Glu Cys
                245                 250                 255

Thr Lys Phe Glu Leu Leu Met Ala Phe Leu Trp Lys Cys Arg Thr Ile
            260                 265                 270

Ala Leu Asn Leu His Ser Asp Glu Ile Val Arg Leu Thr Tyr Val Ile
        275                 280                 285

Asn Ile Arg Gly Lys Lys Ser Leu Asn Ile Glu Leu Pro Ile Gly Tyr
    290                 295                 300

Tyr Gly Asn Ala Phe Ile Thr Pro Val Val Ser Lys Ala Gly Leu
305                 310                 315                 320

Leu Cys Ser Asn Pro Val Thr Tyr Ala Val Glu Leu Ile Lys Lys Val
                325                 330                 335

Lys Asp His Ile Asn Glu Glu Tyr Ile Lys Ser Leu Ile Asp Leu Met
            340                 345                 350

Val Thr Lys Gly Arg Pro Glu Leu Thr Lys Ser Trp Asn Phe Leu Val
        355                 360                 365

Ser Asp Asn Arg Tyr Ile Gly Phe Asp Glu Phe Asp Phe Gly Trp Gly
```

```
              370                 375                 380
Asn Pro Ile Phe Gly Gly Ile Leu Lys Ala Ile Ser Phe Thr Ser Phe
385                 390                 395                 400

Gly Val Ser Val Lys Asn Asp Lys Gly Glu Lys Gly Val Leu Ile Ala
                405                 410                 415

Ile Ser Leu Pro Pro Leu Ala Met Lys Lys Leu Gln Asp Ile Tyr Asn
                420                 425                 430

Met Thr Phe Arg Val Ile Ile Ser Asn Ile
            435                 440

<210> SEQ ID NO 68
<211> LENGTH: 447
<212> TYPE: PRT
<213> ORGANISM: Solanum tuberosum

<400> SEQUENCE: 68

Met Ala His Lys Thr Met Pro Ile Ser Ile Thr His His Lys Pro Lys
1               5                   10                  15

Leu Val Val Pro Ser Ile Val Thr Pro His Glu Ile Lys His Leu Ser
                20                  25                  30

Glu Ile Asp Asp Gln Gly Ser Thr Arg Phe His Val Ser Leu Leu Met
            35                  40                  45

Phe Tyr Lys Tyr Asn Ser Leu Met Glu Gly Lys Asp Pro Ala Lys Phe
50                  55                  60

Ile Lys Asp Gly Leu Ser Lys Thr Leu Val Phe Tyr Tyr Pro Leu Ala
65                  70                  75                  80

Gly Arg Leu Ile Glu Gly Pro Asn Lys Lys Leu Met Val Asn Cys Asn
                85                  90                  95

Gly Glu Gly Val Leu Phe Ile Glu Ala Asp Ala Asn Val Glu Leu Glu
            100                 105                 110

Lys Leu Gly Asp Ser Ile Lys Pro Pro Cys Pro Tyr Leu Asp Leu Leu
        115                 120                 125

Leu His Asn Val Pro Gly Ser Asp Gly Ile Ile Gly Cys Pro Leu Leu
    130                 135                 140

Leu Ile Gln Val Thr Arg Phe Arg Cys Gly Gly Phe Ala Phe Gly Phe
145                 150                 155                 160

Arg Leu Asn His Thr Met Met Asp Ala Tyr Gly Ile Lys Met Phe Leu
                165                 170                 175

Asn Ala Leu Ser Glu Leu Ile Gln Gly Ala Ser Thr Pro Ser Ile Leu
            180                 185                 190

Pro Val Trp Gln Arg Asp Leu Leu Ser Ala Thr Ser Ser Pro Cys Ile
        195                 200                 205

Thr Cys Thr His His Glu Phe Asp Glu Gln Ile Glu Ser Lys Ile Ala
    210                 215                 220

Trp Glu Ser Ile Glu Asp Lys Leu Ile Gln Gln Ser Phe Phe Phe Gly
225                 230                 235                 240

Asn Thr Glu Met Glu Val Ile Lys Asn His Val Pro Pro Asn Tyr Gly
                245                 250                 255

Cys Thr Lys Phe Glu Leu Leu Val Ala Phe Leu Trp Lys Cys Arg Thr
            260                 265                 270

Ile Ala Leu Asp Leu Pro Leu Glu Glu Ile Val Arg Leu Thr Leu Leu
        275                 280                 285

Met Asn Ile Arg Gly Lys Ser Leu Lys Phe Glu Leu Pro Pro Gly Tyr
    290                 295                 300
```

```
Tyr Gly Asn Ala Phe Ile Thr Pro Ala Val Ile Ser Lys Ala Gly Leu
305                 310                 315                 320

Leu Cys Ser Asn Pro Leu Thr Asn Ala Val Glu Leu Val Lys Lys Val
                325                 330                 335

Lys Asp His Leu Asn Glu Glu Tyr Val Lys Ser Met Thr Asp Leu Met
            340                 345                 350

Val Ile Lys Gly Arg Pro Gln Ile Thr Lys Ser Trp Asn Phe Leu Ile
        355                 360                 365

Ser Asp Asn Arg Tyr Ala Gly Phe Asp Glu Phe Asp Phe Gly Trp Gly
370                 375                 380

Asn Pro Ile Phe Gly Gly Val Pro Lys Ala Thr Ser Phe Ile Ser Phe
385                 390                 395                 400

Gly Val Ser Val Lys Asn Asp Lys Gly Glu Lys Gly Val Leu Ile Ala
                405                 410                 415

Ile Ser Leu Pro Pro Leu Ala Met Lys Lys Leu Gln Asp Ile Tyr Lys
            420                 425                 430

Met Thr Phe Thr Asn Ile Lys Gln Val Asn Ile Ile Ser Lys Ile
        435                 440                 445

<210> SEQ ID NO 69
<211> LENGTH: 447
<212> TYPE: PRT
<213> ORGANISM: Capsicum annuum

<400> SEQUENCE: 69

Met Ala His Thr Met Pro Val Ser Ile Thr Tyr His Lys Pro Glu Leu
1               5                   10                  15

Val Ala Pro Ser Met Val Thr Pro Tyr Glu Thr Lys His Leu Ser Asp
                20                  25                  30

Ile Asp Asp Gln Gly Ser Leu Arg Phe Gln Ile Pro Thr Leu Thr Phe
            35                  40                  45

Tyr Lys Tyr Asn Ser Ser Met Glu Gly Lys Asp Pro Ala Lys Phe Ile
        50                  55                  60

Lys Arg Gly Leu Ser Lys Thr Leu Val Phe Tyr Tyr Pro Leu Ala Gly
65                  70                  75                  80

Arg Leu Ile Glu Gly Pro Asn Lys Lys Leu Met Val Asn Cys Asn Gly
                85                  90                  95

Glu Gly Val Leu Phe Val Glu Ala Asp Ala Asn Val Glu Leu Glu Lys
                100                 105                 110

Leu Gly Glu Ser Ile Lys Pro Pro Cys Pro Tyr Leu Asp Leu Leu Leu
            115                 120                 125

His His Val Pro Gly Ser Asp Gly Ile Ile Gly Cys Pro Leu Val Leu
130                 135                 140

Val Gln Val Thr Arg Phe Asn Cys Gly Gly Phe Val Val Gly Phe Arg
145                 150                 155                 160

Val Asn His Thr Met Met Asp Ala Tyr Gly Phe Lys Ile Phe Leu Ser
                165                 170                 175

Ala Leu Ser Glu Leu Ile Gln Gly Ala Ser Ala Pro Ser Ile Leu Pro
            180                 185                 190

Val Trp Gln Arg His Leu Leu Ser Ala Arg Ser Ser Pro Cys Ile Thr
        195                 200                 205

Cys Thr His His Glu Phe Asp Glu Glu Ile Glu Ser Lys Ile Ala Trp
    210                 215                 220

Glu Ser Met Glu Asp Gln Leu Ile Gln Gln Ser Phe Phe Phe Gly Asn
225                 230                 235                 240
```

```
Lys Glu Met Glu Ala Met Arg Thr Gln Val Ser Pro Asn Cys Glu Ser
                245                 250                 255

Thr Lys Phe Glu Leu Leu Met Ala Phe Leu Trp Lys Cys Arg Thr Ile
            260                 265                 270

Ala Leu Asn Leu His Ser Glu Gln Ile Val Arg Leu Thr Tyr Leu Ile
        275                 280                 285

Asn Ile Arg Gly Lys Ser Gln Lys Phe Lys Leu Pro His Gly Tyr Tyr
    290                 295                 300

Gly Asn Ala Phe Ile Ser Pro Ala Thr Val Ser Lys Ala Gly Leu Leu
305                 310                 315                 320

Cys Ser Asn Pro Leu Ser Tyr Ala Val Glu Leu Val Lys Lys Leu Lys
                325                 330                 335

Asp His Leu Thr Glu Glu Tyr Ile Lys Ser Val Ser Asp Leu Ile Leu
            340                 345                 350

Ile Lys Gly Arg Pro Glu Leu Ser Lys Ser Trp Asn Phe Ile Ile Ser
        355                 360                 365

Asp Asn Arg Ser Ser Gly Leu Asp Asp Phe Asp Phe Gly Trp Gly Asn
    370                 375                 380

Pro Ile Leu Gly Gly Thr Ala Gln Ala Ile Ser Phe Ile Ser Phe Gly
385                 390                 395                 400

Val Pro Val Lys Asn Asp Lys Glu Glu Lys Gly Ile Leu Ile Ala Ile
                405                 410                 415

Ser Leu Pro Pro Leu Ala Met Glu Lys Phe Gln Glu Val Val Tyr Lys
            420                 425                 430

Met Thr Leu Arg Asn Val Glu Gly Val Asn Lys Ile Ser Lys Met
        435                 440                 445

<210> SEQ ID NO 70
<211> LENGTH: 444
<212> TYPE: PRT
<213> ORGANISM: Nicotiana tabacum

<400> SEQUENCE: 70

Met Ala Phe Ser Ile Thr His His Lys Pro Lys Leu Val Val Pro Ala
1               5                   10                  15

Lys Val Thr Pro Arg Glu Thr Lys His Leu Ser Asp Ile Asp Asp Gln
                20                  25                  30

Gly Ser Thr His Phe Gln Met Pro Thr Ile Met Phe Tyr Lys Tyr Asn
            35                  40                  45

Ser Ser Met Glu Gly Lys Asp Pro Ala Lys Leu Ile Lys Asn Gly Leu
        50                  55                  60

Ser Lys Thr Leu Val Phe Tyr Tyr Pro Leu Ala Gly Arg Ile Phe Glu
65                  70                  75                  80

Gly Pro Asn Lys Lys Leu Leu Val Asn Cys Asn Gly Glu Gly Ile Leu
                85                  90                  95

Phe Val Glu Ala Asp Ala Asn Ile Glu Leu Asp Lys Leu Gly Asn Ser
            100                 105                 110

Ile Lys Pro Pro Cys Thr Tyr Leu Asp Leu Val Ile His Asn Val Pro
        115                 120                 125

Gly Ser Asp Gly Ile Ile Gly Cys Pro Leu Leu Ile Gln Val Thr
    130                 135                 140

Arg Phe Ser Cys Gly Gly Phe Ala Val Gly Ile Arg Leu Asn His Thr
145                 150                 155                 160

Met Met Asp Ala Tyr Gly Leu Lys Lys Phe Leu Asn Ala Leu Ser Glu
```

```
                165                 170                 175
Leu Ile Gln Gly Ala Ser Thr Pro Thr Ile Leu Pro Val Trp Glu Arg
            180                 185                 190

Glu Leu Leu Asn Ala Arg Ser Leu Pro Cys Ile Thr Cys Thr His Pro
            195                 200                 205

Glu Tyr Asp Glu Gln Ile Glu Ser Lys Asn Ala Trp Lys Phe Leu Glu
            210                 215                 220

Asp Lys Leu Val Gln Lys Ser Phe Phe Gly Asn Lys Glu Met Glu
225                 230                 235                 240

Ala Ile Lys Asn Gln Val Phe Pro Asn His Ser Glu Ser Thr Lys Phe
                245                 250                 255

Glu Leu Leu Val Ala Phe Leu Trp Lys Tyr Arg Thr Ile Ala Leu Gly
            260                 265                 270

Leu Arg Pro Glu Glu Ile Val Arg Leu Thr Tyr Ile Val Asn Val Arg
            275                 280                 285

Gly Lys Ser Leu Lys Phe Glu Leu Pro Arg Gly Tyr Tyr Gly Asn Ala
            290                 295                 300

Phe Val Ala Pro Ala Ile Val Ser Lys Val Gly Leu Leu Cys Ser Ser
305                 310                 315                 320

Ser Leu Ser Tyr Ala Val Glu Leu Val Lys Val Lys Asp His Met
                325                 330                 335

Asn Glu Glu Tyr Ile Arg Ser Val Ala Asp Leu Met Val Ile Lys Gly
                340                 345                 350

Arg Pro Glu Leu Ser Lys Ser Trp Asn Phe Ile Val Ser Asp Asn Arg
                355                 360                 365

Ser Val Arg Phe Asp Glu Val Asp Phe Gly Trp Gly Lys Pro Ile Phe
            370                 375                 380

Gly Gly Val Pro Lys Ala Ile Ser Phe Ile Ser Phe Cys Val Pro Val
385                 390                 395                 400

Lys Asn Asp Lys Gly Glu Lys Gly Ile Leu Ile Ala Ile Ser Leu Pro
                405                 410                 415

Pro Leu Ala Met Glu Lys Phe Gln Glu Ala Val Tyr Asn Met Thr Phe
            420                 425                 430

Lys Asp Val Glu Gly Val Asn Ile Ile Ser Lys Ile
            435                 440

<210> SEQ ID NO 71
<211> LENGTH: 450
<212> TYPE: PRT
<213> ORGANISM: Fragaria chiloensis

<400> SEQUENCE: 71

Met Glu Lys Ile Glu Val Ser Ile Ile Ser Lys Tyr Thr Ile Lys Pro
1               5                   10                  15

Ser Ser Ser Leu Leu Gln Pro Tyr Lys Leu Ser Leu Leu Asp Gln Leu
            20                  25                  30

Thr Pro Pro Ala Tyr Val Pro Met Val Phe Phe Tyr Pro Ile Thr Glu
            35                  40                  45

His Val Phe Asn Leu Pro Gln Thr Leu Ala Asp Leu Arg Gln Ser Leu
        50                  55                  60

Ser Glu Thr Leu Ala Leu Tyr Tyr Pro Leu Ser Gly Arg Val Lys Asn
65                  70                  75                  80

Asn Leu Tyr Ile Asp Asn Phe Glu Glu Gly Val Pro Tyr Leu Glu Ala
                85                  90                  95
```

Gln Val Asn Cys Asp Met Thr Asp Phe Leu Arg Leu Gly Lys Ile Glu
            100                 105                 110

Cys Leu Asn Glu Phe Val Ser Ile Lys Pro Phe Ser Met Glu Ala Ile
        115                 120                 125

Ser Asp Glu Arg Tyr Pro Leu Leu Gly Val Gln Val Asn Val Phe Asp
    130                 135                 140

Ser Gly Ile Ala Ile Gly Val Ser Leu Ser His Lys Leu Ile Asp Gly
145                 150                 155                 160

Arg Thr Ala Tyr Cys Phe Leu Lys Ser Trp Gly Ala Val Phe Arg Gly
                165                 170                 175

Cys Arg Glu Asp Val Ile His Pro Ser Leu Ser Glu Ala Ala Leu Leu
            180                 185                 190

Phe Pro Pro Arg Asp Asp Leu Pro Glu Lys Tyr Ala Asp Gln Met Glu
        195                 200                 205

Gly Leu Trp Phe Ala Gly Lys Lys Val Ala Thr Arg Arg Phe Val Phe
210                 215                 220

Gly Ala Lys Ala Ile Ser Ser Ile Gln Asp Glu Ala Lys Ser Glu Ser
225                 230                 235                 240

Val Pro Lys Pro Ser Arg Val Gln Ala Val Thr Gly Phe Leu Trp Lys
                245                 250                 255

His Leu Ile Ala Ala Ser Arg Ala Leu Thr Ser Gly Thr Thr Ser Thr
            260                 265                 270

Arg Leu Ser Ile Ala Ala Gln Ala Val Asn Leu Arg Thr Arg Met Asn
        275                 280                 285

Met Glu Thr Val Leu Asp Asn Ala Thr Gly Asn Leu Ile Trp Trp Ala
290                 295                 300

Gln Ala Ile Leu Glu Leu Ser His Thr Thr Pro Glu Ile Ser Asp Leu
305                 310                 315                 320

Lys Leu Cys Asp Leu Val Asn Leu Leu Asn Gly Ser Val Lys Gln Cys
                325                 330                 335

Asn Gly Asp Tyr Phe Glu Thr Phe Lys Gly Lys Glu Gly Tyr Gly Arg
            340                 345                 350

Met Cys Glu Tyr Leu Asp Phe Gln Arg Thr Met Ser Ser Met Glu Pro
        355                 360                 365

Ala Pro Asp Ile Tyr Leu Phe Ser Ser Trp Thr Asn Phe Asn Pro
370                 375                 380

Leu Asp Phe Gly Trp Gly Arg Thr Ser Trp Ile Gly Val Ala Gly Lys
385                 390                 395                 400

Ile Glu Ser Ala Ser Cys Lys Phe Ile Ile Leu Val Pro Thr Gln Cys
                405                 410                 415

Gly Ser Gly Ile Glu Ala Trp Val Asn Leu Glu Glu Lys Met Ala
            420                 425                 430

Met Leu Glu Gln Asp Pro His Phe Leu Ala Leu Ala Ser Pro Lys Thr
        435                 440                 445

Leu Ile
450

<210> SEQ ID NO 72
<211> LENGTH: 455
<212> TYPE: PRT
<213> ORGANISM: Fragaria vesca subsp. vesca

<400> SEQUENCE: 72

Met Glu Lys Ile Glu Val Ser Ile Ile Ser Lys His Thr Ile Lys Pro
1               5                   10                  15

```
Ser Ala Ser Ser Thr Pro Leu Gln Pro Tyr Asn Leu Thr Leu Leu Asp
            20                  25                  30

Gln Leu Thr Pro Pro Ala Tyr Val Pro Met Val Phe Phe Tyr Pro Ile
            35                  40                  45

Thr Asp His Val Phe Asn Leu Pro Gln Thr Leu Ala Asp Leu Arg Gln
 50                  55                  60

Ala Leu Ser Glu Thr Leu Thr Leu Tyr Tyr Pro Leu Ser Gly Arg Val
 65                  70                  75                  80

Lys Asn Asn Leu Tyr Ile Asp Asp Phe Glu Glu Gly Val Pro Tyr Leu
            85                  90                  95

Glu Ala Arg Val Asn Cys Asp Met Thr Asp Phe Leu Arg Leu Arg Lys
            100                 105                 110

Ile Glu Cys Leu Asn Glu Phe Val Pro Ile Lys Pro Phe Ser Met Glu
            115                 120                 125

Ala Ile Ser Asp Glu Arg Tyr Pro Leu Leu Gly Val Gln Val Asn Ile
130                 135                 140

Leu Asp Ser Gly Ile Ala Ile Cys Val Phe Ile Ser His Lys Leu Ile
145                 150                 155                 160

Asp Gly Arg Thr Ala Asp Cys Phe Leu Lys Ser Trp Gly Ala Ile Phe
            165                 170                 175

Arg Gly Cys Arg Glu Asp Ile Ile His Pro Ser Leu Ser Glu Ala Ala
            180                 185                 190

Leu Leu Phe Pro Pro Arg Asp Asp Leu Pro Glu Lys Tyr Ala Gly Gln
            195                 200                 205

Met Glu Arg Val Trp Phe Ala Gly Lys Lys Val Ala Thr Arg Arg Phe
            210                 215                 220

Val Phe Gly Ala Lys Ala Ile Ser Ser Ile Gln Asp Glu Ala Lys Ser
225                 230                 235                 240

Glu Pro Val Pro Lys Pro Ser Arg Val Gln Ala Val Thr Gly Phe Leu
            245                 250                 255

Trp Lys His Leu Ile Ala Ala Ser Arg Ala Leu Thr Leu Gly Thr Thr
            260                 265                 270

Ser Thr Arg Leu Ser Ile Ala Ala Gln Ala Val Asn Leu Arg Thr Arg
            275                 280                 285

Ile Asn Met Glu Thr Val Leu Asp Asn Ala Ile Gly Asn Leu Met Trp
            290                 295                 300

Trp Ala Gln Ala Ile Leu Glu Leu Cys His Thr Thr Pro Glu Ile Ser
305                 310                 315                 320

Asp Leu Lys Leu Cys Asp Leu Val Asn Leu Asn Gly Ser Val Lys
            325                 330                 335

Gln Cys Asn Ser Asp Tyr Phe Glu Thr Phe Lys Gly Lys Glu Gly Tyr
            340                 345                 350

Gly Arg Met Cys Glu Tyr Leu Asp Phe Gln Arg Thr Met Ser Ser Met
            355                 360                 365

Glu Pro Ser Arg Glu Ile Tyr Leu Phe Ser Ser Trp Thr Asn Phe Phe
            370                 375                 380

Asn Ala Leu Asp Phe Gly Trp Gly Arg Thr Ser Trp Ile Gly Val Ala
385                 390                 395                 400

Gly Lys Ile Glu Ser Ala Phe Cys Asn Leu Thr Ile Leu Val Pro Thr
            405                 410                 415

Pro Cys Asn Thr Gly Ile Glu Ala Trp Val Asn Leu Glu Glu Glu Lys
            420                 425                 430
```

```
Met Ala Met Leu Glu Gln Asp Pro Gln Phe Leu Ala Leu Ala Ser Pro
        435                 440                 445

Lys Thr Leu Ile Ser Arg Asn
    450                 455

<210> SEQ ID NO 73
<211> LENGTH: 459
<212> TYPE: PRT
<213> ORGANISM: Rosa rugosa

<400> SEQUENCE: 73

Met Glu Lys Ile Glu Val Ser Ile Ile Ser Arg Asp Thr Ile Lys Pro
1               5                   10                  15

Ser Ala Ala Ser Ser Leu His Pro Tyr Lys Leu Ser Ile Ile Asp
            20                  25                  30

Gln Phe Thr Pro Thr Thr Tyr Phe Pro Val Ile Phe Tyr Pro Ile
        35                  40                  45

Thr Asp Pro Val Phe Asn Leu Pro Gln Thr Leu Thr Asp Leu Lys Ile
    50                  55                  60

Thr Val Ser Gln Thr Leu Thr Leu Tyr Tyr Pro Leu Ser Gly Arg Ile
65                  70                  75                  80

Lys Asn Asn Leu Tyr Ile Asp Asp Phe Glu Ala Gly Ile Pro Tyr Leu
                85                  90                  95

Glu Ala Arg Val Asn Cys His Met Ile Asp Phe Leu Arg Leu Pro Lys
            100                 105                 110

Ile Glu Trp Leu Asn Glu Phe Val Pro Ile Ala Pro Tyr Arg Lys Glu
        115                 120                 125

Thr Ile Ser Glu Leu Leu Pro Leu Leu Gly Ile Gln Val Asn Ile Phe
    130                 135                 140

Asp Ser Gly Ile Ala Ile Gly Val Ser Phe Ser His Lys Ile Asn Asp
145                 150                 155                 160

Gly Glu Thr Ala Asn Cys Phe Leu Lys Ser Trp Val Ala Ile Phe Arg
                165                 170                 175

Gly Tyr Arg Asn Lys Ile Ile His Pro Asn Leu Ser Gln Ala Ala Leu
            180                 185                 190

Leu Phe Pro Ser Arg Asp Asp Leu Ser Glu Lys Tyr Val Ala Met Met
        195                 200                 205

Glu Arg Trp Trp Phe Gly Glu Lys Lys Val Val Thr Arg Arg Phe Val
    210                 215                 220

Phe Asp Thr Lys Ala Ile Ser Ala Leu Gln His Glu Gly Lys Ser Glu
225                 230                 235                 240

Tyr Val Pro Lys Pro Ser Arg Val Gln Ala Leu Thr Gly Phe Leu Trp
                245                 250                 255

Lys His Gln Leu Ala Ala Thr Arg Ala Leu Ser Ser Gly Thr Ser Thr
            260                 265                 270

Arg Phe Ser Leu Ala Ile Gln Ala Val Asn Leu Arg Ser Arg Met Asn
        275                 280                 285

Met Lys Thr Thr Leu Asp Asn Ala Ile Gly Asn Ile Phe Leu Trp Ala
    290                 295                 300

Pro Ala Phe Leu Glu Leu Asn Tyr Thr Thr Pro Glu Ser Ser Asp His
305                 310                 315                 320

Lys Leu Cys Asp Leu Val Asn Leu Leu Lys Glu Ser Val Lys Glu Tyr
                325                 330                 335

Asn Ser Asp Tyr Leu Glu Thr Leu Lys Gly Glu Lys Gly Tyr Gly Gly
            340                 345                 350
```

```
Met Cys Asp Trp Leu Asp Leu Met Asp Glu Gly Ser Ser Ile Glu Pro
        355                 360                 365

Ala Leu Glu Ile Tyr Ser Phe Ser Ser Trp Thr Arg Met Phe Asp Gln
    370                 375                 380

Val Asp Phe Gly Trp Gly Lys Pro Phe Trp Ile Gly Val Thr Gly Lys
385                 390                 395                 400

Val Gln Thr Thr Tyr Thr Asn Ser Thr Val Leu Val Glu Thr Gln Cys
                405                 410                 415

Glu Asn Gly Ile Glu Ala Trp Val Thr Leu Asp Gln Lys Arg Met Ala
                420                 425                 430

Met Leu Glu Gln Asp Pro Gln Phe Leu Ala Phe Ala Ser Pro Thr Pro
        435                 440                 445

Gly Ile Ser Met Ala Ser Ser Val Gly Ile Asp
        450                 455
```

METHOD FOR PRODUCING MUTANT ENZYME, AND MUTANT ALCOHOL ACYLTRANSFERASE

TECHNICAL FIELD

The present invention relates to a method for producing a mutant enzyme and a mutant alcohol acyltransferase. More specifically, the present invention relates to a method for obtaining an enzyme such as alcohol acyltransferase as a highly active soluble recombinant protein, etc.

BACKGROUND ART

Proteins are folded into their unique conformations after translation in cells so as to have functions. In the case of expressing a heterologous protein using a transformant (recombinant), an inclusion body may be formed without normal folding of the protein in host cells. It is known that a protein in the inclusion body becomes an inactive protein that has lost original activity, and is insolubilized in some cases. The inclusion body is formed probably because a protein does not undergo normal folding in an intracellular environment (temperature, transcription rate, translation rate, etc.) of a host different from that of a species from which the protein is derived.

In order to solve this problem, an attempt has been made to obtain a mutated protein expressed in an active form by introducing a mutation to a protein and thereby achieving normal folding similar to that of a wild-type protein in a recombinant. For example, it has been reported as to a plant-derived hydroxynitrile lyase that an enzyme having drastically improved solubility was able to be obtained by the introduction of a mutation (Non Patent Literature 1).

In relation to the present invention, alcohol acyltransferase (AAT) will be described. Patent Literatures 1 to 3 propose a method for producing isobutyric acid ester or methacrylic acid ester using alcohol acyltransferase (AAT) from isobutyryl-CoA or methacryl-CoA produced from biomass.

Carboxylic acid esters are used as starting materials for various industrial chemical products, fragrances, pharmaceutical products, etc. For example, isobutyric acid ester is typically an ester compound important as a starting material for esters for fragrances, pharmaceutical products, peroxides, etc.

Methacrylic acid ester is typically used as a starting material for acrylic resins and also often demanded as a comonomer in the fields of coating materials, adhesives, resin modifying agents, etc.

In recent years, techniques of producing various chemical products using biomass instead of conventional fossil materials as a carbon source have received attention from the viewpoint of prevention of global warming and environmental protection. Isobutyric acid ester or methacrylic acid ester is also expected to be produced from biomass.

A possible method for synthesizing an ester such as isobutyric acid ester or methacrylic acid ester from biomass using AAT is fermentative production using a microbial recombinant harboring a gene group for the synthesis of CoA compounds such as isobutyryl-CoA or methacryl-CoA from biomass, and a gene of AAT which catalyzes the reaction of the CoA compounds into esters.

However, a problem of the expression of AAT in a recombinant is also the inclusion body formation mentioned above. Particularly, in the case of expressing plant-derived AAT with *E. coli* as a host, it is known that a large majority of enzymes are expressed as inactive insoluble proteins (Non Patent Literature 2).

Non Patent Literatures 3 and 4 have reported that in the case of expressing apple-derived AAT in an *E. coli* recombinant, a soluble protein was obtained only by using a particular lineage (C43 (DE3)), whereas no soluble protein was obtained from a general lineage (BL21 (DE3)-derived strain).

CITATION LIST

Patent Literature

Patent Literature 1: Japanese Patent Laid-Open No. 2015-116141
Patent Literature 2: International Publication No. WO 2014/038214
Patent Literature 3: International Publication No. WO 2014/038216

Non Patent Literature

Non Patent Literature 1: Protein Eng. Des. Sel. (2011) 24: 607-616
Non Patent Literature 2: Metabolic Engineering (2015) 27: 20-28
Non Patent Literature 3: FEBS J. (2005) 272: 3132-3144
Non Patent Literature 4: Phytochemistry (2006) 67: 658-667

SUMMARY OF INVENTION

Technical Problem

As mentioned above, a method has been proposed which achieves normal folding similar to that of a wild-type protein in a transformant (recombinant) by introducing a mutation to a protein, in order to suppress inclusion body formation. However, a problem of this method is how to efficiently search for a mutation that can achieve normal folding.

Accordingly, a main object of the present invention is to provide an efficient method for expressing a protein of interest as an active soluble recombinant protein in a recombinant.

Solution to Problem

In order to attain the object, the present invention provides the following [1] to [25]:

[1] A method for producing an enzyme having improved activity per recombinant as compared with a reference form, comprising the step of:
expressing a mutant having an amino acid sequence derived from the amino acid sequence of the reference form by the substitution of two or more cysteine residues by other amino acid residues.

[2] The method for producing an enzyme according to [1], comprising the steps of:
(1) preparing recombinants each expressing a mutant having an amino acid sequence derived from the amino acid sequence of the reference form by the substitution of one or more cysteine residues by other amino acid residues;
(2) selecting a plurality of mutants that exhibit 50% or more activity per recombinant relative to 100% activity of the reference form; and
(3) expressing a mutant in which corresponding amino acid residues are substituted at two or more positions among the respective positions of the substituted amino acid residues of the mutants selected in step (2).

[3] The method for producing an enzyme according to [1] or [2], wherein the enzyme is alcohol acyltransferase.

[4] The method for producing an enzyme according to [3], wherein the amino acid sequence of the reference form is an amino acid sequence represented by any of SEQ ID NOs: 1, 2, 3, 64, 65 and 66.

[5] The method for producing an enzyme according to any of [1] to [4], wherein the other amino acid residues are alanine or arginine.

[6] A mutant alcohol acyltransferase having improved activity as compared with a reference form, wherein the mutant alcohol acyltransferase has an amino acid sequence derived from the amino acid sequence of the reference form by the substitution of one or more cysteine residues by other amino acid residues.

[7] The mutant alcohol acyltransferase according to [6], consisting of an amino acid sequence having 70% or higher sequence identity to the amino acid sequence represented by SEQ ID NO: 1 or 2, wherein the mutant alcohol acyltransferase has one or more amino acid substitutions selected from the following amino acid substitutions:
(1) a substitution of cysteine corresponding to cysteine at position 48 by another amino acid residue in alignment with the amino acid sequence represented by SEQ ID NO: 1 or 2,
(2) a substitution of cysteine corresponding to cysteine at position 150 by another amino acid residue in alignment with the amino acid sequence represented by SEQ ID NO: 1 or 2,
(3) a substitution of cysteine corresponding to cysteine at position 167 by another amino acid residue in alignment with the amino acid sequence represented by SEQ ID NO: 1 or 2,
(4) a substitution of cysteine corresponding to cysteine at position 270 by another amino acid residue in alignment with the amino acid sequence represented by SEQ ID NO: 1 or 2,
(5) a substitution of cysteine corresponding to cysteine at position 274 by another amino acid residue in alignment with the amino acid sequence represented by SEQ ID NO: 1 or 2, and
(6) a substitution of cysteine corresponding to cysteine at position 447 by another amino acid residue in alignment with the amino acid sequence represented by SEQ ID NO: 1 or 2.

[8] The mutant alcohol acyltransferase according to [6], consisting of an amino acid sequence having 70% or higher sequence identity to the amino acid sequence represented by SEQ ID NO: 64 or 66, wherein the mutant alcohol acyltransferase has one or more amino acid substitutions selected from the following amino acid substitutions:
(1) a substitution of cysteine corresponding to cysteine at position 206 by another amino acid residue in alignment with the amino acid sequence represented by SEQ ID NO: 64 or 66,
(2) a substitution of cysteine corresponding to cysteine at position 209 by another amino acid residue in alignment with the amino acid sequence represented by SEQ ID NO: 64 or 66,
(3) a substitution of cysteine corresponding to cysteine at position 256 by another amino acid residue in alignment with the amino acid sequence represented by SEQ ID NO: 64 or 66,
(4) a substitution of cysteine corresponding to cysteine at position 269 by another amino acid residue in alignment with the amino acid sequence represented by SEQ ID NO: 64 or 66, and
(5) a substitution of cysteine corresponding to cysteine at position 322 by another amino acid residue in alignment with the amino acid sequence represented by SEQ ID NO: 64 or 66.

[9] The mutant alcohol acyltransferase according to [6], consisting of an amino acid sequence having 70% or higher sequence identity to the amino acid sequence represented by SEQ ID NO: 65, wherein the mutant alcohol acyltransferase has one or more amino acid substitutions selected from the following amino acid substitutions:
(1) a substitution of cysteine corresponding to cysteine at position 115 by another amino acid residue in alignment with the amino acid sequence represented by SEQ ID NO: 65,
(2) a substitution of cysteine corresponding to cysteine at position 167 by another amino acid residue in alignment with the amino acid sequence represented by SEQ ID NO: 65,
(3) a substitution of cysteine corresponding to cysteine at position 179 by another amino acid residue in alignment with the amino acid sequence represented by SEQ ID NO: 65,
(4) a substitution of cysteine corresponding to cysteine at position 325 by another amino acid residue in alignment with the amino acid sequence represented by SEQ ID NO: 65, and
(5) a substitution of cysteine corresponding to cysteine at position 356 by another amino acid residue in alignment with the amino acid sequence represented by SEQ ID NO: 65.

[10] The mutant alcohol acyltransferase according to any of [6] to [9], wherein the another amino acid residue is alanine or arginine.

[11] The mutant alcohol acyltransferase according to any of [7] to [10], wherein the mutant alcohol acyltransferase is derived from a plant.

[12] The mutant alcohol acyltransferase according to [6], wherein the mutant alcohol acyltransferase has one or more amino acid substitutions selected from the following amino acid substitutions in the amino acid sequence represented by SEQ ID NO: 1 or 2:
(1) a substitution of cysteine at position 48 by another amino acid residue,
(2) a substitution of cysteine at position 150 by another amino acid residue,
(3) a substitution of cysteine at position 167 by another amino acid residue,
(4) a substitution of cysteine at position 270 by another amino acid residue,
(5) a substitution of cysteine at position 274 by another amino acid residue, and
(6) a substitution of cysteine at position 447 by another amino acid residue.

[13] The mutant alcohol acyltransferase according to [6], wherein the mutant alcohol acyltransferase has one or more amino acid substitutions selected from the following amino acid substitutions in the amino acid sequence represented by SEQ ID NO: 64 or 66:
(1) a substitution of cysteine at position 206 by another amino acid residue,
(2) a substitution of cysteine at position 209 by another amino acid residue, (3) a substitution of cysteine at position 256 by another amino acid residue,
(4) a substitution of cysteine at position 269 by another amino acid residue, and
(5) a substitution of cysteine at position 322 by another amino acid residue.

[14] The mutant alcohol acyltransferase according to [6], wherein the mutant alcohol acyltransferase has one or more amino acid substitutions selected from the following amino acid substitutions in the amino acid sequence represented by SEQ ID NO: 65:
(1) a substitution of cysteine at position 115 by another amino acid residue,
(2) a substitution of cysteine at position 167 by another amino acid residue,
(3) a substitution of cysteine at position 179 by another amino acid residue,
(4) a substitution of cysteine at position 325 by another amino acid residue, and
(5) a substitution of cysteine at position 356 by another amino acid residue.

[15] The mutant alcohol acyltransferase according to any of [12] to [14], wherein the another amino acid residue is alanine or arginine.

[16] The mutant alcohol acyltransferase according to [12], consisting of the amino acid sequence represented by SEQ ID NO: 4 or 7.

[17] The mutant alcohol acyltransferase according to [7] or [12], wherein the mutant alcohol acyltransferase further has one or more amino acid substitutions selected from the following amino acid substitutions:
(1) a substitution of alanine at position 64 by valine, isoleucine or threonine,
(2) a substitution of lysine at position 117 by glutamine, (3) a substitution of valine at position 248 by alanine, and
(4) a substitution of glutamine at position 363 by lysine, proline, alanine, arginine, glycine or tryptophan.

[18] The mutant alcohol acyltransferase according to [17], consisting of an amino acid sequence represented by any of SEQ ID NOs: 5, 6, 8 to 11 and 13.

[19] A mutant alcohol acyltransferase consisting of an amino acid sequence having 70% or higher sequence identity to the amino acid sequence represented by SEQ ID NO: 1 or 2, wherein the mutant alcohol acyltransferase has one or more amino acid substitutions selected from the following amino acid substitutions:
(1) a substitution of an amino acid residue corresponding to alanine at position 64 by valine, isoleucine or threonine in alignment with the amino acid sequence represented by SEQ ID NO: 1 or 2,
(2) a substitution of an amino acid corresponding to lysine at position 117 by glutamine in alignment with the amino acid sequence represented by SEQ ID NO: 1 or 2,
(3) a substitution of an amino acid corresponding to valine at position 248 by alanine in alignment with the amino acid sequence represented by SEQ ID NO: 1 or 2, and
(4) a substitution of an amino acid corresponding to glutamine at position 363 by lysine, proline, alanine, arginine, glycine or tryptophan in alignment with the amino acid sequence represented by SEQ ID NO: 1 or 2.

[20] The mutant alcohol acyltransferase according to [19], wherein the mutant alcohol acyltransferase is derived from a plant.

[21] A mutant alcohol acyltransferase having one or more amino acid substitutions selected from the following amino acid substitutions in the amino acid sequence represented by SEQ ID NO: 1 or 2:
(1) a substitution of alanine at position 64 by valine, isoleucine or threonine,
(2) a substitution of lysine at position 117 by glutamine, (3) a substitution of valine at position 248 by alanine, and
(4) a substitution of glutamine at position 363 by lysine, proline, alanine, arginine, glycine or tryptophan.

[22] The mutant alcohol acyltransferase according to [21], consisting of an amino acid sequence represented by any of SEQ ID NOs: 3, 5, 6, 8 to 11 and 13.

[23] A vector for the expression of the alcohol acyltransferase according to any of [6] to [20].

[24] A transformant transformed by the vector according to [23].

In another aspect, the present invention also provides the following [1] to [24]:

[1] A method for producing an enzyme having improved activity per recombinant as compared with a reference form, comprising the steps of:
(1) preparing recombinants each expressing a mutant having an amino acid sequence derived from the amino acid sequence of the reference form by the substitution of one or more cysteine residues by other amino acid residues;
(2) selecting mutants that exhibit 50% or more activity per recombinant as compared with the reference form; and
(3) expressing a mutant in which corresponding amino acid substitutions are introduced at two or more positions among the respective positions of the introduced amino acid substitutions of the mutants selected in step (2).

[2] The production method according to [1], wherein the enzyme is alcohol acyltransferase.

[3] The production method according to [2], wherein the amino acid sequence of the reference form is the amino acid sequence represented by SEQ ID NO: 1, SEQ ID NO: 2 or SEQ ID NO: 3.

[4] The production method according to any of [1] to [3], wherein the other amino acid residues are alanine or arginine.

[5] A method for producing an enzyme having improved activity per recombinant as compared with a reference form, comprising the step of:
expressing a mutant having an amino acid sequence derived from the amino acid sequence of the reference form by the substitution of one or more cysteine residues by other amino acid residues.

[6] The production method according to [5], wherein the enzyme is alcohol acyltransferase.

[7] The production method according to [6], wherein the amino acid sequence of the reference form is the amino acid sequence represented by SEQ ID NO: 1, SEQ ID NO: 2 or SEQ ID NO: 3.

[8] The production method according to any of [5] to [7], wherein the other amino acid residues are alanine or arginine.

[9] A mutant alcohol acyltransferase consisting of an amino acid sequence having 80% or higher sequence identity to the amino acid sequence represented by SEQ ID NO: 1, wherein
the mutant alcohol acyltransferase has one or more amino acid substitutions selected from the following amino acid substitutions:
(1) a substitution of cysteine corresponding to cysteine at position 48 by another amino acid residue in alignment with the amino acid sequence represented by SEQ ID NO: 1,
(2) a substitution of cysteine corresponding to cysteine at position 150 by another amino acid residue in alignment with the amino acid sequence represented by SEQ ID NO: 1, (3) a substitution of cysteine corresponding to cysteine at position 167 by another amino acid residue in alignment with the amino acid sequence represented by SEQ ID NO: 1,
(4) a substitution of cysteine corresponding to cysteine at position 270 by another amino acid residue in alignment with the amino acid sequence represented by SEQ ID NO: 1,
(5) a substitution of cysteine corresponding to cysteine at position 274 by another amino acid residue in alignment with the amino acid sequence represented by SEQ ID NO: 1, and
(6) a substitution of cysteine corresponding to cysteine at position 447 by another amino acid residue in alignment with the amino acid sequence represented by SEQ ID NO: 1.

[10] The mutant alcohol acyltransferase according to [9], wherein the another amino acid residue is alanine or arginine.

[11] A mutant alcohol acyltransferase having one or more amino acid substitutions selected from the following amino acid substitutions in the amino acid sequence represented by SEQ ID NO: 1:
(1) a substitution of cysteine at position 48 by another amino acid residue,
(2) a substitution of cysteine at position 150 by another amino acid residue,
(3) a substitution of cysteine at position 167 by another amino acid residue,
(4) a substitution of cysteine at position 270 by another amino acid residue,
(5) a substitution of cysteine at position 274 by another amino acid residue, and
(6) a substitution of cysteine at position 447 by another amino acid residue.

[12] The mutant alcohol acyltransferase according to [11], wherein the another amino acid residue is alanine or arginine.

[13] The mutant alcohol acyltransferase according to [11], consisting of the amino acid sequence represented by SEQ ID NO: 4 or 7.

[14] The mutant alcohol acyltransferase according to [11], wherein the mutant alcohol acyltransferase further has one or more amino acid substitutions selected from the following amino acid substitutions:
(1) a substitution of alanine at position 64 by valine, isoleucine or threonine,
(2) a substitution of lysine at position 117 by glutamine,
(3) a substitution of valine at position 248 by alanine, and
(4) a substitution of glutamine at position 363 by lysine, proline, alanine, arginine, glycine or tryptophan.

[15] The mutant alcohol acyltransferase according to [14], consisting of an amino acid sequence represented by any of SEQ ID NOs: 5, 6, 8 to 11 and 13.

[16] A mutant alcohol acyltransferase consisting of an amino acid sequence having 80% or higher sequence identity to the amino acid sequence represented by SEQ ID NO: 1, wherein the mutant alcohol acyltransferase has one or more amino acid substitutions selected from the following amino acid substitutions:
(1) a substitution of an amino acid residue corresponding to alanine at position 64 by valine, isoleucine or threonine in alignment with the amino acid sequence represented by SEQ ID NO: 1,
(2) a substitution of an amino acid corresponding to valine at position 248 by alanine in alignment with the amino acid sequence represented by SEQ ID NO: 1,
(3) a substitution of an amino acid corresponding to glutamine at position 363 by lysine, proline, alanine, arginine, glycine or tryptophan in alignment with the amino acid sequence represented by SEQ ID NO: 1, and
(4) a substitution of an amino acid corresponding to lysine at position 117 by glutamine in alignment with the amino acid sequence represented by SEQ ID NO: 1.

[17] A mutant alcohol acyltransferase having one or more amino acid substitutions selected from the following amino acid substitutions in the amino acid sequence represented by SEQ ID NO: 1:
(1) a substitution of alanine at position 64 by valine, isoleucine or threonine,
(2) a substitution of lysine at position 117 by glutamine,
(3) a substitution of valine at position 248 by alanine, and
(4) a substitution of glutamine at position 363 by lysine, proline, alanine, arginine, glycine or tryptophan.

[18] The mutant alcohol acyltransferase according to [17], consisting of an amino acid sequence represented by any of SEQ ID NOs: 3, 5, 6, 8 to 11 and 13.

[19] A vector for the expression of the alcohol acyltransferase according to any of [9] to [18].

[20] A transformant transformed by the vector according to [19].

[21] A method for producing a plant-derived enzyme having improved activity per recombinant as compared with a reference form, comprising the steps of:
(1) preparing non-plant cell recombinants each expressing a mutant having an amino acid sequence derived from the amino acid sequence of the reference form by the substitution of one or two or more cysteine residues by other amino acid residues;
(2) measuring enzymatic activity per recombinant of the mutant;
(3) selecting mutants that exhibit 50% or more activity per recombinant as compared with the reference form; and
(4) expressing, in the non-plant cell, a mutant in which corresponding amino acid substitutions are introduced at two or more positions among the respective positions of the introduced amino acid substitutions of the mutants selected in step (3).

[22] The production method according to [21], wherein the enzyme is an apple-derived alcohol acyltransferase.

[23] The production method according to [21] or [22], wherein the non-plant cell is an *E. coli* cell.

[24] The production method according to any of [21] to [23], wherein the other amino acid residues are alanine or arginine.

In the method for producing a mutant enzyme according to the present invention, the "reference form" means an enzyme to which the substitution of one or more cysteine residues by other amino acid residues is to be introduced. The amino acid sequence of the mutant enzyme obtained by the production method according to the present invention differs from the amino acid sequence of the reference form only in that one or more cysteine residues are substituted by other amino acid residues. The reference form is not limited to a natural (wild-type) enzyme and may be a mutant enzyme containing one or more amino acid substitutions introduced in the amino acid sequence of the wild-type enzyme. Also, the reference form may be a mutant enzyme having an amino acid sequence derived from the amino acid sequence of the wild-type enzyme by the insertion or addition of one or more amino acids, or an amino acid sequence derived from the amino acid sequence of the wild-type enzyme by the deletion of one or more amino acids. A mutant enzyme having improved activity can be obtained by further introducing the substitution of one or two or more cysteine residues by other amino acid residues to any of these mutant enzymes as the reference form.

Advantageous Effects of Invention

The present invention provides an efficient method for expressing a protein of interest as an active soluble recombinant protein in a recombinant.

BRIEF DESCRIPTION OF DRAWINGS

FIG. 1 is a diagram showing the alignment of the amino acid sequences of AATs derived from SEQ ID NO: 1 (apple: *Malus pumila*), SEQ ID NO: 12 (apple: *Malus domestica*), SEQ ID NO: 61 (Asian pear: *Pyrus pyrifolia*), SEQ ID NO: 62 (loquat: *Eriobotrya japonica*) and SEQ ID NO: 63 (kaki persimmon: *Diospyros kaki*).

FIG. 2 is a diagram showing the alignment of the amino acid sequences of AATs derived from SEQ ID NO: 66 (tomato (wild species): *Solanum pennellii*), SEQ ID NO: 67 (tomato (cultivated species): *Solanum lycopersicum*), SEQ ID NO: 68 (potato: *Solanum tuberosum*), SEQ ID NO: 69 (pepper: *Capsicum annuum*) and SEQ ID NO: 70 (tobacco: *Nicotiana tabacum*).

FIG. 3 is a diagram showing the alignment of the amino acid sequences of AATs derived from SEQ ID NO: 65 (garden strawberry: *Fragaria×ananassa*), SEQ ID NO: 71 (beach strawberry: *Fragaria chiloensis*), SEQ ID NO: 72 (woodland strawberry: *Fragaria vesca*) and SEQ ID NO: 73 (Japanese rose: *Rosa rugosa*).

Figure 5:
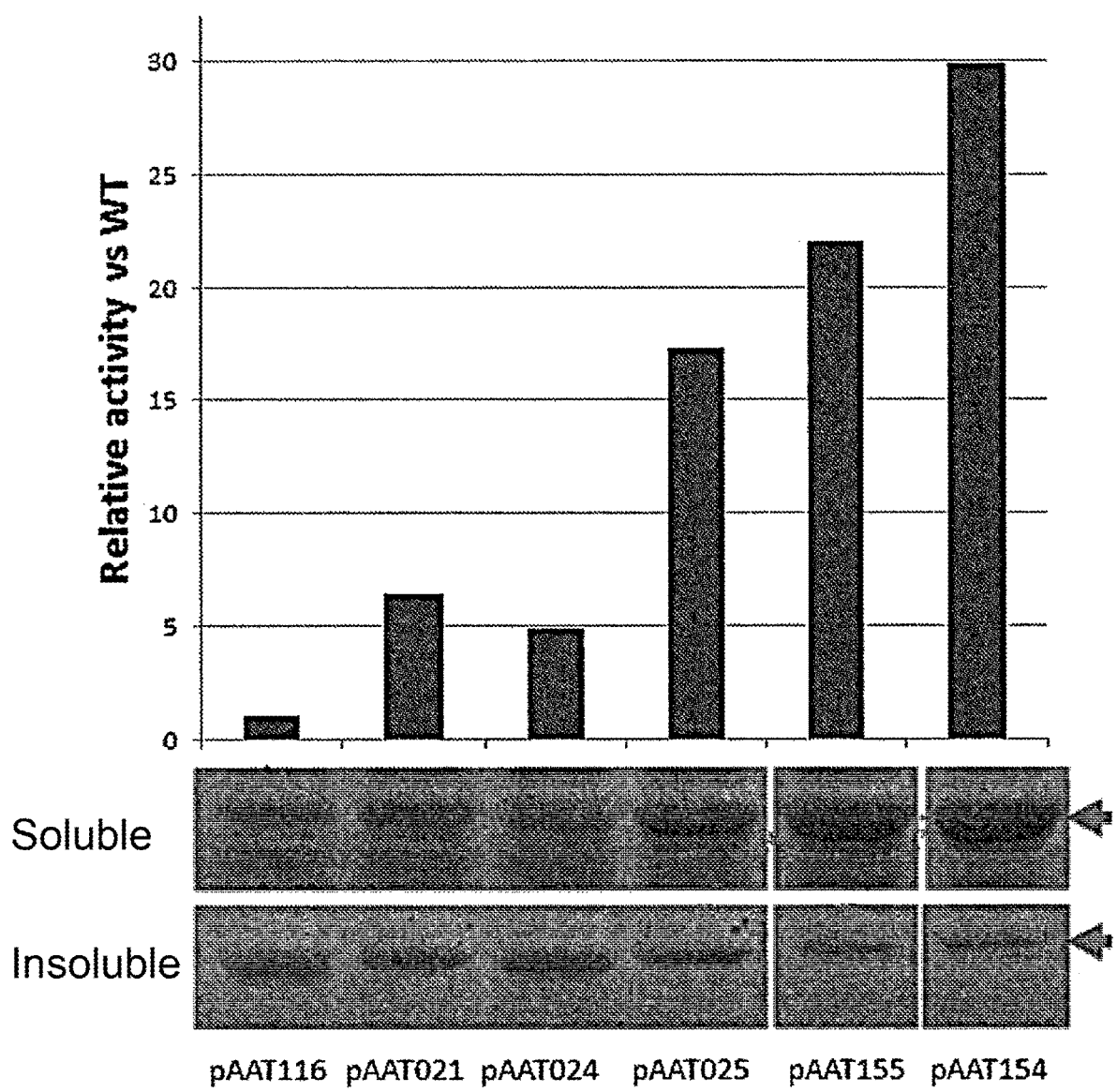

The upper diagram of FIG. 5 is a graph showing results of measuring AAT activity per bacterial cell weight as to recombinants expressing a mutant (pAAT021) containing a quadruple mutation introduced in apple wild-type AAT, a mutant (pAAT024) containing 6 cysteine substitutions introduced therein, a mutant (pAAT025) containing a quadruple mutation and 6 cysteine substitutions introduced therein, a mutant (pAAT155) containing a quadruple mutation and Cys150Arg introduced therein, or a mutant (pAAT154) containing a quadruple mutation and 6 cysteine substitutions (including Cys150Arg at position 150) introduced therein. The ordinate indicates AAT activity by a relative value when the activity of a recombinant expressing a reference form (pAAT116) having neither a quadruple mutation nor a cysteine substitution is defined as 1. The lower diagrams of FIG. 5 are SDS-polyacrylamide gel electrophoretic patterns of soluble fractions and insoluble fractions from cell extracts containing the mutants.

Figure 6:
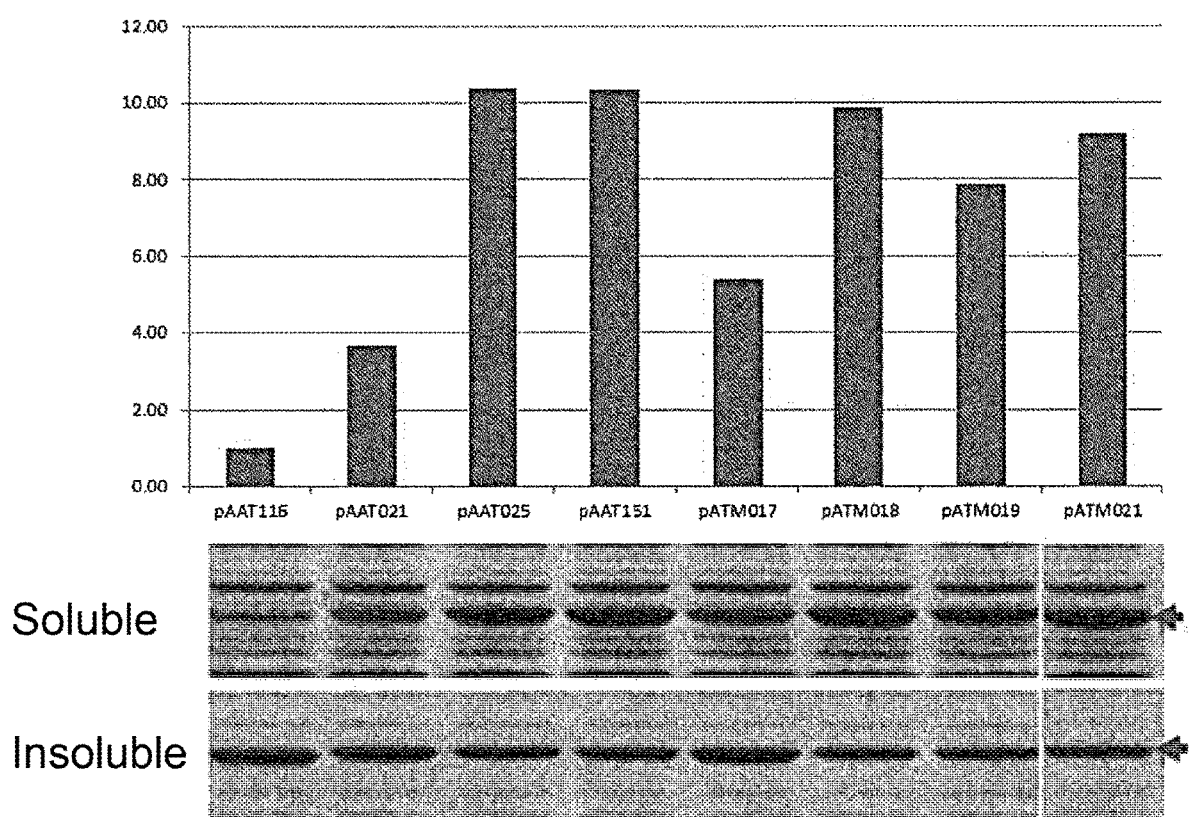

The upper diagram of FIG. 6 is a graph showing results of measuring AAT activity per bacterial cell weight as to recombinants expressing a mutant (pAAT021) containing a quadruple mutation introduced in apple wild-type AAT, a mutant (pAAT025) containing a quadruple mutation and 6 cysteine substitutions introduced therein, a mutant (pAAT151) containing a quadruple mutation and 5 cysteine substitutions introduced therein, or a mutant (pATM017, pATM018, pATM019 or pATM021) containing a quadruple mutation and 4 cysteine substitutions introduced therein. The ordinate indicates AAT activity by a relative value when the activity of a recombinant expressing a reference form (pAAT116) having neither a quadruple mutation nor a cysteine substitution is defined as 1. The lower diagrams of FIG. 6 are SDS-polyacrylamide gel electrophoretic patterns of soluble fractions and insoluble fractions from cell extracts containing the mutants.

Figure 7:
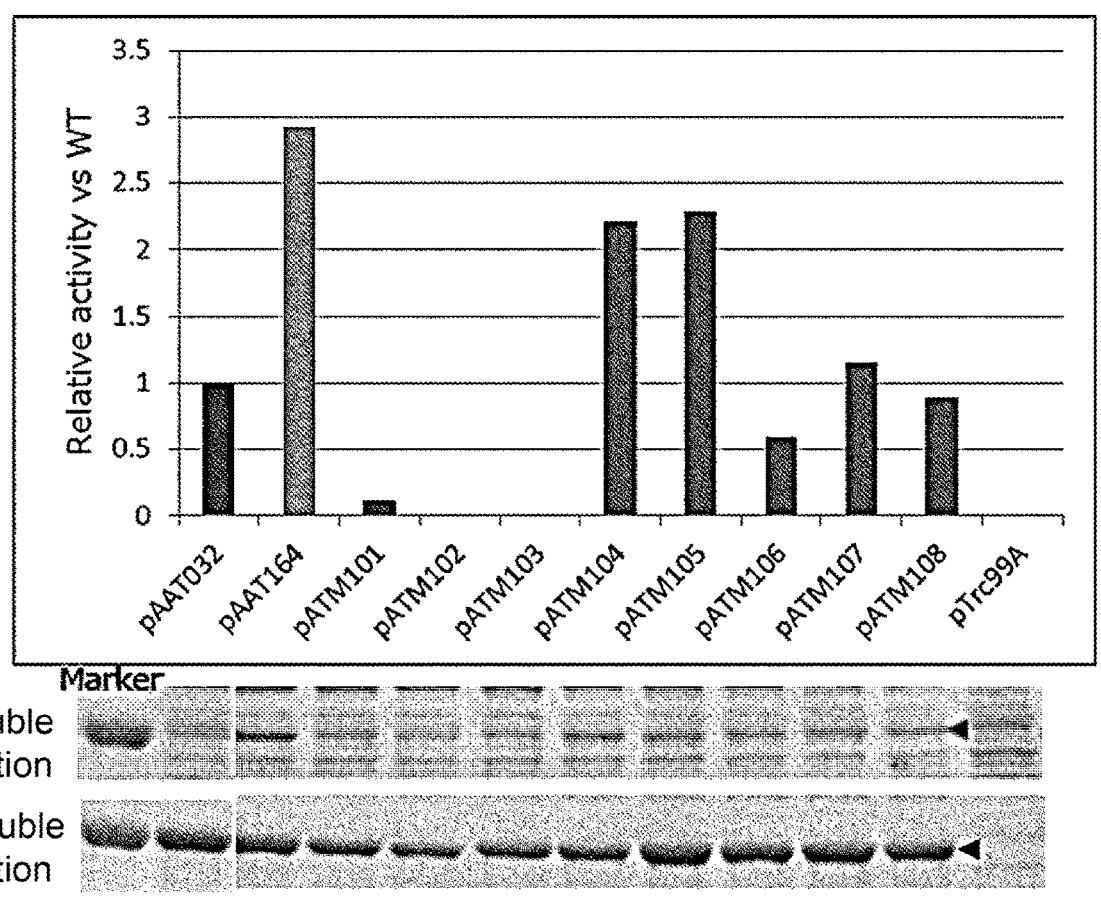

The upper diagram of FIG. 7 is a graph showing results of measuring AAT activity per bacterial cell weight as to recombinants expressing 8 types of mutants prepared by the substitution of 8 cysteine residues of tomato AAT by alanine one by one, and a recombinant expressing a mutant (pAAT164) containing 5 cysteine substitutions introduced in tomato wild-type AAT. The ordinate indicates AAT activity by a relative value when the activity of a recombinant expressing a reference form (pAAT032) is defined as 1. The lower diagrams of FIG. 7 are SDS-polyacrylamide gel electrophoretic patterns of soluble fractions and insoluble fractions from cell extracts containing the mutants.

Figure 8:
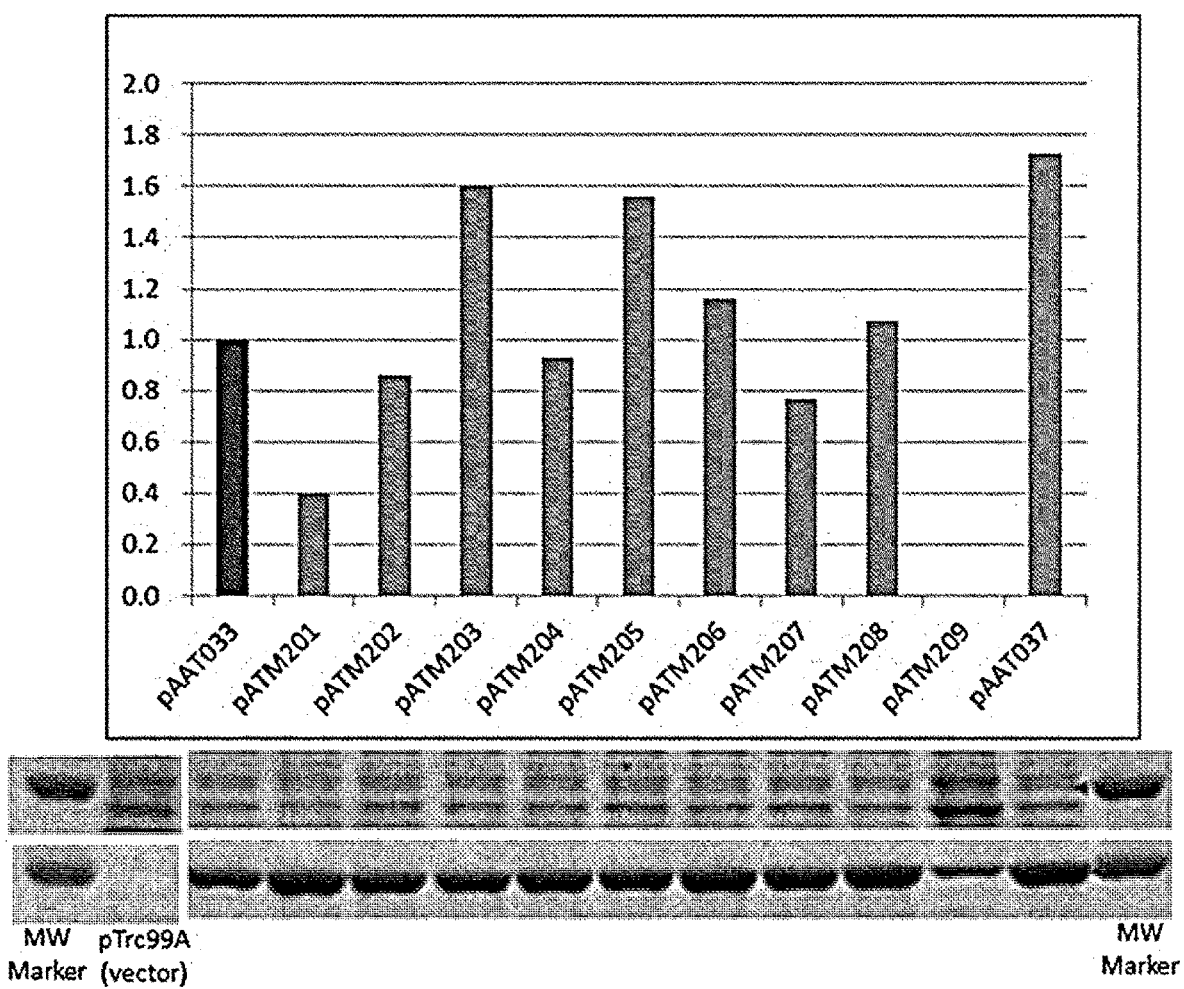

The upper diagram of FIG. 8 is a graph showing results of measuring AAT activity per bacterial cell weight as to recombinants expressing 9 types of mutants prepared by the substitution of 9 cysteine residues of garden strawberry AAT by alanine one by one, and a recombinant expressing a mutant (pAAT037) containing 5 cysteine substitutions introduced in garden strawberry wild-type AAT. The ordinate indicates AAT activity by a relative value when the activity of a recombinant expressing a reference form (pAAT033) is defined as 1. The lower diagrams of FIG. 8 are SDS-polyacrylamide gel electrophoretic patterns of soluble fractions and insoluble fractions from cell extracts containing the mutants.

DESCRIPTION OF EMBODIMENTS

Hereinafter, a preferred mode for carrying out the present invention will be described. Embodiments described below are given for illustrating typical embodiments of the present invention and should not be interpreted as limiting the scope of the present invention.

1. Method for Producing Mutant Enzyme

The present invention relates to a method for producing an enzyme having improved activity per recombinant as compared with a reference form, comprising the step of: expressing a mutant having an amino acid sequence derived from the amino acid sequence of the reference form by the substitution of two or more cysteine residues by other amino acid residues.

Specifically, the method for producing a mutant enzyme according to the present invention comprises the following steps (1) to (3):
(1) preparing recombinants each expressing a mutant having an amino acid sequence derived from the amino acid sequence of the reference form by the substitution of one or more cysteine residues by other amino acid residues;
(2) selecting a plurality of mutants that exhibit 50% or more activity per recombinant relative to 100% activity of the reference form; and
(3) expressing a mutant in which corresponding amino acid residues are substituted at two or more positions among the respective positions of the substituted amino acid residues of the mutants selected in step (2).

[Enzyme]

The enzyme that is subject to the method for producing a mutant enzyme according to the present invention is preferably an enzyme that forms an inclusion body in a transformant (recombinant) when the reference form is expressed in a host different from a species from which the enzyme is derived. The enzyme that is subject to the method for producing a mutant enzyme according to the present invention can be, for example, any plant-derived enzyme that forms an inclusion body in a recombinant cell when the reference form is expressed in a non-plant (e.g., *E. coli*) cell.

Examples of the enzyme include, but are not particularly limited to: transferases such as alcohol acyltransferase (AAT); oxidoreductases such as dehydrogenase, oxidase and oxygenase; hydrolases such as esterase, nitrilase and amidase; isomerases such as racemase, epimerase and mutase; ligases such as acyl-CoA synthase and DNA ligase; and lyases such as nitrile hydrolase, hydroxynitrile lyase and ammonia lyase.

Examples of the origin of the enzyme include animals, plants, filamentous fungi, yeasts, archaebacteria and eubacteria, though the origin of the enzyme is not particularly limited thereto as long as the origin has the features described above.

Examples of the origin of the AAT of the present invention include organisms belonging to any order selected from the group consisting of the order Zingiberales, the order Rosales, the order Ericales, the order Cucurbitales, the order Brassicales, the order Laurales, the order Poales, the order Arecales, the order Asparagales, the order Saxifragales, the order Caryophyllales, the order Vitales, the order Malpighiales, the order Oxalidales, the order Fabales, the order Sapindales, the order Malvales, the order Myrtales, the order Ranunculales, the order Solanales, the order Lamiales, the order Gentianales and the order Asterales. Among them, preferred examples thereof include organisms belonging to any order selected from the group consisting of the order Zingiberales, the order Rosales, the order Ericales, the order Cucurbitales, the order Brassicales and the order Laurales.

The organisms belonging to the order Zingiberales are preferably plants of the family Musaceae and the family Zingiberaceae. The organisms belonging to the order Rosales are preferably plants of the family Rosaceae and the family Moraceae. The organisms belonging to the order Ericales are preferably plants of the family Ericaceae, the family Actinidiaceae, the family Ebenaceae and the family Theaceae. The organisms belonging to the order Cucurbitales are preferably plants of the family Cucurbitaceae. The organisms belonging to the order Brassicales are preferably plants of the family Caricaceae and the family Brassicaceae. The organisms belonging to the order Laurales are preferably plants of the family Lauraceae. The organisms belonging to the order Poales are preferably plants of the family Bromeliaceae and the family Poaceae. The organisms belonging to the order Arecales are preferably plants of the family Arecaceae. The organisms belonging to the order Asparagales are preferably plants of the family Orchidaceae and the family Iridaceae. The organisms belonging to the order Saxifragales are preferably plants of the family Grossulariaceae. The organisms belonging to the order Caryophyllales are preferably plants of the family Caryophyllaceae. The organisms belonging to the order Vitales are preferably plants of the family Vitaceae. The organisms belonging to the order Malpighiales are preferably plants of the family Malpighiaceae, the family Passifloraceae, the family Euphorbiaceae and the family Salicaceae. The organisms belonging to the order Oxalidales are preferably plants of the family Oxalidaceae. The organisms belonging to the order Fabales are preferably plants of the family Fabaceae. The organisms belonging to the order Sapindales are preferably plants of the family Rutaceae, the family Sapindaceae and the family Anacardiaceae. The organisms belonging to the order Malvales are preferably plants of the family Malvaceae. The organisms belonging to the order Myrtales are preferably plants of the family Lythraceae, the family Onagraceae and the family Myrtaceae. The organisms belonging to the order Ranunculales are preferably plants of the family Ranunculaceae and the family Papaveraceae. The organisms belonging to the order Solanales are preferably plants of the family Solanaceae. The organisms belonging to the order Lamiales are preferably plants of the family Oleaceae, the family Verbenaceae and the family Lamiaceae. The organisms belonging to the order Gentianales are preferably plants of the family Apocynaceae. The organisms belonging to the order Asterales are preferably plants of the family Asteraceae. Related species of these plants can also be used. Among them, plants belonging to the family Musaceae, the family Rosaceae, the family Ericaceae, the family Actinidiaceae, the family Cucurbitaceae, the family Caricaceae and the family Lauraceae are more preferred.

Specifically, the plants belonging to the family Musaceae are preferably plants of the genus *Musa*. The plants belonging to the family Zingiberaceae are preferably plants of the genus *Zingiber*. The plants belonging to the family Rosaceae are preferably plants of the genus *Fragaria*, the genus *Malus*, the genus *Prunus*, the genus *Pyrus*, the genus *Eriobotrya*, the genus *Chaenomeles*, the genus *Rubus* and the genus *Rosa*. The plants belonging to the family Moraceae are preferably plants of the genus *Ficus*. The plants belonging to the family Ericaceae are preferably plants of the genus *Vaccinium*. The plants belonging to the family Actinidiaceae are preferably plants of the genus *Actinidia*. The plants belonging to the family Ebenaceae are preferably plants of the genus *Diospyros*. The plants belonging to the family Theaceae are preferably plants of the genus *Camellia*. The plants belonging to the family Cucurbitaceae are preferably plants of the genus *Cucumis* and the genus *Citrullus*. The plants belonging to the family Caricaceae are preferably plants of the genus *Carica* and the genus *Vasconcellea*. The plants belonging to the family Brassicaceae are preferably plants of the genus *Arabidopsis*. The plants belonging to the family Lauraceae are preferably plants of the genus *Persea*. The plants belonging to the family Bromeliaceae are preferably plants of the genus *Ananas*. The plants belonging to the family Poaceae are preferably plants of the genus *Oryza*, the genus *Triticum*, the genus *Hordeum*, the genus *Zea*, the genus *Sorghum* and the genus *Erachypodium*. The plants belonging to the family Arecaceae are preferably plants of the genus *Cocos*. The plants belonging to the family Orchidaceae are preferably plants of the genus *Vanda*. The plants belonging to the family Iridaceae are preferably plants of the genus *Iris*. The plants belonging to the family Grossulariaceae are preferably plants of the genus *Ribes*. The plants belonging to the family Caryophyllaceae are preferably plants of the genus *Gypsophila*. The plants belonging to the family Vitaceae are preferably plants of the genus *Vitis*. The plants belonging to the family Malpighiaceae are preferably plants of the genus *Malpighia*. The plants belonging to the family Passifloraceae are preferably plants of the genus *Passiflora*. The plants belonging to the family Euphorbiaceae are preferably plants of the genus *Ricinus*. The plants belonging to the family Salicaceae are preferably plants of the genus *Populus*. The plants belonging to the family Oxalidaceae are preferably plants of the genus *Averrhoa*. The plants belonging to the family Fabaceae are preferably plants of the genus *Medicago*, the genus *Lupinus*, the genus *Glycine* and the genus *Clitoria*. The plants belonging to the family Rutaceae are preferably plants of the genus *Citrus* and the genus *Aegle*. The plants belonging to the family Sapindaceae are preferably plants of the genus Litchi. The plants belonging to the family Anacardiaceae are preferably plants of the genus *Mangifera*. The plants belonging to the family Malvaceae are preferably plants of the genus *Durio* and the genus *Theobroma*. The plants belonging to the family Lythraceae are preferably plants of the genus *Punica*. The plants belonging to the family Onagraceae are preferably plants of the genus *Clarkia*. The plants belonging to the family Myrtaceae are preferably plants of the genus *Psidium*. The plants belonging to the family Ranunculaceae are preferably plants of the genus *Actaea*. The plants belonging to the family Papaveraceae are preferably plants of the genus *Papaver*. The plants belonging to the family Solanaceae are preferably plants of the genus *Solanum*, the genus *Capsicum*, the genus *Nicotiana* and the genus *Petunia*. The plants belonging to the family Oleaceae are preferably plants of the genus *Olea*. The plants belonging to the family Verbenaceae are preferably plants of the genus *Glandularia*. The plants belonging to the family Lamiaceae are preferably plants of the genus *Salvia*. The plants belonging to the family Apocynaceae are preferably plants of the genus *Rauvolfia* and the genus *Catharanthus*. The plants belonging to the family Asteraceae are preferably plants of the genus *Chamaemelum*. Among them, plants belonging to the genus *Musa*, the genus *Fragaria*, the genus *Malus*, the genus *Prunus*, the genus *Pyrus*, the genus *Vaccinium*, the genus *Actinidia*, the genus *Cucumis*, the genus *Carica* and the genus *Persea* are more preferred.

Among them, plants belonging to the genus *Musa*, the genus *Malus*, the genus *Pyrus*, the genus *Eriobotrya*, the genus *Diospyros*, the genus *Actinidia*, the genus *Cucumis*, the genus *Carica* and the genus *Persea* are particularly preferred.

Further specifically, the plants belonging to the genus *Musa* are particularly preferably *Musa×paradisiaca, Musa basjoo, Musa coccinea* and *Musa acuminate*. The plants belonging to the genus *Zingiber* are particularly preferably *Zingiber officinale*. The plants belonging to the genus *Fragaria* are particularly preferably *Fragaria×ananassa* (hereinafter referred as "garden strawberry"), *Fragaria virginiana, Fragaria chiloensis* and *Fragaria vesca*. The plants belonging to the genus *Malus* are particularly preferably *Malus pumila, Malus domestica* and *Malus baccata, Malus halliana, Malus floribunda* and *Malus prunifolia*. The plants belonging to the genus *Prunus* are particularly preferably *Prunus mume, Prunus avium, Prunus persica, Prunus armeniaca, Prunus dulcis, Prunus salicina* and *Prunus domestica*. The plants belonging to the genus *Pyrus* are particularly preferably *Pyrus communis, Pyrus pyrifolia, Pyrus calleryana, Pyrus pyraster* and *Pyrus×bretschneideri*. The plants belonging to the genus *Eriobotrya* are particularly preferably *Eriobotrya japonica*. The plants belonging to the genus *Chaenomeles* are particularly preferably *Chaenomeles sinensis*. The plants belonging to the genus *Rubus* are particularly preferably *Rubus idaeus* and *Rubus fruticosus*. The plants belonging to the genus *Rosa* are particularly preferably *Rosa rugosa*. The plants belonging to the genus *Ficus* are particularly preferably *Ficus carica*. The plants belonging to the genus *Vaccinium* are particularly preferably *Vaccinium corymbosum* and *Vaccinium angustifolium, Vaccinium myrtillus, Vaccinium vitis-idaea* and *Vaccinium oxycoccos*. The plants belonging to the genus *Actinidia* are particularly preferably *Actinidia chinensis* and *Actinidia deliciosa, Actinidia arguta, Actinidia rufa* and *Actinidia polygama*. The plants belonging to the genus *Diospyros* are particularly preferably *Diospyros kaki*. The plants belonging to the genus *Camellia* are particularly preferably *Camellia sinensis*. The plants belonging to the genus *Cucumis* are particularly preferably *Cucumis sativus, Cucumis melo, Cucumis anguria* and *Cucumis metulifer*. The plants belonging to the genus *Citrullus* are particularly preferably *Citrullus lanatus*. The plants belonging to the genus *Carica* are particularly preferably *Carica papaya*. The plants belonging to the genus *Vasconcellea* are particularly preferably *Vasconcellea cundinamarcensis*.

The plants belonging to the genus *Arabidopsis* are particularly preferably *Arabidopsis thaliana* and *Arabidopsis lyrate*. The plants belonging to the genus *Persea* are particularly preferably *Persea Americana*. The plants belonging to the genus *Ananas* are particularly preferably *Ananas comosus*. The plants belonging to the genus *Oryza* are particularly preferably *Oryza sativa*. The plants belonging to the genus *Triticum* are particularly preferably *Triticum aestivum*. The plants belonging to the genus *Hordeum* are particularly preferably *Hordeum vulgare*. The plants belonging to the genus *Zea* are particularly preferably *Zea mays*. The plants belonging to the genus *Sorghum* are particularly preferably *Sorghum bicolor*. The plants belonging to the genus *Brachypodium* are particularly preferably *Brachypodium distachyon*. The plants belonging to the genus *Cocos* are particularly preferably *Cocos nucifera*. The plants belonging to the genus *Vanda* are particularly preferably *Vanda* hybrid cultivar. The plants belonging to the genus *Iris* are particularly preferably *Iris×hollandica*. The plants belonging to the genus *Ribes* are particularly preferably *Ribes nigrum*. The plants belonging to the genus *Gypsophila* are particularly preferably *Gypsophila paniculata* and *Gypsophila elegans*. The plants belonging to the genus *Vitis* are particularly preferably *Vitis vinifera* and *Vitis labrusca*. The plants belonging to the genus *Malpighia* are particularly preferably *Malpighia glabra*. The plants belonging to the genus *Passiflora* are particularly preferably *Passiflora edulis*. The plants belonging to the genus *Ricinus* are particularly preferably *Ricinus communis*. The plants belonging to the genus *Populus* are particularly preferably *Populus trichocarpa*. The plants belonging to the genus *Averrhoa* are particularly preferably *Averrhoa carambola*. The plants belonging to the genus *Medicago* are particularly preferably *Medicago truncatula*. The plants belonging to the genus *Lupinus* are particularly preferably *Lupinus albus*. The plants belonging to the genus *Glycine* are particularly preferably *Glycine max*. The plants belonging to the genus *Clitoria* are particularly preferably *Clitoria ternatea*. The plants belonging to the genus *Citrus* are particularly preferably *Citrus limon, Citrus sudachi, Citrus sphaerocarpa, Citrus×paradisi, Citrus junos, Citrus aurantifolia, Citrus unshiu* and *Citrus sinensis*. The plants belonging to the genus *Aegle* are particularly preferably *Aegle marmelos*. The plants belonging to the genus *Litchi* are particularly preferably *Litchi chinensis*. The plants belonging to the genus *Mangifera* are particularly preferably *Mangifera indica*. The plants belonging to the genus *Durio* are particularly preferably *Durio zibethinus*. The plants belonging to the genus *Theobroma* are particularly preferably *Theobroma cacao*. The plants belonging to the genus *Punica* are particularly preferably *Punica granatum*.

The plants belonging to the genus *Clarkia* are particularly preferably *Clarkia breweri* (fairy fans) and *Clarkia concinna* (Red ribbons). The plants belonging to the genus *Psidium* are particularly preferably *Psidium guajava*. The plants belonging to the genus *Actaea* are particularly preferably *Actaea racemosa*. The plants belonging to the genus *Papaver* are particularly preferably *Papaver somniferum, Papaver orientale* and *Papaver bracteatum*. The plants belonging to the genus *Solanum* are particularly preferably

*Solanum pennellii* and *Solanum lycopersicum*, and *Solanum tuberosum*. The plants belonging to the genus *Capsicum* are particularly preferably *Capsicum annuum* and *Capsicum chinense*. The plants belonging to the genus *Nicotiana* are particularly preferably *Nicotiana tabacum* and *Nicotiana attenuata*. The plants belonging to the genus *Petunia* are particularly preferably *Petunia×hybrida*. The plants belonging to the genus *Olea* are particularly preferably *Olea europaea*. The plants belonging to the genus *Glandularia* are particularly preferably *Glandularia×hybrida*. The plants belonging to the genus *Salvia* are particularly preferably *Salvia splendens*. The plants belonging to the genus *Rauvolfia* are particularly preferably *Rauvolfia* serpentine. The plants belonging to the genus *Catharanthus* are particularly preferably *Catharanthus roseus*. The plants belonging to the genus *Chamaemelum* are particularly preferably *Chamaemelum nobile*.

Examples of the enzyme that is subject to the method for producing a mutant enzyme according to the present invention particularly include AATs derived from plants such as apples (*Malus* pumila, *Malus domestica* and *Malus baccata*), tomatoes (*Solanum pennellii* and *Solanum lycopersicum*), garden strawberries (*Fragaria×xananassa*), Asian pears (*Pyrus pyrifolia*), loquats (*Eriobotrya japonica*), kaki persimmon (*Diospyros kaki*), melons (*Cucumis melo*), bananas (*Musa×paradisiaca*), papaya (*Carica papaya*), *Clarkia*, grapes (*Vitis vinifera* and *Vitis labrusca*), kiwi fruits (*Actinidia chinensis* and *Actinidia deliciosa*) and Roman chamomile (*Chamaemelum nobile*). Among them, apple-, tomato-, garden strawberry-, Asian pear-, loquat- and kaki persimmon-derived AATs are preferred.

As for apple AAT, examples of the amino acid sequence of the enzyme that may serve as the "reference form" in the method for producing a mutant enzyme according to the present invention are shown in SEQ ID NOs: 1 to 3. SEQ ID NO: 1 represents the amino acid sequence of wild-type AAT. The wild-type apple AAT has 15 cysteine residues in the amino acid sequence. SEQ ID NO: 2 represents the amino acid sequence of mutant AAT derived from the amino acid sequence of the wild-type AAT by the substitution of methionine at position 2 by lysine (M2K mutant AAT). SEQ ID NO: 3 represents the amino acid sequence of mutant AAT derived from the amino acid sequence of the wild-type AAT by the substitution of alanine at position 64 by valine, valine at position 248 by alanine, glutamine at position 363 by lysine, and lysine at position 117 by glutamine (this mutant AAT has higher activity than that of the wild-type AAT).

As for tomato AAT, examples of the amino acid sequence of the enzyme that may serve as the "reference form" in the method for producing a mutant enzyme according to the present invention are shown in SEQ ID NOs: 64 and 66. SEQ ID NO: 66 represents the amino acid sequence of tomato (wild species) wild-type AAT. SEQ ID NO: 64 represents the amino acid sequence of mutant AAT derived from the amino acid sequence of the wild-type AAT by the substitution of alanine at position 2 by lysine (A2K mutant AAT).

As for garden strawberry AAT, an example of the amino acid sequence of the enzyme that may serve as the "reference form" in the method for producing a mutant enzyme according to the present invention is shown in SEQ ID NO: 65. SEQ ID NO: 65 represents the amino acid sequence of wild-type AAT.

[Step (1)]

This step is the step of preparing recombinants each expressing a mutant having an amino acid sequence derived from the amino acid sequence of the reference form by the substitution of one or more cysteine residues by other amino acid residues.

In this step, a plurality of recombinants each expressing a mutant having an amino acid sequence derived from the amino acid sequence of the reference form by the substitution of one or two or more cysteine residues by other amino acid residues are prepared. For example, when the amino acid sequence of the reference form has N cysteine residues, N types of mutants can be prepared in which each cysteine residue is substituted by an amino acid other than cysteine. Alternatively, for example, when the amino acid sequence of the reference form has N cysteine residues, N(N−1)/2 types of mutants can be prepared in which any two cysteine residues are substituted by amino acids other than cysteine.

The number of cysteine residues substituted in one mutant can be 1 or 2 or more and is less than the total number of cysteine residues present in the amino acid sequence of the reference form at the maximum. The number of cysteine residues substituted in one mutant is preferably 1. The number of cysteine residues substituted may be the same or different among a plurality of mutants prepared. The amino acid by which cysteine is to be substituted can be any amino acid other than cysteine and is not particularly limited. The amino acid can be, for example, alanine or arginine.

DNA encoding the amino acid sequence of the mutant can be prepared by introducing a mutation to DNA encoding the amino acid sequence of the reference form according to a conventional genetic engineering approach known in the art. The prepared DNA encoding the amino acid sequence of the mutant is integrated into a conventional general-purpose expression vector.

The expression of the mutant can be performed by transferring the expression vector to a host cell according to a conventional approach known in the art.

Examples of the host cell include, but are not particularly limited to: bacteria such as *E. coli*, the genus *Rhodococcus*, the genus *Pseudomonas*, the genus *Corynebacterium*, the genus *Bacillus*, the genus *Streptococcus* and the genus *Streptomyces*; yeasts such as the genus *Saccharomyces*, the genus *Candida*, the genus *Schizosaccharomyces* and the genus *Pichia*; and filamentous fungi such as the genus *Aspergillus*. Among them, particularly, *E. coli* is preferred because *E. coli* is used conveniently and efficiently.

If necessary, enzymatic activity per recombinant of each mutant prepared in step (1) can be measured.

The measurement of the enzymatic activity per recombinant of the mutant can be performed by preparing a cell extract or a cell homogenate containing the mutant from a given amount of the recombinant harboring the expression vector containing the DNA encoding the amino acid sequence of the mutant, and measuring enzymatic activity in the cell extract or the like. The cell extract or the like can be mixed with an enzymatic reaction substrate, and the amount of a reaction product produced can be detected by use of an approach known in the art such as chromatography to measure enzymatic activity.

[Step (2)]

This step is the step of selecting a plurality of mutants that exhibit 50% or more activity per recombinant relative to 100% activity of the reference form. In this context, the phrase "mutants that exhibit 50% or more activity per recombinant relative to 100% activity of the reference form" means that the amount of a product of reaction catalyzed by a mutant expressed from a given amount of the recombinant is 50% or more of the amount of a product of reaction catalyzed by the reference form expressed from the same amount of the recombinant under the same conditions, due to the high activity and solubility of the mutant.

For example, when the amino acid sequence of the reference form has 10 cysteine residues, each of which is substituted by an amino acid other than cysteine to prepare 10 types of mutants in step (1), mutants that exhibit 50% or more activity per recombinant relative to 100% activity of the reference form are, for example, of 5 types, all of which are selected.

It is considered that among the cysteine residues present in the amino acid sequence of the reference form, cysteine that maintains given enzymatic activity of the mutant even when substituted by another amino acid makes a small contribution to the normal protein folding of the reference form and might rather interfere with the normal protein folding by forming excessive disulfide bonds through the expression of the reference form in host cells different from a species of origin.

The criterion for the selection of the mutant is 50% or more activity per recombinant relative to 100% activity of the reference form as a tolerable index. A mutant that exhibits higher activity, for example, 60% or more, preferably 70% or more, more preferably 80% or more, further preferably 90% or more, most preferably 100% or more activity per recombinant, relative to 100% activity of the reference form may be selected.

[Step (3)]

This step is the step of expressing a mutant in which corresponding amino acid residues are substituted at two or more positions among the respective positions of the substituted amino acid residues of the mutants selected in step (2).

In the aforementioned example in which the amino acid sequence of the reference form has 10 cysteine residues, for example, 5 types of mutants exhibit 50% or more activity per recombinant relative to 100% activity of the reference form. Therefore, a mutant having two or more mutation sites (two or more substitutions of cysteine by other amino acids) among the respective mutation sites (5 positions in total) of these 5 types of mutants is expressed. It is preferred to express a mutant having 3 or more mutation sites, it is more preferred to express a mutant having 4 or more mutation sites, and it is further preferred to express a mutant having all the mutation sites.

As mentioned above, among the cysteine residues present in the amino acid sequence of the reference form, cysteine that maintains given enzymatic activity of the mutant even when substituted by another amino acid might interfere with the normal protein folding through the expression of the reference form in host cells different from a species of origin. It is considered that the mutant in which all of such cysteine residues are substituted by other amino acids undergoes normal or nearly normal folding even when expressed in host cells different from a species of origin, and thereby has higher activity and higher solubility than those of the reference form expressed in the host cells.

The amino acid by which cysteine is to be substituted in the mutant in this step is preferably the same as the amino acid by which cysteine is to be substituted in the mutant selected in step (2), but may be different therefrom. The activity of the recombinant may be further improved by varying types of amino acids by which cysteine is to be substituted.

DNA encoding the amino acid sequence of the mutant in this step can also be prepared by introducing a mutation to DNA encoding the amino acid sequence of the reference form according to a conventional genetic engineering approach known in the art. The prepared DNA encoding the mutant is integrated into a conventional general-purpose expression vector, and a host cell is transfected therewith to express the mutant, in the same way as in step (1).

2. Mutant Alcohol Acyltransferase I

The present invention also provides mutant AAT obtained by the aforementioned method for producing a mutant enzyme.

The mutant AAT according to the present invention is a mutant alcohol acyltransferase having improved activity as compared with a reference form, wherein the mutant alcohol acyltransferase has an amino acid sequence derived from the amino acid sequence of the reference form by the substitution of one or more cysteine residues by other amino acid residues.

The mutant AAT according to the present invention has one or more amino acid substitutions selected from amino acid substitutions given below in the amino acid sequence of the reference form. The reference form can be wild-type apple AAT (SEQ ID NO: 1), mutant AAT (SEQ ID NO: 2, apple M2K mutant) having an amino acid sequence derived from the amino acid sequence of the wild-type apple AAT by the substitution of methionine at position 2 by lysine, or mutant AAT (SEQ ID NO: 3) having an amino acid sequence derived from the amino acid sequence of the wild-type apple AAT by the substitution of alanine at position 64 by valine, valine at position 248 by alanine, glutamine at position 363 by lysine, and lysine at position 117 by glutamine.

(1) A substitution of cysteine at position 48 by another amino acid residue, (2) a substitution of cysteine at position 150 by another amino acid residue, (3) a substitution of cysteine at position 167 by another amino acid residue, (4) a substitution of cysteine at position 270 by another amino acid residue, (5) a substitution of cysteine at position 274 by another amino acid residue, and (6) a substitution of cysteine at position 447 by another amino acid residue.

For the mutant AAT according to the present invention, it is preferred to substitute in combination 2 or more of the cysteine residues at positions 48, 150, 167, 270, 274 and 447, it is more preferred to substitute 3 or more thereof in combination, it is further preferred to substitute 4 or more thereof in combination, it is particularly preferred to substitute 5 or more thereof in combination, and it is most preferred to substitute all of these cysteine residues in combination. The amino acid by which cysteine is to be substituted can be any amino acid other than cysteine and is not particularly limited. The amino acid can be, for example, alanine or arginine. The activity of the mutant AAT can be further improved, particularly, by the substitution of cysteine at position 150 by arginine.

Specific examples of the mutant AAT according to the present invention include mutant AAT consisting of the amino acid sequence represented by SEQ ID NO: 4 or 7, prepared with apple M2K mutant AAT (SEQ ID NO: 2) as the reference form. The mutant AAT having the amino acid sequence of SEQ ID NO: 4 results from the substitution of cysteine at all the positions 48, 150, 167, 270, 274 and 447 of apple M2K mutant AAT (SEQ ID NO: 2) by alanine. The mutant AAT having the amino acid sequence of SEQ ID NO: 7 results from the substitution of cysteine at positions 48, 167, 270, 274 and 447 by alanine and cysteine at position 150 by arginine.

Other specific examples of the mutant AAT according to the present invention include mutant AAT consisting of an amino acid sequence represented by any of SEQ ID NOs: 5, 6, 8 to 11 and 13, prepared with mutant AAT (SEQ ID NO: 3) as the reference form. The introduction positions of mutations and cysteine substitutions in the amino acid sequences of SEQ ID NOs: 5, 6, 8 to 11 and 13 are shown in "Table 1".

TABLE 1

| SEQ ID NO: | Mutation and substitution positions | Remarks |
| --- | --- | --- |
| 5 | A64V, K117Q, V248A, Q363K, C48A, C150A, C167A, C270A, C274A, C447A | Quadruple mutation 6 substitutions |
| 6 | A64V, K117Q, V248A, Q363K, C150R | Quadruple mutation 1 substitutions |
| 8 | A64V, K117Q, V248A, Q363K, C48A, C150A, C270A, C274A, C447A | Quadruple mutation 5 substitutions |
| 9 | A64V, K117Q, V248A, Q363K, C48A, C270A, C274A, C447A | Quadruple mutation 4 substitutions |
| 10 | A64V, K117Q, V248A, Q363K, C48A, C150A, C270A, C274A | Quadruple mutation 4 substitutions |
| 11 | A64V, K117Q, V248A, Q363K, C150A, C270A, C274A, C447A | Quadruple mutation 4 substitutions |
| 13 | A64V, K117Q, V248A, Q363K, C48A, C150A, C270A, C447A | Quadruple mutation 4 substitutions |

In the table described above, alanine at position 64 may be substituted by isoleucine or threonine. Also, glutamine at position 363 may be substituted by proline, alanine, arginine, glycine or tryptophan. In these cases as well, highly active mutant AAT can be obtained.

The mutant AAT according to the present invention has one or more amino acid substitutions selected from amino acid substitutions given below in the amino acid sequence of the reference form. The reference form can be tomato (wild species) wild-type AAT (SEQ ID NO: 66), or mutant AAT (SEQ ID NO: 64, tomato (wild species) A2K mutant) having an amino acid sequence derived from the amino acid sequence of the tomato (wild species) wild-type AAT by the substitution of alanine at position 2 by lysine.
(1) A substitution of cysteine at position 206 by another amino acid residue,
(2) a substitution of cysteine at position 209 by another amino acid residue,
(3) a substitution of cysteine at position 256 by another amino acid residue,
(4) a substitution of cysteine at position 269 by another amino acid residue, and
(5) a substitution of cysteine at position 322 by another amino acid residue.

For the mutant AAT according to the present invention, it is preferred to substitute in combination 2 or more of the cysteine residues at positions 206, 209, 256, 269 and 322, it is more preferred to substitute 3 or more thereof in combination, it is further preferred to substitute 4 or more thereof in combination, and it is most preferred to substitute all of these cysteine residues in combination. The amino acid by which cysteine is to be substituted can be any amino acid other than cysteine and is not particularly limited. The amino acid can be, for example, alanine or arginine.

The mutant AAT according to the present invention has one or more amino acid substitutions selected from amino acid substitutions given below in the amino acid sequence of the reference form. The reference form can be wild-type garden strawberry AAT consisting of the amino acid sequence represented by SEQ ID NO: 65.
(1) A substitution of cysteine at position 115 by another amino acid residue,
(2) a substitution of cysteine at position 167 by another amino acid residue,
(3) a substitution of cysteine at position 179 by another amino acid residue,
(4) a substitution of cysteine at position 325 by another amino acid residue, and
(5) a substitution of cysteine at position 356 by another amino acid residue.

For the mutant AAT according to the present invention, it is preferred to substitute in combination 2 or more of the cysteine residues at positions 115, 167, 179, 325 and 356, it is more preferred to substitute 3 or more thereof in combination, it is further preferred to substitute 4 or more thereof in combination, and it is most preferred to substitute all of these cysteine residues in combination. The amino acid by which cysteine is to be substituted can be any amino acid other than cysteine and is not particularly limited. The amino acid can be, for example, alanine or arginine.

The present invention also provides mutant AAT consisting of an amino acid sequence having 70% or higher, preferably 80% or higher, more preferably 90% or higher, particularly preferably 95% or higher sequence identity to the amino acid sequence of SEQ ID NO: 1 (apple wild-type AAT) or SEQ ID NO: 2 (apple M2K mutant AAT), the mutant AAT having one or more amino acid substitutions selected from the following amino acid substitutions:
(1) a substitution of cysteine corresponding to cysteine at position 48 by another amino acid residue in alignment with the amino acid sequence represented by SEQ ID NO: 1 or 2,
(2) a substitution of cysteine corresponding to cysteine at position 150 by another amino acid residue in alignment with the amino acid sequence represented by SEQ ID NO: 1 or 2,
(3) a substitution of cysteine corresponding to cysteine at position 167 by another amino acid residue in alignment with the amino acid sequence represented by SEQ ID NO: 1 or 2,
(4) a substitution of cysteine corresponding to cysteine at position 270 by another amino acid residue in alignment with the amino acid sequence represented by SEQ ID NO: 1 or 2,
(5) a substitution of cysteine corresponding to cysteine at position 274 by another amino acid residue in alignment with the amino acid sequence represented by SEQ ID NO: 1 or 2, and
(6) a substitution of cysteine corresponding to cysteine at position 447 by another amino acid residue in alignment with the amino acid sequence represented by SEQ ID NO: 1 or 2.

For the mutant AAT according to the present invention, it is preferred to substitute in combination 2 or more of the cysteine residues at positions 48, 150, 167, 270, 274 and 447, it is more preferred to substitute 3 or more thereof in combination, it is further preferred to substitute 4 or more thereof in combination, it is particularly preferred to substitute 5 or more thereof in combination, and it is most preferred to substitute all of these cysteine residues in combination. The amino acid by which cysteine is to be substituted can be any amino acid other than cysteine and is not particularly limited. The amino acid can be, for example, alanine or arginine. The activity of the mutant AAT can be further improved, particularly, by the substitution of cysteine at position 150 by arginine.

The present invention also provides mutant AAT consisting of an amino acid sequence having 70% or higher, preferably 80% or higher, more preferably 90% or higher, particularly preferably 95% or higher sequence identity to the amino acid sequence of SEQ ID NO: 66 (tomato (wild species) AAT) or SEQ ID NO: 64 (tomato (wild species) A2K mutant AAT), the mutant AAT having one or more amino acid substitutions selected from the following amino acid substitutions:
(1) a substitution of cysteine corresponding to cysteine at position 206 by another amino acid residue in alignment with the amino acid sequence represented by SEQ ID NO: 64 or 66,
(2) a substitution of cysteine corresponding to cysteine at position 209 by another amino acid residue in alignment with the amino acid sequence represented by SEQ ID NO: 64 or 66,
(3) a substitution of cysteine corresponding to cysteine at position 256 by another amino acid residue in alignment with the amino acid sequence represented by SEQ ID NO: 64 or 66,
(4) a substitution of cysteine corresponding to cysteine at position 269 by another amino acid residue in alignment with the amino acid sequence represented by SEQ ID NO: 64 or 66, and
(5) a substitution of cysteine corresponding to cysteine at position 322 by another amino acid residue in alignment with the amino acid sequence represented by SEQ ID NO: 64 or 66.

For the mutant AAT according to the present invention, it is preferred to substitute in combination 2 or more of the cysteine residues at positions 206, 209, 256, 269 and 322, it is more preferred to substitute 3 or more thereof in combination, it is further preferred to substitute 4 or more thereof in combination, and it is most preferred to substitute all of these cysteine residues in combination. The amino acid by which cysteine is to be substituted can be any amino acid other than cysteine and is not particularly limited. The amino acid can be, for example, alanine or arginine.

The present invention also provides mutant AAT consisting of an amino acid sequence having 70% or higher, preferably 80% or higher, more preferably 90% or higher, particularly preferably 95% or higher sequence identity to the amino acid sequence of SEQ ID NO: 65 (garden strawberry wild-type AAT), the mutant AAT having one or more amino acid substitutions selected from the following amino acid substitutions:
(1) a substitution of cysteine corresponding to cysteine at position 115 by another amino acid residue in alignment with the amino acid sequence represented by SEQ ID NO: 65,
(2) a substitution of cysteine corresponding to cysteine at position 167 by another amino acid residue in alignment with the amino acid sequence represented by SEQ ID NO: 65,
(3) a substitution of cysteine corresponding to cysteine at position 179 by another amino acid residue in alignment with the amino acid sequence represented by SEQ ID NO: 65,
(4) a substitution of cysteine corresponding to cysteine at position 325 by another amino acid residue in alignment with the amino acid sequence represented by SEQ ID NO: 65, and
(5) a substitution of cysteine corresponding to cysteine at position 356 by another amino acid residue in alignment with the amino acid sequence represented by SEQ ID NO: 65.

For the mutant AAT according to the present invention, it is preferred to substitute in combination 2 or more of the cysteine residues at positions 115, 167, 179, 325 and 356, it is more preferred to substitute 3 or more thereof in combination, it is further preferred to substitute 4 or more thereof in combination, and it is most preferred to substitute all of these cysteine residues in combination. The amino acid by which cysteine is to be substituted can be any amino acid other than cysteine and is not particularly limited. The amino acid can be, for example, alanine or arginine.

The amino acid sequence of AAT to which the substitution of cysteine is to be introduced preferably consists of an amino acid sequence having 50% or higher, 60% or higher or 70% or higher, preferably 80 or higher, more preferably 90% or higher, particularly preferably 95% or higher sequence identity to the amino acid sequence of SEQ ID NO: 1, 2, 64, 65 or 66 in order to enable alignment with the amino acid sequence of SEQ ID NO: 1 (apple wild-type AAT) or SEQ ID NO: 2 (apple M2K mutant AAT), the amino acid sequence of SEQ ID NO: 66 (tomato (wild species) wild-type AAT) or SEQ ID NO: 64 (tomato (wild species) A2K mutant AAT), or the amino acid sequence of SEQ ID NO: 65 (garden strawberry wild-type AAT). The alignment is performed by arranging two sequences to be compared such that as many amino acid residues as possible are identical between the sequences. For the arrangement, a gap is appropriately inserted, if necessary, to one or both of the two sequences to be compared. Such alignment of the sequences can be performed using a well-known program, for example, BLAST, FASTA, or CLUSTALW.

The sequence identity of the amino acid sequence of AAT to which the substitution of cysteine is to be introduced to the amino acid sequence of SEQ ID NO: 1, 2, 64, 65 or 66 is obtained by performing alignment and dividing the number of identical amino acids by the total number of amino acids. In the case of inserting a gap, the total number of amino acids is the number of residues counted with one gap as one amino acid residue. When the total number of amino acids thus counted differs between the two sequences to be compared, the identity (%) is calculated by dividing the number of identical amino acids by the total number of amino acids of the longer sequence.

AAT consisting of an amino acid sequence having high sequence identity to the amino acid sequence of SEQ ID NO: 1 (apple wild-type AAT) or SEQ ID NO: 2 (apple M2K mutant AAT) is likely to conserve cysteine at positions 48, 150, 167, 270, 274 and 447 found in the amino acid sequence of SEQ ID NO: 1 (apple wild-type AAT) or SEQ ID NO: 2 (apple M2K mutant AAT). It is considered that these cysteine residues may be substituted by other amino acids to obtain a highly active mutant for various AATs (preferably plant-derived various AATs).

For example, AAT that exhibits 88% sequence identity to the amino acid sequence of SEQ ID NO: 1 (apple wild-type AAT) is apple AAT consisting of the amino acid sequence represented by SEQ ID NO: 12 derived from a different subspecies of the genus *Malus*. All the cysteine residues at positions 48, 150, 167, 270, 274 and 447 among the cysteine residues found in the amino acid sequence of SEQ ID NO: 1 (apple wild-type AAT) are conserved in the amino acid sequence represented by SEQ ID NO: 12.

AAT that exhibits 91% sequence identity to the amino acid sequence of SEQ ID NO: 1 (apple wild-type AAT) is Asian pear AAT consisting of the amino acid sequence represented by SEQ ID NO: 61. All the cysteine residues at positions 48, 150, 167, 270 and 274 among the cysteine residues found in the amino acid sequence of SEQ ID NO:

1 (apple wild-type AAT) are conserved in the amino acid sequence represented by SEQ ID NO: 61.

AAT that exhibits 91% sequence identity to the amino acid sequence of SEQ ID NO: 1 (apple wild-type AAT) is loquat AAT consisting of the amino acid sequence represented by SEQ ID NO: 62. All the cysteine residues at positions 48, 150, 167, 270, 274 and 447 among the cysteine residues found in the amino acid sequence of SEQ ID NO: 1 (apple wild-type AAT) are conserved in the amino acid sequence represented by SEQ ID NO: 62.

In addition, AAT that exhibits 90% sequence identity to the amino acid sequence of SEQ ID NO: 1 (apple wild-type AAT) is kaki persimmon AAT consisting of the amino acid sequence represented by SEQ ID NO: 63. All the cysteine residues at positions 150, 167, 270, 274 and 447 among the cysteine residues found in the amino acid sequence of SEQ ID NO: 1 (apple wild-type AAT) are conserved in the amino acid sequence represented by SEQ ID NO: 63.

Figure 1:
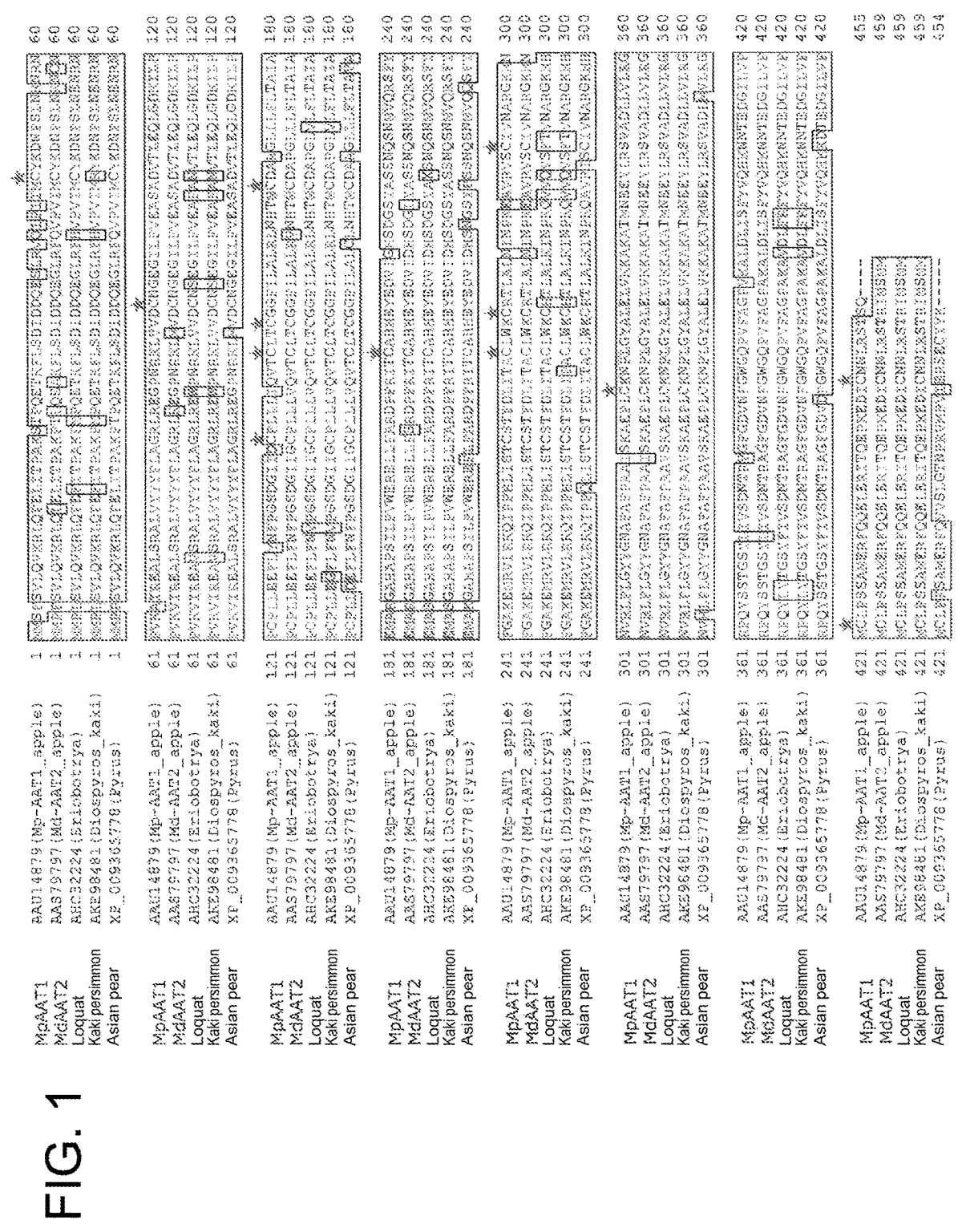

The alignment of the amino acid sequences of SEQ ID NOs: 1, 12 and 61 to 63 is shown in FIG. 1.

AAT consisting of an amino acid sequence having high sequence identity to the amino acid sequence of SEQ ID NO: 66 (tomato (wild species) wild-type AAT) or SEQ ID NO: 64 (tomato (wild species) A2K mutant AAT) is likely to conserve cysteine at positions 206, 209, 256, 269 and 322 found in the amino acid sequence of the tomato (wild species) wild-type AAT or the tomato (wild species) A2K mutant AAT. It is considered that these cysteine residues may be substituted by other amino acids to obtain a highly active mutant for various AATs (preferably plant-derived various AATs).

For example, AAT that exhibits 93% sequence identity to the amino acid sequence of SEQ ID NO: 66 (tomato (wild species) wild-type AAT) is tomato AAT consisting of the amino acid sequence represented by SEQ ID NO: 67 derived from a tomato (cultivated species). All the cysteine residues at positions 209, 256, 269 and 322 among the cysteine residues found in the amino acid sequence of the tomato (wild species) wild-type AAT are conserved in the amino acid sequence represented by SEQ ID NO: 67.

AAT that exhibits 84% sequence identity to the amino acid sequence of SEQ ID NO: 66 (tomato (wild species) wild-type AAT) is potato AAT consisting of the amino acid sequence represented by SEQ ID NO: 68. All the cysteine residues at positions 206, 209, 256, 269 and 322 among the cysteine residues found in the amino acid sequence of the tomato (wild species) wild-type AAT are conserved in the amino acid sequence represented by SEQ ID NO: 68.

AAT that exhibits 78% sequence identity to the amino acid sequence of SEQ ID NO: 66 (tomato (wild species) wild-type AAT) is pepper AAT consisting of the amino acid sequence represented by SEQ ID NO: 69. All the cysteine residues at positions 206, 209, 269 and 322 among the cysteine residues found in the amino acid sequence of the tomato (wild species) wild-type AAT are conserved in the amino acid sequence represented by SEQ ID NO: 69.

In addition, AAT that exhibits 74% sequence identity to the amino acid sequence of SEQ ID NO: 66 (tomato (wild species) wild-type AAT) is tobacco AAT consisting of the amino acid sequence represented by SEQ ID NO: 70. All the cysteine residues at positions 206, 209 and 322 among the cysteine residues found in the amino acid sequence of the tomato (wild species) wild-type AAT are conserved in the amino acid sequence represented by SEQ ID NO: 70.

Figure 2:
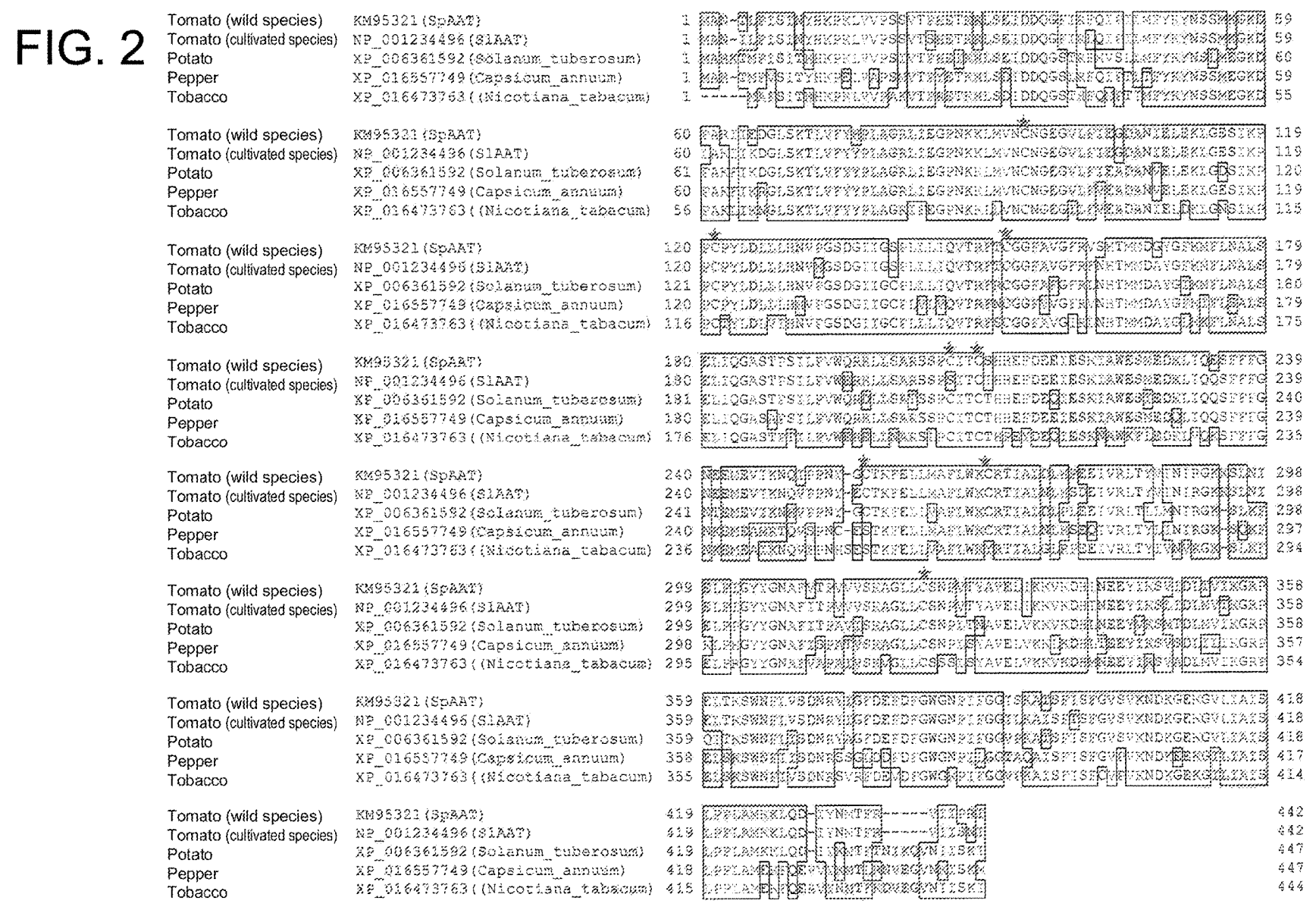

The alignment of the amino acid sequences of SEQ ID NOs: 66 to 70 is shown in FIG. 2.

AAT consisting of an amino acid sequence having high sequence identity to the amino acid sequence of SEQ ID NO: 65 (garden strawberry wild-type AAT) is likely to conserve cysteine at positions 115, 167, 179, 325 and 356 found in the amino acid sequence of the garden strawberry wild-type AAT. It is considered that these cysteine residues may be substituted by other amino acids to obtain a highly active mutant for various AATs (preferably plant-derived various AATs).

For example, AAT that exhibits 94% sequence identity to the amino acid sequence of SEQ ID NO: 65 (garden strawberry wild-type AAT) is beach strawberry AAT consisting of the amino acid sequence represented by SEQ ID NO: 71. All the cysteine residues at positions 115, 167, 179, 325 and 356 among the cysteine residues found in the amino acid sequence of the garden strawberry wild-type AAT are conserved in the amino acid sequence represented by SEQ ID NO: 71.

For example, AAT that exhibits 91% sequence identity to the amino acid sequence of SEQ ID NO: 65 (garden strawberry wild-type AAT) is woodland strawberry AAT consisting of the amino acid sequence represented by SEQ ID NO: 72. All the cysteine residues at positions 115, 167, 179, 325 and 356 among the cysteine residues found in the amino acid sequence of the garden strawberry wild-type AAT are conserved in the amino acid sequence represented by SEQ ID NO: 71.

For example, AAT that exhibits 67% sequence identity to the amino acid sequence of SEQ ID NO: 65 (garden strawberry wild-type AAT) is Japanese rose AAT consisting of the amino acid sequence represented by SEQ ID NO: 73. All the cysteine residues at positions 167, 325 and 356 among the cysteine residues found in the amino acid sequence of the garden strawberry wild-type AAT are conserved in the amino acid sequence represented by SEQ ID NO: 73.

Figure 3:
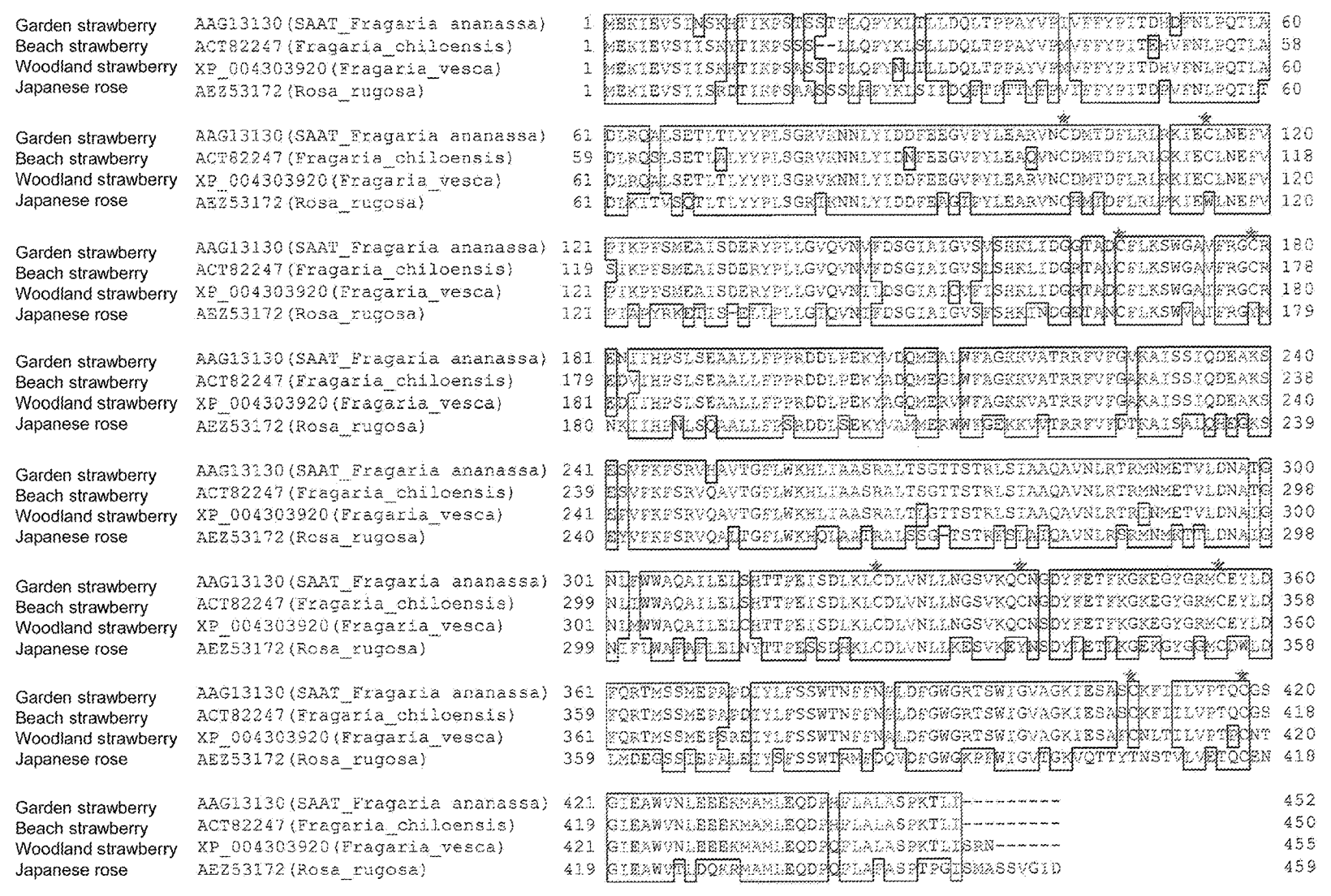

The alignment of the amino acid sequences of SEQ ID NOs: 65 and 71 to 73 is shown in FIG. 3.

3. Mutant Alcohol Acyltransferase II

The present invention also provides mutant AAT having substitution(s) of alanine at position 64, valine at position 248, glutamine at position 363 and/or lysine at position 117 in the amino acid sequence of apple wild-type AAT or apple M2K mutant AAT. This mutant AAT exhibits higher activity and solubility than those of the wild-type AAT.

Specifically, the mutant AAT according to the present invention has one or more amino acid substitutions selected from the following amino acid substitutions in the amino acid sequence represented by SEQ ID NO: 1 or 2:

(1) a substitution of alanine at position 64 by valine, isoleucine or threonine,
(2) a substitution of lysine at position 117 by glutamine,
(3) a substitution of valine at position 248 by alanine, and
(4) a substitution of glutamine at position 363 by lysine, proline, alanine, arginine, glycine or tryptophan.

For the mutant AAT according to the present invention, it is preferred to substitute in combination 2 or more of the alanine at position 64, the lysine at position 117, the valine at position 248 and the glutamine at position 363, it is more preferred to substitute 3 or more thereof in combination, and it is most preferred to substitute all of these residues in combination.

Specific examples of the mutant AAT according to the present invention include mutant alcohol acyltransferases consisting of an amino acid sequence represented by any of SEQ ID NOs: 3, 5, 6 and 8 to 13 (see Table 1).

It is considered that the high activation of the aforementioned apple mutant AAT by the introduction of a mutation is also applicable to various AATs (preferably various plant-derived AATs) consisting of an amino acid sequence having high sequence identity to the amino acid sequence of SEQ ID NO: 1 (apple wild-type AAT) or SEQ ID NO: 2 (apple M2K mutant AAT).

Thus, the present invention provides mutant AAT consisting of an amino acid sequence having 70% or higher, preferably 80 or higher, more preferably 90% or higher, particularly preferably 95% or higher sequence identity to the amino acid sequence of SEQ ID NO: 1 (apple wild-type AAT) or SEQ ID NO: 2 (apple M2K mutant AAT), the mutant AAT having one or more amino acid substitutions selected from the following amino acid substitutions:

(1) a substitution of an amino acid residue corresponding to alanine at position 64 by valine, isoleucine or threonine in alignment with the amino acid sequence represented by SEQ ID NO: 1 or 2, (2) a substitution of an amino acid corresponding to lysine at position 117 by glutamine in alignment with the amino acid sequence represented by SEQ ID NO: 1 or 2, (3) a substitution of an amino acid corresponding to valine at position 248 by alanine in alignment with the amino acid sequence represented by SEQ ID NO: 1 or 2, and (4) a substitution of an amino acid corresponding to glutamine at position 363 by lysine, proline, alanine, arginine, glycine or tryptophan in alignment with the amino acid sequence represented by SEQ ID NO: 1 or 2.

For the mutant AAT according to the present invention, it is preferred to substitute in combination 2 or more of the amino acid residue corresponding to alanine at position 64, the amino acid residue corresponding to lysine at position 117, the amino acid residue corresponding to valine at position 248 and the amino acid residue corresponding to glutamine at position 363, it is more preferred to substitute 3 or more thereof in combination, and it is most preferred to substitute all of these residues in combination.

All of lysine at position 117, valine at position 248 and glutamine at position 363 found in the amino acid sequence of SEQ ID NO: 1 (apple wild-type AAT) or SEQ ID NO: 2 (apple M2K mutant AAT) are conserved in the amino acid sequences represented by SEQ ID NOs: 12, 61, 62 and 63. Thus, it is considered that these amino acids may be substituted by isoleucine or threonine; glutamine; alanine; and lysine, proline, alanine, arginine, glycine or tryptophan, respectively, to obtain a highly active mutant for various AATs (preferably plant-derived AATs, particularly preferably AATs derived from various plants of the genus *Malus*). The amino acid sequence of AAT to which the substitution of the amino acid is to be introduced preferably consists of an amino acid sequence having 50% or higher, 60% or higher or 70% or higher, preferably 80 or higher, more preferably 90% or higher, particularly preferably 95% or higher sequence identity to the amino acid sequence of SEQ ID NO: 1 or 2 in order to enable alignment with the amino acid sequence of SEQ ID NO: 1 (apple wild-type AAT) or SEQ ID NO: 2 (apple M2K mutant AAT).

4. Vector and Transformant

An expression vector for the mutant AAT according to the present invention or having an insert of DNA encoding the mutant AAT can be prepared by use of a conventional genetic engineering approach known in the art.

The vector can be any vector capable of autonomously replicating in a host cell, and a vector suitable for the host cell can be used. The insertion of the mutant AAT gene to the vector can be performed by use of a gene recombination technique known to those skilled in the art. For example, a method using restriction enzyme cleavage and a ligation kit, a method using topoisomerase, or In Fusion kit (Takara Bio Inc.) can be used. The gene to be inserted to the vector is inserted by linking to downstream of a promoter capable of regulating transcription and translation into a protein encoded by the gene in a host cell. For the insertion, an appropriate linker may be added, if necessary. Also, a terminator sequence, an enhancer sequence, a splicing signal sequence, a poly-A addition signal sequence, a ribosomal binding sequence (e.g., an SD sequence and a Kozak sequence), a selective marker gene, and the like available in a host organism to which the gene is to be transferred can be linked, if necessary. Examples of the selective marker gene can include: drug resistance genes such as ampicillin resistance gene, tetracycline resistance gene, neomycin resistance gene, kanamycin resistance gene and chloramphenicol resistance gene; genes involved in the intracellular biosynthesis of nutrients such as amino acids and nucleic acids; and genes encoding fluorescent proteins such as luciferase. In association with the insertion, the amino acid sequence encoded by the DNA may be partially substituted.

The vector is transferred to a host cell by a method known to those skilled in the art, and used in the preparation of a transformant. The method for transferring the vector to the host cell is not particularly limited as long as the method is suitable for the host cell. Examples thereof include electroporation, spheroplast method, lithium acetate method and conjugational transfer method.

Examples of the host cell include, but are not particularly limited to: bacteria such as *E. coli*, the genus *Rhodococcus*, the genus *Pseudomonas*, the genus *Corynebacterium*, the genus *Bacillus*, the genus *Streptococcus* and the genus *Streptomyces*; yeasts such as the genus *Saccharomyces*, the genus *Candida*, the genus *Schizosaccharomyces* and the genus *Pichia*; and filamentous fungi such as the genus *Aspergillus*. Among them, particularly, *E. coli* is preferred because *E. coli* is used conveniently and efficiently.

EXAMPLES

Reference Example 1: Preparation of Apple AAT (MpAAT1) Gene Expression Plasmids pAAT012, pAAT115 and pAAT116

3 types of plasmids for the expression of the apple AAT (MpAAT1) gene were prepared.

The plasmid pAAT012 contains a gene encoding wild-type apple AAT (SEQ ID NO: 1).

The plasmid pAAT115 contains a gene encoding engineered apple AAT derived from the wild-type apple AAT by the substitution of an amino acid methionine at position 2 by valine.

The plasmid pAAT116 contains a gene encoding engineered apple AAT (SEQ ID NO: 2) derived from the wild-type apple AAT by the substitution of an amino acid methionine at position 2 by lysine.

First, the wild-type apple AAT gene (SEQ ID NO: 14) optimized for *E. coli* codons was synthesized (consigned to DNA2.0). The AAT gene was inserted to an expression vector (pJexpress404). The resulting vector was designated as pAAT012.

The AAT gene was transferred from the expression vector (pJexpress404) having T7 promoter to an expression vector (pTrc99A) having trc promoter by the following method.

A fragment containing the AAT gene was amplified by PCR reaction with pAAT012 as a template using primers MMA-156 and MMA-163. In this operation, codon ATG for Met at position 2 of the AAT gene was converted to GTG (Val) in order to introduce a NcoI restriction enzyme site.

```
Primer MMA-156 (SEQ ID NO: 15):
CACAGGAAACAGACCATGGTGAGCTTTTCTGTACTCCAAGTCAAACG Primer MMA-163 (SEQ ID NO: 16):
GCCAAGCTTGCATGCCTGCAGGTTACTGGCTGGTGCTACGCAG
```

The amplification product was purified using Gel/PCR Purification Kit (manufactured by FAVORGEN Biotech Corp.), and the resultant was used as an insertion fragment. A vector pTrc99A cleaved in advance with restriction enzymes NcoI and Sse8387I was mixed with the insertion fragment and ligated therewith using In-Fusion HD Cloning Kit.

The reaction solution was incubated at 50° C. for 15 minutes, then cooled on ice, and used in the transformation of an *E. coli* JM109 strain. The *E. coli* transformant was liquid-cultured in LB medium containing 100 mg/L ampicillin (LBAmp medium). The plasmid pAAT115 of interest was prepared using Mini prep Kit (Qiagen N.V.).

The amino acid residue at position 2 of the gene product of the apple AAT gene inserted in pAAT115 is valine. The case is known where the expression level of a protein is improved by the substitution of the amino acid residue at position 2 by lysine, arginine or the like (Japanese Patent Laid-Open No. 2008-61547). Accordingly, the codon for the amino acid at position 2 of the AAT gene was converted as follows.

First, pAAT115 was cleaved with NcoI and SmaI to prepare a fragment containing a vector region of approximately 5.1 kb.

A fragment (approximately 400 bp) containing the AAT gene was amplified by PCR reaction with pAAT115 as a template using primers MMA-166 and MMA-169, and purified by the aforementioned method to obtain an insertion fragment.

```
Primer MMA-166 (SEQ ID NO: 17):
CACAGGAAACAGACCATGAAAAGCTTTTCTGTACTCCAAGTC

Primer MMA-169 (SEQ ID NO: 18):
CGATGATACCATCGCTGCCCGGGAAGTTGTACAG
```

The fragment containing the vector region was ligated with the insertion fragment using In-Fusion HD Cloning Kit, followed by the transformation of an *E. coli* JM109 strain. The *E. coli* transformant (recombinant) was liquid-cultured to prepare the plasmid pAAT116 of interest. In pAAT116, codon GTG for Val at position 2 of the AAT gene was substituted by AAA (Lys).

Example 1: Production of Highly Active Apple AAT (1) Preparation of Recombinant Expressing Mutant in which Cysteine Residue was Substituted by Alanine Residue The protein encoded by the apple AAT gene in the plasmid pAAT116 prepared in Reference Example 1 has 15 cysteine residues. 15 plasmids in which each cysteine was substituted by alanine was synthesized by consignment (GenScript Biotech Corp.) (Table 2).

TABLE 2

| Plasmid name | Position of substituted cysteine residue | Codon |
| --- | --- | --- |
| pAAT116 | — | CTG |
| pAAT116C48A | Position 48 | GCG |
| pAAT116C95A | Position 95 | GCG |
| pAAT116C122A | Position 122 | GCG |
| pAAT116C141A | Position 141 | GCG |
| pAAT116C150A | Position 150 | GCG |
| pAAT116C153A | Position 153 | GCG |
| pAAT116C167A | Position 167 | GCG |
| pAAT116C210A | Position 210 | GCG |
| pAAT116C261A | Position 261 | GCG |
| pAAT116C270A | Position 270 | GCG |
| pAAT116C274A | Position 274 | GCG |
| pAAT116C291A | Position 291 | GCG |
| pAAT116C326A | Position 326 | GCG |
| pAAT116C422A | Position 422 | GCG |
| pAAT116C447A | Position 447 | GCG |

An *E. coli* JM109 strain was transformed with each of 16 plasmids shown in "Table 2". The *E. coli* transformant was inoculated to LB (1% Bacto Tryptone, 0.5% Bacto Yeast Extract, 1% NaCl) medium containing ampicillin and pre-cultured at 37° C. for 7 hours. A 0.1 ml aliquot of the culture solution was added to 100 ml of the same medium (containing 1 mM IPTG) and shake-cultured at 37° C. for 15 hours. Bacterial cells were recovered from the culture solution, washed with a 50 mM sodium phosphate buffer solution (pH 7.0), and then suspended in the same buffer solution.

(2) Preparation of Cell Extract Containing Mutant

The obtained bacterial cell suspension was adjusted to OD630 of 10. The cells were homogenized by ultrasonic treatment, and bacterial cells and membrane fractions were removed by centrifugation to prepare a cell extract.

(3) AAT Activity Measurement of Cell Extract Containing Mutant 0.2 ml of the cell extract was added to 0.8 ml of a reaction solution containing 1 mM methacryl-CoA and 40 mM n-butanol to start production reaction of methacrylic acid ester. The reaction was performed in a 10 ml septum sample bottle (for GC). The sample bottle was incubated at 30° C. for 1 to 2 hours so that the reaction proceeded. After the completion of the reaction, 1 ml of acetonitrile was added to the reaction solution in the sample bottle and mixed therewith. Then, the mixture was filtered through a syringe filter DISMIC (pore size: 0.45 μm, manufactured by Advantec) and then subjected to HPLC analysis.

Figure 4:
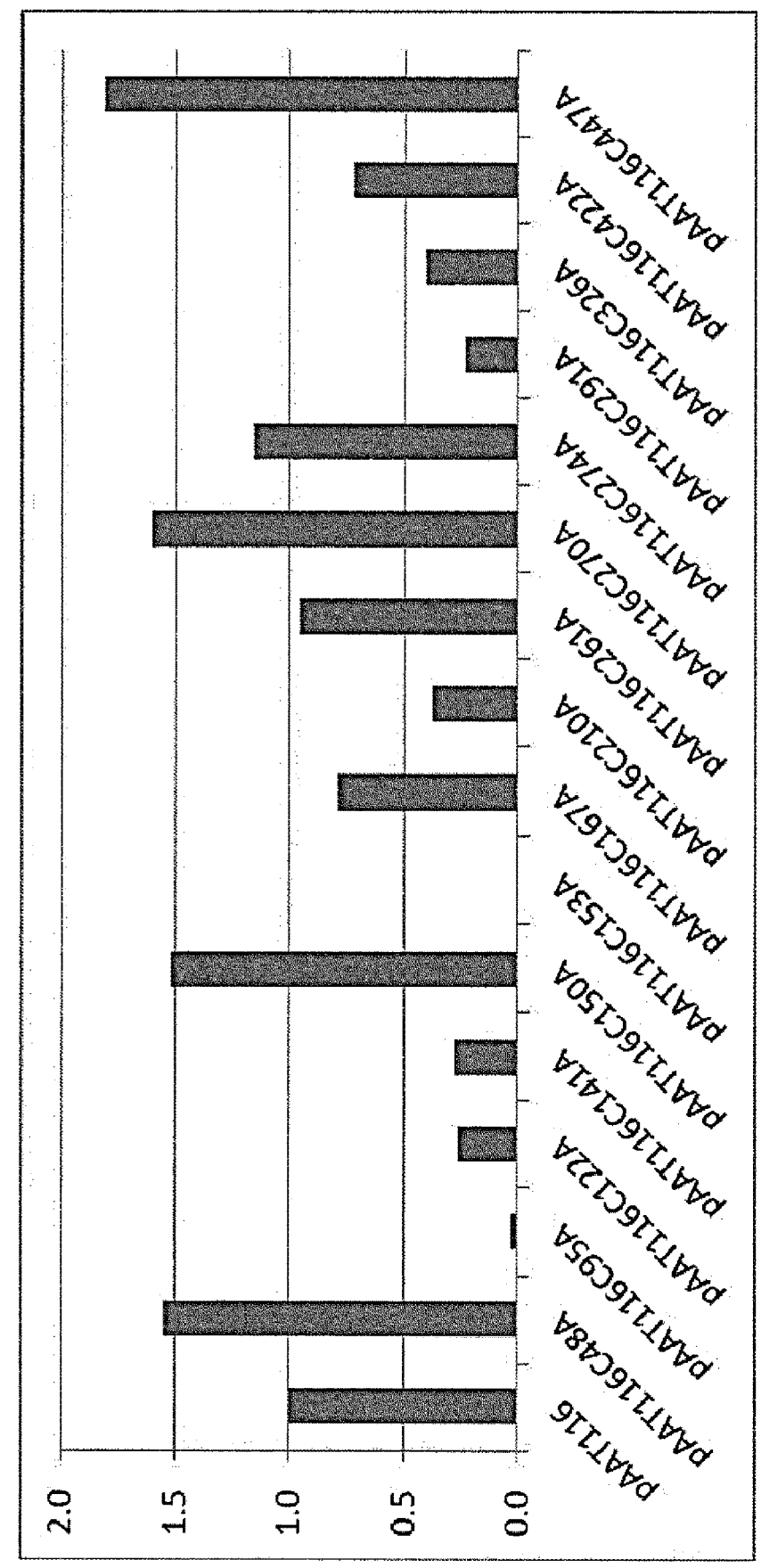
FIG. 4 is a graph showing results of measuring AAT activity as to recombinants expressing 15 types of mutants prepared by the substitution of 15 cysteine residues of apple AAT by alanine one by one. The ordinate indicates AAT activity per bacterial cell weight by a relative value when the activity of a recombinant expressing a reference form (pAAT116) having no cysteine substitution is defined as 1.

HPLC Analysis Conditions:
Apparatus: Waters 2695
Column: Shiseido CAPCELL PAK C18 UG120 5 μm
Mobile phase: 65% MeOH and 0.2% phosphoric acid
Flow rate: 0.25 ml/min
Column temperature: 35° C.
Detection: UV 210 nm
Injection volume: 10 μL The results are shown in FIG. 4. Eight mutants that exhibited 50% or more AAT activity per recombinant relative to 100% activity of the reference form expressed from pAAT116 were obtained, and among them, mutants expressed from pAAT116C48A, pAAT116C150A, pAAT116C167A, pAAT116C270A, pAAT116C274A and pAAT116C447A exhibited 70% or more AAT activity per recombinant relative to 100% activity of the reference form expressed from pAAT116. Accordingly, a mutant containing all the amino acid substitutions C48A, C150A, C167A, C270A, C274A and C447A of these 6 mutants was prepared.

In this context, the "AAT activity" means the activity of catalyzing the production of an ester from a CoA compound. The phrase "mutants that exhibit 50% or more AAT activity per recombinant relative to 100% activity of the reference form" means that the amount of the ester produced through the catalysis of a mutant expressed from a given amount of the *E. coli* recombinant is 50% or more of the amount of the ester produced through the catalysis of the reference form expressed from the *E. coli* recombinant under the same conditions, due to the high activity and solubility of the mutant.

(4) Preparation of Recombinant Expressing Mutant in which 6 Cysteine Residues were Substituted by Alanine Residues The AAT gene encoding a mutant in which all the cysteine residues 48, 150, 167, 270, 274 and 447 were substituted by alanine was synthesized by consignment (GenScript Biotech Corp.) and inserted to a vector pTrc99A to obtain a plasmid pAAT024.

A cell extract containing the mutant was prepared by the aforementioned method, and the AAT activity of the cell extract was measured. Further, the cell extract (soluble fraction) and an insoluble fraction (bacterial cells and membrane fractions) separated from the cell extract by centrifugation were separated by SDS-polyacrylamide gel electrophoresis, and a band of the recombinant AAT protein was detected.

The results are shown in FIG. 5. The ordinate of the graph indicates AAT activity per bacterial cell weight when the AAT activity of the reference form expressed from pAAT116 is defined as 1. The mutant expressed from pAAT024 exhibited AAT activity per recombinant of approximately 5 times the activity of the reference form. Also, the mutant expressed from pAAT024 was more abundant in the soluble fraction as compared with the reference form. These results demonstrated that the substitution of cysteine residues 48, 150, 167, 270, 274 and 447 by alanine enhances the solubility of AAT and improves activity per recombinant.

Reference Example 2: Screening for Highly Soluble Mutant Using AAT-Chloramphenicol (CAT) Fusion Protein In order to obtain a highly soluble mutant of apple AAT, a random mutation library of the AAT gene was first prepared. Next, an expression plasmid library including a mutated AAT-CAT fusion gene was prepared by linking the mutant AAT gene to chloramphenicol (CAT) resistance gene. *E. coli* transformants obtained by transformation with the library were screened for highly soluble AAT with chloramphenicol resistance as an index. Provided that the solubility of the AAT protein is improved, the solubility of the AAT-chloramphenicol fusion protein is also improved and as a result, the chloramphenicol resistance of the *E. coli* transformant is improved. Specifically, the following procedures were performed.

(1) Preparation of Random Mutation Gene Library

An amplification fragment (1.4 kb) was obtained by PCR with pAAT116 as a template using GeneMorph II Random Mutagenesis Kit (Stratagene California) and primers MMA-185 and MMA-157.

```
Primer MMA-185 (SEQ ID NO: 19):
GGATCATGAAAAGCTTTTCTGTACTCCAAGTC
```

```
Primer MMA-157 (SEQ ID NO: 20):
GTGATTTTTTTCTCCGCACTAGTCTACTGGCTGGTGCTACGCAG
```

The amplification fragment was treated with restriction enzymes BspHI and SpeI. The fragment was separated by agarose gel electrophoresis and then extracted from the gel using Gel/PCR Purification Kit (FAVORGEN Biotech Corp.). The resultant was used as a random mutation gene library (mutated AAT (M2K) gene library).

(2) Preparation of Expression Plasmid pAAT113 Containing AAT-CAT Fusion Gene

Preparation of plasmid vector pSTV28N The CAT gene used was derived from a plasmid vector pSTV28 (Takara Bio Inc.). This CAT gene has a NcoI restriction enzyme site, which is however inconvenient for the subsequent preparation of a library. Therefore, the sequence of the NcoI site was converted to a sequence uncleavable by NcoI. The conversion was performed by PCR reaction with a plasmid pSTV28 as a template as follows.

```
Forward primer MMA-152 (SEQ ID NO: 21):
GCCCCCGTTTTCACGATGGGCAAATAT
```

```
Reverse primer MMA-153 (SEQ ID NO: 22):
ATATTTGCCCATCGTGAAAACGGGGGC
```

0.5 µl of DpnI was added to 12.5 µl of the PCR reaction solution, and the mixture was incubated at 37° C. for 1 hour. An *E. coli* JM109 strain was transformed with the reaction solution thus treated. A plasmid was prepared from the *E. coli* transformant and designated as pSTV28N.

Preparation of Plasmid pAAT113 for Expression of AAT-CAT Fusion Gene

An AAT gene fragment was amplified by PCR with the plasmid pAAT012 described in Reference Example 1 as a template using primers MMA-156 and MMA-157, and then purified.

```
Primer MMA-156 (SEQ ID NO: 23):
CACAGGAAACAGACCATGGTGAGCTTTTCTGTACTCCAAGTCAAACG
```

```
Primer MMA-157 (SEQ ID NO: 24):
GTGATTTTTTTCTCCGCACTAGTCTACTGGCTGGTGCTACGCAG
```

A CAT gene fragment was amplified by PCR with pSTV28N as a template using primers MMA-159 and MMA-160, and then purified.

```
Primer MMA-159 (SEQ ID NO: 25):
CTGCGTAGCACCAGCCAGTAGACTAGTGCGGAGAAAAAAATCAC
```

```
Primer MMA-160 (SEQ ID NO: 26):
GCCAAGCTTGCATGCCTGCAGGTTACGCCCCGCCCTGCCACTCATCG
```

The AAT gene fragment and the CAT gene fragment were mixed with a vector pTrc99A cleaved in advance with NcoI and Sse8387I, and these 3 fragments were ligated using In-Fusion HD Cloning Kit. An *E. coli* JM109 strain was transformed with the reaction solution. A plasmid was prepared from the *E. coli* transformant and designated as pAAT113. The amino acid at position 2 of the protein encoded by the AAT gene in pAAT113 is valine.

Preparation of Plasmid pAAT117 for Expression of AAT (V2K)-CAT Fusion Gene

The amino acid valine at position 2 of the protein encoded by the AAT gene in pAAT113 was converted to lysine to prepare a plasmid pAAT117. The amino acid substitution was performed in accordance with the preparation of pAAT116 from pAAT115 in Reference Example 1.

(3) Preparation of Mutated AAT-CAT Fusion Gene Plasmid Library pAAT113 was cleaved with NcoI and SpeI and then treated with SAP (shrimp alkaline phosphatase). The DNA fragment was purified using agarose gel electrophoresis and Gel/PCR Purification Kit (FAVORGEN Biotech Corp.). The DNA fragment was ligated with the random mutation gene library obtained in the preceding paragraph (1) using DNA ligation kit ver. 2 (Takara Bio Inc.). An *E. coli* JM109 strain was transformed with the reaction solution.

The *E. coli* transformant was cultured on LBAmp agar medium. Approximately 12,000 colonies were recovered, and a bacterial cell suspension was prepared. Plasmids were prepared from an aliquot of the bacterial cell suspension using Mini prep Kit (Qiagen N.V.) and used as a mutated AAT(M2K)-CAT fusion gene plasmid library.

(4) Screening for Highly Soluble AAT with Chloramphenicol Resistance as Index and Identification of Mutation Position An *E. coli* JM109 strain was transformed with the mutated AAT (M2K)-CAT fusion gene plasmid library obtained in the preceding paragraph (3). The culture solution of the *E. coli* transformant was spread over LB agar medium containing 30 mg/l chloramphenicol and 0.4 mM IPTG and cultured overnight at 37° C. The obtained colonies were liquid-cultured, and plasmids were prepared. The AAT gene sequences in the plasmids were analyzed to identify mutation positions (Table 3).

TABLE 3

|  | Mutation position | Plasmid name |
|---|---|---|
| 1 | Q363K | pAAT119 |
| 2 | K117Q | pAAT120 |
| 3 | A64V | pAAT121 |
| 4 | G297D | pAAT122 |
| 5 | D415N | pAAT123 |
| 6 | V248A | pAAT124 |
| 7 | Q408H | pAAT125 |
| 8 | F4L | pAAT126 |
| 9 | L7F | pAAT127 |
| 10 | G220D | pAAT128 |
| 11 | N411S | pAAT129 |
| 12 | S3G | pAAT130 |
| 13 | Q440H | pAAT131 |
| 14 | P87R | pAAT132 |
| 15 | Q231E | pAAT133 |
| 16 | S232N | pAAT134 |

(5) AAT Activity Evaluation of Mutant Containing Identified Mutation

Plasmids for the expression of mutants containing the mutations shown in "Table 3" were prepared (Table 4).

First, PCR was performed with pAAT116 as a template using primer sets shown in "Table 4" below. 1 µl of DpnI was added to each reaction solution, and the mixture was incubated at 37° C. for 1 hour. An *E. coli* JM109 strain was transformed with the DpnI-treated solution. A plasmid containing each mutant AAT gene was prepared from the *E. coli* transformant.

TABLE 4

| Plasmid | Mutation position | | Name | Primer set Sequence | SEQ ID NO: |
|---|---|---|---|---|---|
| pAAT119 | Q363K | F | MMA-207 | GCGCGGTCGTCCGAAATACTCCAGCACGG | 27 |
|  |  | R | MMA-208 | CCGTGCTGGAGTATTTCGGACGACCGCGC | 28 |
| pAAT120 | K117Q | F | MMA-215 | GAACAGCTGGGCGACCAGATCCTGCCGCCG | 29 |
|  |  | R | MMA-216 | CGGCGGCAGGATCTGGTCGCCCAGCTGTTC | 30 |
| pAAT121 | A64V | F | MMA-217 | AATCCGGTTAAGGTCATTCGTGAGGCCCTG | 31 |
|  |  | R | MMA-218 | CAGGGCCTCACGAATGACCTTAACCGGATT | 32 |
| pAAT122 | G297D | F | MMA-219 | CGTTAACGCGCGTGATAAACACAACAATGT | 33 |
|  |  | R | MMA-220 | ACATTGTTGTGTTTATCACGCGCGTTAACG | 34 |
| pAAT123 | D415N | F | MMA-221 | AGAACAACACGGAAAATGGTATCTTGGTTC | 35 |
|  |  | R | MMA-222 | GAACCAAGATACCATTTTCCGTGTTGTTCT | 36 |
| pAAT124 | V248A | F | MMA-223 | GCGAAAGAAATGCGTGCTCTGCGCAAGCAG | 37 |
|  |  | R | MMA-224 | CTGCTTGCGCAGAGCACGCATTTCTTTCGC | 38 |
| pAAT125 | Q408H | F | MMA-225 | AGCTTCTATGTTCACCATAAGAACAACACG | 39 |
|  |  | R | MMA-226 | CGTGTTGTTCTTATGGTGAACATAGAAGCT | 40 |
| pAAT126 | F46L | F | MMA-241 | AGACCATGAAAAGCCTTTCTGTACTCCAAG | 41 |
|  |  | R | MMA-242 | CTTGGAGTACAGAAAGGCTTTTCATGGTCT | 42 |
| pAAT127 | L7F | F | MMA-243 | GAAAAGCTTTTCTGTATTCCAAGTCAAACG | 43 |
|  |  | R | MMA-244 | CGTTTGACTTGGAATACAGAAAAGCTTTTC | 44 |
| pAAT128 | G220D | F | MMA-229 | TACGAGGACGTTATCGACCATAGCGACGGC | 45 |
|  |  | R | MMA-230 | GCCGTCGCTATGGTCGATAACGTCCTCGTA | 46 |
| pAAT129 | N411S | F | MMA-231 | ATGTTCAACATAAGAGCAACACGGAAGATG | 47 |
|  |  | R | MMA-232 | CATCTTCCGTGTTGCTCTTATGTTGAACAT | 48 |
| pAAT130 | S3G | F | MMA-245 | AACAGACCATGAAAGGCTTTTCTGTACTCC | 49 |
|  |  | R | MMA-246 | GGAGTACAGAAAAGCCTTTCATGGTCTGTT | 50 |

TABLE 4-continued

| Plasmid | Mutation position | | Name | Primer set Sequence | SEQ ID NO: |
|---|---|---|---|---|---|
| pAAT131 | Q440H | F | MMA-233 | TGGAGCGCATTACCCACGAACCGAAAGAGG | 51 |
|  |  | R | MMA-234 | CCTCTTTCGGTTCGTGGGTAATGCGCTCCA | 52 |
| pAAT132 | P87R | F | MMA-239 | CGTCTGCGTGAGGGTCGGAATCGCAAACTG | 53 |
|  |  | R | MMA-240 | CAGTTTGCGATTCCGACCCTCACGCAGACG | 54 |
| pAAT133 | Q231E | F | MMA-237 | CGCGAGCAGCAACGAAAGCAATATGGTGCA | 55 |
|  |  | R | MMA-238 | TGCACCATATTGCTTTCGTTGCTGCTCGCG | 56 |
| pAAT134 | S232N | F | MMA-235 | GAGCAGCAACCAAAACAATATGGTGCAGCG | 57 |
|  |  | R | MMA-236 | CGCTGCACCATATTGTTTTGGTTGCTGCTC | 58 |

An *E. coli* JM109 strain was transformed with each plasmid shown in "Table 4", and the AAT activity of a cell homogenate of the *E. coli* transformant was measured by the method described in Example 1. The results are shown in "Table 5". In the table, the value of activity is indicated by a relative value when the activity of the reference form expressed from pAAT116 is defined as 1.

TABLE 5

| | | Relative activity | |
|---|---|---|---|
| Plasmid | Mutation position | 1st measurement | 2nd measurement |
| pAAT116 | — | 1 | 1 |
| pAAT119 | Q363K | 1.3 | 1.2 |
| pAAT120 | K117Q | 1.1 | 0.9 |
| pAAT121 | A64V | 1.9 | 1.6 |
| pAAT122 | G297D | 0.7 | 0.5 |
| pAAT123 | D415N | 0.8 | 0.8 |
| pAAT124 | V248A | 1.3 | 1.4 |
| pAAT125 | Q408H | 0.8 | 0.8 |
| pAAT126 | F4L | N.T. | 1.0 |
| pAAT127 | L7F | 0.7 | 1.0 |
| pAAT128 | G220D | 0.5 | 0.8 |
| pAAT129 | N411S | 0.9 | 0.9 |
| pAAT130 | S3G | 0.5 | 0.5 |
| pAAT131 | Q440H | 1.0 | 0.8 |
| pAAT132 | P87R | 0.4 | 0.4 |
| pAAT133 | Q231E | 1.0 | 1.0 |
| pAAT134 | S232N | 1.1 | 0.9 |

N.T.: unmeasured

Improvement in AAT activity was confirmed by the introduction of the A64V, V248A and Q363K mutations. The K117Q mutation also exhibited slight improvement in activity. Although not shown in the table, the substitution of alanine residue 64 by isoleucine or threonine, and the substitution of glutamine residue 363 by proline, alanine, arginine, glycine or tryptophan were also confirmed to offer 120% or more activity relative to the activity of the reference form expressed from pAAT116.

Next, a quadruple mutant of A64V, K117Q, V248A and Q363K was prepared.

(6) Preparation and Activity Evaluation of Quadruple Mutant

The AAT gene having 4 mutations A64V, K117Q, V248A and Q363K was synthesized by consignment (GenScript Biotech Corp.) and inserted to a vector pTrc99A to obtain a plasmid pAAT021. An *E. coli* JM109 strain was transformed with the plasmid pAAT021, and the AAT activity of a cell homogenate of the *E. coli* transformant was measured by the method described in Example 1.

The results are shown in FIG. 5. The quadruple mutant exhibited activity of approximately 6 times the activity of the reference form expressed from pAAT116.

Example 2: Preparation and Activity Evaluation of 6-Cysteine Substitution Quadruple Mutant The AAT gene encoding a mutant in which all the cysteine residues 48, 150, 167, 270, 274 and 447 of AAT were substituted by alanine, and 4 mutations A64V, K117Q, V248A and Q363K were present was synthesized by consignment (GenScript Biotech Corp.) and inserted to a vector pTrc99A to obtain a plasmid pAAT025. An *E. coli* JM109 strain was transformed with the plasmid pAAT025, and the AAT activity of a cell homogenate of the *E. coli* transformant was measured by the method described in Example 1.

The results are shown in FIG. 5. The 6-cysteine substitution quadruple mutant exhibited activity per recombinant of approximately 2.8 times the activity of the reference form (quadruple mutant) expressed from pAAT021.

Example 3: Preparation and Activity Evaluation of 6-Cysteine Substitution Quadruple Mutant—2

A plasmid pAAT155 derived from the plasmid pAAT021 (quadruple mutant) by the substitution of cysteine residue 150 of AAT by arginine, and a plasmid pAAT154 derived from pAAT025 (6-cysteine substitution quadruple mutant) by the substitution of cysteine residue 150 of AAT by arginine were prepared.

The plasmid pAAT155 contains a gene encoding mutant AAT having the substitution of cysteine residue 150 of AAT by arginine and a quadruple mutation of A64V, K117Q, V248A and Q363K.

The plasmid pAAT154 contains a gene encoding mutant AAT having the substitution of all the cysteine residues 48, 167, 270, 274 and 447 of AAT by alanine, the substitution of cysteine residue 150 by arginine and a quadruple mutation of A64V, K117Q, V248A and Q363K.

The amino acid substation was performed in accordance with the preparation of pAAT116 from pAAT115 in Reference Example 1. PCR reaction was performed with pAAT021 or pAAT025 as a template using primers MMA-380 and MMA-381.

Primer MMA-380 (SEQ ID NO: 59):
CTGATTCAAGTCACTCGTCTGACGTGTGGTGG

Primer MMA-381 (SEQ ID NO: 60):
CCACCACACGTCAGACGAGTGACTTGAATCAG

An *E. coli* JM109 strain was transformed with the plasmid pAAT155 or pAAT154, and the AAT activity of a cell homogenate of the *E. coli* transformant was measured by the method described in Example 1. A cell extract (soluble fraction) and an insoluble fraction (bacterial cells and membrane fractions) separated from the cell extract by centrifugation were separated by SDS-polyacrylamide gel electrophoresis, and a band of the recombinant AAT protein was detected.

The results are shown in FIG. 5. The recombinants expressing mutant AAT from pAAT155 and pAAT154 exhibited AAT activity per recombinant of approximately 3.7 times and approximately 5 times, respectively, the activity of the reference form (quadruple mutant) expressed from pAAT021. Also, the proteins expressed by the recombinants expressing mutant AAT from pAAT155 and pAAT154 were more abundant in the soluble fraction as compared with the recombinant expressing the reference form. These results demonstrated that the substitution of cysteine residue 150, particularly, by arginine further enhances the solubility of the reference form and further improves activity.

Example 4: Preparation and Activity Evaluation of 4- or 5-Cysteine Substitution Quadruple Mutant The AAT gene encoding a mutant in which 5 or 4 of the 6 cysteine residues 48, 150, 167, 270, 274 and 447 of AAT were substituted by alanine, and 4 mutations A64V, K117Q, V248A and Q363K were present was synthesized by consignment (GenScript Biotech Corp.) and inserted to a vector pTrc99A to obtain plasmids shown in "Table 6". An *E. coli* JM109 strain was transformed with each plasmid, and the AAT activity of a cell homogenate of the *E. coli* transformant was measured by the method described in Example 1.

TABLE 6

| Plasmid name | Mutation position | Remarks |
|---|---|---|
| pAAT151 | Cys48A, Cys150A, Cys270A, Cys274A, Cys447A A64V, K117Q, V248A, Q363K, | 5 substitutions Quadruple mutation |
| pATM017 | Cys48A, Cys270A, Cys274A, Cys447A A64V, K117Q, V248A, Q363K, | 4 substitutions Quadruple mutation |
| pATM018 | Cys48A, Cys150A, Cys270A, Cys274A A64V, K117Q, V248A, Q363K, | 4 substitutions Quadruple mutation |
| pATM019 | Cys150A, Cys270A, Cys274A, Cys447A A64V, K117Q, V248A, Q363K, | 4 substitutions Quadruple mutation |
| pATM021 | Cys48A, Cys150A, Cys270A, Cys447A A64V, K117Q, V248A, Q363K, | 4 substitutions Quadruple mutation |

The results are shown in FIG. 6. The ordinate of the graph indicates AAT activity per bacterial cell weight when the activity of the reference form expressed from pAAT116 is defined as 1. All the 5-cysteine substitution quadruple mutant and the 4-cysteine substitution quadruple mutants exhibited higher solubility and activity per recombinant than those of the reference form (quadruple mutant) expressed from pAAT021.

Example 5: Production of Highly Active Tomato AAT (1) Preparation of Recombinant Expressing Mutant in which Cysteine Residue was Substituted by Alanine Residue A plasmid pAAT032 for the expression of the tomato AAT (SpAAT) gene was synthesized by consignment (GenScript Biotech Corp.; the same holds true for the description below). pAAT032 contains a gene encoding tomato (wild species) A2K mutant AAT (SEQ ID NO: 64) in which the amino acid alanine at position 2 of tomato (wild species) wild-type AAT (SEQ ID NO: 66) was substituted by lysine. The protein encoded by this gene has 8 cysteine residues. 8 plasmids in which each cysteine was substituted by alanine were synthesized by consignment (Table 7).

TABLE 7

| Plasmid name | Position of substituted cysteine residue | Codon of substituted alanine |
|---|---|---|
| pAAT032 | — | — |
| pATM101 | Position 94 | GCG |
| pATM102 | Position 121 | GCG |
| pATM103 | Position 152 | GCG |
| pATM104 | Position 206 | GCG |
| pATM105 | Position 209 | GCG |
| pATM106 | Position 256 | GCG |
| pATM107 | Position 269 | GCG |
| pATM108 | Position 322 | GCG |

An *E. coli* JM109 strain was transformed with each of 9 plasmids shown in "Table 7".

(2) AAT Activity Measurement of Cell Extract Containing Mutant

The *E. coli* transformant was cultured in the same way as in Example 1. Bacterial cells were recovered, and a cell extract was prepared, followed by the measurement of AAT activity. The results are shown in FIG. 7.

Five mutants that exhibited 50% or more AAT activity per recombinant relative to 100% activity of the reference form expressed from pAAT032 were obtained (mutants expressed from pATM104, pATM105, pATM106, pATM107 and pATM108).

(3) Preparation of Recombinant Expressing Mutant in which 5 Cysteine Residues were Substituted by Alanine Residues Accordingly, a plasmid pAAT164 containing a gene encoding a mutant containing all the amino acid substitutions C206A, C209A, C256A, C269A and C322A of these 5 mutants was synthesized by consignment. Results of measuring AAT activity are shown in FIG. 7.

The mutant expressed from pAAT164 exhibited AAT activity per recombinant of approximately 3 times the activity of the reference form. Also, the mutant expressed from pAAT164 was more abundant in the soluble fraction as compared with the reference form. These results demonstrated that the substitution of cysteine residues 206, 209, 256, 269 and 322 by alanine enhances the solubility of AAT and improves activity per recombinant.

Example 6: Production of Highly Active Garden Strawberry AAT (1) Preparation of Recombinant Expressing Mutant in which Cysteine Residue was Substituted by Alanine Residue A plasmid pAAT033 for the expression of a gene of garden strawberry AAT (SAAT) (SEQ ID NO: 65) was synthesized by consignment. The protein encoded by this gene has 9 cysteine residues. 9 plasmids in which each cysteine was substituted by alanine were synthesized by consignment (Table 8).

TABLE 8

| Plasmid name | Position of substituted cysteine residue | Codon of substituted alanine |
|---|---|---|
| pAAT033 | — | — |
| pATM201 | Position 102 | GCG |
| pATM202 | Position 115 | GCG |
| pATM203 | Position 167 | GCG |
| pATM204 | Position 179 | GCG |
| pATM205 | Position 325 | GCG |
| pATM206 | Position 338 | GCG |
| pATM207 | Position 356 | GCG |
| pATM208 | Position 408 | GCG |
| pATM209 | Position 418 | GCG |

An *E. coli* JM109 strain was transformed with each of 10 plasmids shown in "Table 8".

(2) AAT Activity Measurement of Cell Extract Containing Mutant

The *E. coli* transformant was cultured in the same way as in Example 1. Bacterial cells were recovered, and a cell extract was prepared, followed by the measurement of AAT activity. The results are shown in FIG. 8.

Seven mutants that exhibited 50% or more AAT activity per recombinant relative to 100% activity of the reference form expressed from pAAT033 were obtained (mutants expressed from pATM202, pATM203, pATM204, pATM205, pATM206, pATM207 and pATM208).

(3) Preparation of Recombinant Expressing Mutant in which 5 Cysteine Residues were Substituted by Alanine Residues A plasmid pAAT037 containing a gene encoding a mutant containing C115A, C167A, C179A, C325A and C356A among the amino acid substitutions of these 7 mutants was synthesized by consignment. Results of measuring AAT activity are shown in FIG. 8.

The mutant expressed from pAAT037 exhibited AAT activity per recombinant of approximately 1.7 times the activity of the reference form. These results demonstrated that the substitution of cysteine residues 115, 167, 179, 325 and 356 by alanine improves activity per recombinant.

Free Text of Sequence Listing
SEQ ID NO: 1: Apple wild-type AAT (Mp-AAT1_apple)
SEQ ID NO: 2: Apple M2K mutant AAT
SEQ ID NO: 3: AAT containing a quadruple mutation introduced in the apple M2K mutant
SEQ ID NO: 4: AAT containing 6 cysteine substitutions introduced in the apple M2K mutant
SEQ ID NO: 5: AAT containing a quadruple mutation and 6 cysteine substitutions introduced in the apple M2K mutant
SEQ ID NO: 6: AAT containing a quadruple mutation and Cys150Arg introduced in the apple M2K mutant
SEQ ID NO: 7: AAT containing a quadruple mutation and 6 cysteine substitutions (including Cys150Arg at position 150) introduced in the apple M2K mutant
SEQ ID NO: 8: AAT containing a quadruple mutation and 5 cysteine substitutions introduced in the apple M2K mutant
SEQ ID NO: 9: AAT containing a quadruple mutation and 4 cysteine substitutions introduced in the apple M2K mutant
SEQ ID NO: 10: AAT containing a quadruple mutation and 4 cysteine substitutions introduced in the apple M2K mutant
SEQ ID NO: 11: AAT containing a quadruple mutation and 4 cysteine substitutions introduced in the apple M2K mutant
SEQ ID NO: 12: Amino acid sequence of apple-derived AAT (Md-AAT2 apple)
SEQ ID NO: 13: AAT containing a quadruple mutation and 4 cysteine substitutions introduced in the apple M2K mutant
SEQ ID NO: 14: Wild-type apple AAT gene optimized for *E. coli* codons
SEQ ID NO: 15: Primer MMA-156
SEQ ID NO: 16: Primer MMA-163
SEQ ID NO: 17: Primer MMA-166
SEQ ID NO: 18: Primer MMA-169
SEQ ID NO: 19: Primer MMA-185
SEQ ID NO: 20: Primer MMA-157
SEQ ID NO: 21: Primer MMA-152
SEQ ID NO: 22: Primer MMA-153
SEQ ID NO: 23: Primer MMA-156
SEQ ID NO: 24: Primer MMA-157
SEQ ID NO: 25: Primer MMA-159
SEQ ID NO: 26: Primer MMA-160
SEQ ID NO: 27: Primer MMA-207
SEQ ID NO: 28: Primer MMA-208
SEQ ID NO: 29: Primer MMA-215
SEQ ID NO: 30: Primer MMA-216
SEQ ID NO: 31: Primer MMA-217
SEQ ID NO: 32: Primer MMA-218
SEQ ID NO: 33: Primer MMA-219
SEQ ID NO: 34: Primer MMA-220
SEQ ID NO: 35: Primer MMA-221
SEQ ID NO: 36: Primer MMA-222
SEQ ID NO: 37: Primer MMA-223
SEQ ID NO: 38: Primer MMA-224
SEQ ID NO: 39: Primer MMA-225
SEQ ID NO: 40: Primer MMA-226
SEQ ID NO: 41: Primer MMA-241
SEQ ID NO: 42: Primer MMA-242
SEQ ID NO: 43: Primer MMA-243
SEQ ID NO: 44: Primer MMA-244
SEQ ID NO: 45: Primer MMA-229
SEQ ID NO: 46: Primer MMA-230
SEQ ID NO: 47: Primer MMA-231
SEQ ID NO: 48: Primer MMA-232
SEQ ID NO: 49: Primer MMA-245
SEQ ID NO: 50: Primer MMA-246
SEQ ID NO: 51: Primer MMA-233
SEQ ID NO: 52: Primer MMA-234
SEQ ID NO: 53: Primer MMA-239
SEQ ID NO: 54: Primer MMA-240
SEQ ID NO: 55: Primer MMA-237
SEQ ID NO: 56: Primer MMA-238
SEQ ID NO: 57: Primer MMA-235
SEQ ID NO: 58: Primer MMA-236
SEQ ID NO: 59: Primer MMA-380
SEQ ID NO: 60: Primer MMA-381
SEQ ID NO: 61: Amino acid sequence of Asian pear (*Pyrus pyrifolia*)-derived AAT
SEQ ID NO: 62: Amino acid sequence of loquat (*Eriobotrya japonica*)-derived AAT
SEQ ID NO: 63: Amino acid sequence of kaki persimmon (*Diospyros kaki*)-derived AAT
SEQ ID NO: 64: Tomato (wild species) A2K mutant AAT
SEQ ID NO: 65: Amino acid sequence of garden strawberry (*Fragaria×ananassa*) wild-type AAT
SEQ ID NO: 66: Amino acid sequence of tomato (wild species) (*Solanum pennellii*) wild-type AAT
SEQ ID NO: 67: Amino acid sequence of tomato (cultivated species) (*Solanum lycopersicum*)-derived AAT
SEQ ID NO: 68: Amino acid sequence of potato (*Solanum tuberosum*)-derived AAT
SEQ ID NO: 69: Amino acid sequence of pepper (*Capsicum annuum*)-derived AAT SEQ ID NO: 70: Amino acid sequence of tobacco (*Nicotiana tabacum*)-derived AAT
SEQ ID NO: 71: Amino acid sequence of beach strawberry (*Fragaria chiloensis*)-derived AAT
SEQ ID NO: 72: Amino acid sequence of woodland strawberry (*Fragaria vesca*)-derived AAT
SEQ ID NO: 73: Amino acid sequence of Japanese rose (*Rosa rugosa*)-derived AAT

The invention claimed is:

1. A mutant alcohol acyltransferase comprising of an amino acid sequence having 95% sequence identity or higher to the amino acid sequence of SEQ ID NO: 1 or 2, wherein
the mutant alcohol acyltransferase has at least one amino acid substitutions selected from the group consisting of amino acid substitutions (1), (2), (3), (4), (5) and (6):
(1) a substitution of cysteine corresponding to cysteine at position 48 in alignment with the amino acid sequence of SEQ ID NO: 1 or 2 by another amino acid residue,
(2) a substitution of cysteine corresponding to cysteine at position 150 in alignment with the amino acid sequence of SEQ ID NO: 1 or 2 by another amino acid residue,
(3) a substitution of cysteine corresponding to cysteine at position 167 in alignment with the amino acid sequence of SEQ ID NO: 1 or 2 by another amino acid residue,
(4) a substitution of cysteine corresponding to cysteine at position 270 in alignment with the amino acid sequence of SEQ ID NO: 1 or 2 by another amino acid residue,
(5) a substitution of cysteine corresponding to cysteine at position 274 in alignment with the amino acid sequence of SEQ ID NO: 1 or 2 by another amino acid residue, and
(6) a substitution of cysteine corresponding to cysteine at position 447 in alignment with the amino acid sequence of SEQ ID NO: 1 or 2 by another amino acid residue.

2. The mutant alcohol acyltransferase according to claim 1, consisting of an amino acid sequence having 70% or higher sequence identity to the amino acid sequence of SEQ ID NO: 64 or 66, wherein
the mutant alcohol acyltransferase has at least one amino acid substitution selected from the group consisting of amino acid substitutions (1), (2), (3), (4) and (5):
(1) a substitution of cysteine corresponding to cysteine at position 206 in alignment with the amino acid sequence of SEQ ID NO: 64 or 66 by another amino acid residue,
(2) a substitution of cysteine corresponding to cysteine at position 209 in alignment with the amino acid sequence of SEQ ID NO: 64 or 66 by another amino acid residue,
(3) a substitution of cysteine corresponding to cysteine at position 256 in alignment with the amino acid sequence of SEQ ID NO: 64 or 66 by another amino acid residue,
(4) a substitution of cysteine corresponding to cysteine at position 269 in alignment with the amino acid sequence represented by SEQ ID NO: 64 or 66 by another amino acid residue, and
(5) a substitution of cysteine corresponding to cysteine at position 322 in alignment with the amino acid sequence of SEQ ID NO: 64 or 66 by another amino acid residue.

3. The mutant alcohol acyltransferase according to claim 1, consisting of an amino acid sequence having 70% or higher sequence identity to the amino acid sequence of SEQ ID NO: 65, wherein
the mutant alcohol acyltransferase has at least one amino acid substitution selected from the group consisting of amino acid substitutions (1), (2), (3), (4) and (5):
(1) a substitution of cysteine corresponding to cysteine at position 115 in alignment with the amino acid sequence of SEQ ID NO: 65 by another amino acid residue,
(2) a substitution of cysteine corresponding to cysteine at position 167 in alignment with the amino acid sequence of SEQ ID NO: 65 by another amino acid residue,
(3) a substitution of cysteine corresponding to cysteine at position 179 in alignment with the amino acid sequence of SEQ ID NO: 65 by another amino acid residue,
(4) a substitution of cysteine corresponding to cysteine at position 325 in alignment with the amino acid sequence of SEQ ID NO: 65 by another amino acid residue, and
(5) a substitution of cysteine corresponding to cysteine at position 356 in alignment with the amino acid sequence of SEQ ID NO: 65 by another amino acid residue.

4. The mutant alcohol acyltransferase according to claim 1, wherein the other amino acid residue is alanine or arginine.

5. The mutant alcohol acyltransferase according to claim 1, wherein the mutant alcohol acyltransferase has at least one amino acid substitution selected from the group consisting of amino acid substitutions (1), (2), (3), (4), (5) and (6) in the amino acid sequence of SEQ ID NO: 1 or 2:
(1) a substitution of cysteine at position 48 by another amino acid residue,
(2) a substitution of cysteine at position 150 by another amino acid residue,
(3) a substitution of cysteine at position 167 by another amino acid residue,
(4) a substitution of cysteine at position 270 by another amino acid residue,
(5) a substitution of cysteine at position 274 by another amino acid residue, and
(6) a substitution of cysteine at position 447 by another amino acid residue.

6. The mutant alcohol acyltransferase according to claim 1, wherein the mutant alcohol acyltransferase has at least one amino acid substitution selected from the group consisting of amino acid substitutions (1), (2), (3), (4) and (5) in the amino acid sequence of SEQ ID NO: 64 or 66:
(1) a substitution of cysteine at position 206 by another amino acid residue,
(2) a substitution of cysteine at position 209 by another amino acid residue,
(3) a substitution of cysteine at position 256 by another amino acid residue,
(4) a substitution of cysteine at position 269 by another amino acid residue, and
(5) a substitution of cysteine at position 322 by another amino acid residue.

7. The mutant alcohol acyltransferase according to claim 1, wherein the mutant alcohol acyltransferase has at least one amino acid substitutions selected from the group consisting of amino acid substitutions (1), (2), (3), (4) and (5) in the amino acid sequence of SEQ ID NO: 65:
(1) a substitution of cysteine at position 115 by another amino acid residue,
(2) a substitution of cysteine at position 167 by another amino acid residue,
(3) a substitution of cysteine at position 179 by another amino acid residue,
(4) a substitution of cysteine at position 325 by another amino acid residue, and
(5) a substitution of cysteine at position 356 by another amino acid residue.

8. The mutant alcohol acyltransferase according to claim 5, wherein the other amino acid residue is alanine or arginine.

9. The mutant alcohol acyltransferase according to claim 5, consisting of the amino acid sequence of SEQ ID NO: 4 or 7.

10. The mutant alcohol acyltransferase according to claim 1, wherein the mutant alcohol acyltransferase further has at least one amino acid substitution selected from the group consisting of amino acid substitutions (1), (2), (3) and (4):
(1) a substitution of alanine at position 64 by valine, isoleucine or threonine,
(2) a substitution of lysine at position 117 by glutamine,
(3) a substitution of valine at position 248 by alanine, and
(4) a substitution of glutamine at position 363 by lysine, proline, alanine, arginine, glycine or tryptophan.

11. The mutant alcohol acyltransferase according to claim 10, consisting of the amino acid sequence of SEQ ID NO: 5, 6, 8, 9, 10, 11, or 13.

12. A vector expressing the alcohol acyltransferase of claim 1.

13. A transformant transformed by the vector of claim 12.

14. The mutant alcohol acyltransferase according to claim 1, wherein the mutant alcohol acyltransferase comprises a substitution of cysteine corresponding to cysteine at position 150 in alignment with the amino acid sequence of SEQ ID NO: 1 or 2 by another amino acid residue.

15. A method for producing methacrylic acid ester using the alcohol acyltransferase according to claim 1.

* * * * *